US007186855B2

(12) United States Patent
Gallop et al.

(10) Patent No.: US 7,186,855 B2
(45) Date of Patent: Mar. 6, 2007

(54) PRODRUGS OF GABA ANALOGS, COMPOSITIONS AND USES THEREOF

(75) Inventors: Mark A. Gallop, Los Altos, CA (US); Kenneth C. Cundy, Redwood City, CA (US); Cindy X. Zhou, Palo Alto, CA (US); Fayang Gregory Qiu, Mountain View, CA (US); Fenmei Yao, Mountain View, CA (US); Jia-Ning Xiang, Palo Alto, CA (US); Ian R. Ollman, San Mateo, CA (US)

(73) Assignee: Xenoport, Inc., Santa Clara, CA (US)

( * ) Notice: Subject to any disclaimer, the term of this patent is extended or adjusted under 35 U.S.C. 154(b) by 500 days.

(21) Appl. No.: 10/313,825

(22) Filed: Dec. 6, 2002

(65) Prior Publication Data

US 2004/0077553 A1  Apr. 22, 2004

Related U.S. Application Data

(63) Continuation-in-part of application No. 10/171,485, filed on Jun. 11, 2002, now Pat. No. 6,818,787.

(60) Provisional application No. 60/366,090, filed on Mar. 19, 2002, provisional application No. 60/298,514, filed on Jun. 14, 2001, provisional application No. 60/297,521, filed on Jun. 11, 2001.

(51) Int. Cl.
*C07C 271/22* (2006.01)
*A01N 43/00* (2006.01)
*A61K 31/544* (2006.01)

(52) U.S. Cl. ..................... 560/115; 514/211
(58) Field of Classification Search .............. 514/211; 560/115
See application file for complete search history.

(56) References Cited

U.S. PATENT DOCUMENTS

| 3,845,770 A | 11/1974 | Theeuwes et al. |
| 3,916,899 A | 11/1975 | Theeuwes et al. |
| 4,024,175 A | 5/1977 | Satzinger et al. |
| 4,036,829 A | 7/1977 | Ferres et al. |
| 4,152,326 A | 5/1979 | Hartenstein et al. |
| 4,189,571 A | 2/1980 | Bodor et al. |
| 4,377,590 A | 3/1983 | Myers |
| 4,611,056 A | 9/1986 | Guindon et al. |
| 4,760,057 A | 7/1988 | Alexander |
| 4,916,230 A | 4/1990 | Alexander |
| 5,051,448 A | 9/1991 | Shashoua |
| 5,084,479 A | 1/1992 | Woodruff |
| 5,112,598 A | 5/1992 | Biesalski |
| 5,281,585 A | 1/1994 | Duggan et al. |
| 5,401,868 A | 3/1995 | Lund |
| 5,466,811 A | 11/1995 | Alexander |
| 5,556,611 A | 9/1996 | Biesalski |
| 5,563,175 A | 10/1996 | Silverman et al. |
| 5,580,872 A | 12/1996 | Chu et al. |
| 5,599,973 A | 2/1997 | Silverman et al. |
| 5,602,118 A | 2/1997 | Lin et al. |
| 5,622,944 A | 4/1997 | Hale et al. |
| 5,672,584 A | 9/1997 | Borchardt et al. |
| 5,684,018 A | 11/1997 | Alexander |
| 5,698,155 A | 12/1997 | Grosswald et al. |
| 6,001,876 A | 12/1999 | Singh |
| 6,020,370 A | 2/2000 | Horwell et al. |
| 6,022,969 A | 2/2000 | Rice et al. |
| 6,024,977 A | 2/2000 | Yatvin et al. |
| 6,028,214 A | 2/2000 | Silverman et al. |
| 6,054,482 A | 4/2000 | Augart et al. |
| 6,103,932 A | 8/2000 | Horwell et al. |
| 6,117,906 A | 9/2000 | Silverman et al. |
| 6,127,418 A | 10/2000 | Bueno et al. |
| 2002/0028806 A1 | 3/2002 | Goebel et al. |
| 2002/0055522 A1 | 5/2002 | Liebeschuetz et al. |
| 2002/0107208 A1 | 8/2002 | Chen et al. |
| 2002/1017208 | 8/2002 | Chen et al. |

FOREIGN PATENT DOCUMENTS

| CA | 1085420 A1 | 9/1980 |
| DE | 4424975 A1 | 1/1996 |
| DE | 19804085 A1 | 8/1999 |
| DE | 19816983 A1 | 10/1999 |
| EP | 23192 B1 | 3/1984 |
| EP | 69378 B1 | 1/1987 |
| EP | 70204 B1 | 11/1987 |
| EP | 136893 B1 | 8/1989 |
| EP | 429232 A1 | 5/1991 |
| EP | 458751 A1 | 11/1991 |
| EP | 234485 B1 | 4/1992 |
| EP | 416373 A3 | 5/1992 |

(Continued)

OTHER PUBLICATIONS

Beller et al., in "Transition Metals in Organic Synthesis" Chapter 2, Wiley VCH.

(Continued)

*Primary Examiner*—James O. Wilson
*Assistant Examiner*—Paul V. Ward
(74) *Attorney, Agent, or Firm*—Richard F. Trecartin, Esq.; Dorsey & Whitney LLP

(57) ABSTRACT

The present invention provides prodrugs of GABA analogs, pharmaceutical compositions of prodrugs of GABA analogs and methods for making prodrugs of GABA analogs. The present invention also provides methods for using prodrugs of GABA analogs and methods for using pharmaceutical compositions of prodrugs of GABA analogs for treating or preventing common diseases and/or disorders.

4 Claims, No Drawings

FOREIGN PATENT DOCUMENTS

| | | |
|---|---|---|
| EP | 138481 B1 | 6/1992 |
| EP | 200692 B1 | 11/1992 |
| EP | 587134 A3 | 7/1994 |
| EP | 381661 B2 | 5/1995 |
| EP | 584694 B1 | 1/1998 |
| EP | 617036 A3 | 1/1998 |
| EP | 327766 B1 | 4/1998 |
| EP | 335545 B2 | 9/1998 |
| EP | 567966 B1 | 9/1998 |
| EP | 781778 B1 | 4/2000 |
| EP | 656348 B1 | 5/2000 |
| EP | 1 178 034 A1 | 2/2002 |
| EP | 1178034 A1 | 2/2002 |
| EP | 1226820 A1 | 7/2002 |
| FR | 83479 | 8/1964 |
| FR | 2476087 B1 | 7/1983 |
| FR | 2570695 A1 | 3/1986 |
| FR | 2783521 B1 | 4/2002 |
| JP | 54055562 A2 | 5/1979 |
| JP | 55015432 B4 | 2/1980 |
| JP | 57021400 A2 | 2/1982 |
| JP | 58222089 A2 | 12/1983 |
| JP | 59219268 A2 | 12/1984 |
| JP | 01113391 A2 | 5/1989 |
| JP | 01275565 A2 | 11/1989 |
| JP | 03072476 A2 | 3/1991 |
| JP | 05202059 A2 | 8/1993 |
| JP | 06228103 A2 | 8/1994 |
| JP | 06228149 A2 | 8/1994 |
| JP | 08217787 A2 | 8/1996 |
| JP | 08295668 A2 | 11/1996 |
| JP | 09015799 A2 | 1/1997 |
| JP | 09080709 A2 | 3/1997 |
| JP | 10287669 A2 | 10/1998 |
| JP | 11029533 A2 | 2/1999 |
| JP | 11199573 A2 | 7/1999 |
| JP | 2000344774 A2 | 12/2000 |
| JP | 03190857 B2 | 7/2001 |
| JP | 2002105041 A2 | 4/2002 |
| WO | WO 9011300 A1 | 10/1990 |
| WO | WO 9110639 A1 | 7/1991 |
| WO | WO 92-09560 A1 | 6/1992 |
| WO | WO 9318070 A1 | 9/1993 |
| WO | WO 93-23383 A1 | 11/1993 |
| WO | WO 9325197 A1 | 12/1993 |
| WO | WO 9420508 A1 | 9/1994 |
| WO | WO 9510519 A1 | 4/1995 |
| WO | WO 9525106 A1 | 9/1995 |
| WO | WO 9533720 A1 | 12/1995 |
| WO | WO 9609297 A1 | 3/1996 |
| WO | WO 9613497 A1 | 5/1996 |
| WO | WO 9620172 A1 | 7/1996 |
| WO | WO 9636613 A1 | 11/1996 |
| WO | WO 9638435 A3 | 12/1996 |
| WO | WO 9639407 A1 | 12/1996 |
| WO | WO 97-33858 A1 | 2/1997 |
| WO | WO 99-31057 A1 | 6/1997 |
| WO | WO 9723499 A1 | 7/1997 |
| WO | WO 97-29101 A1 | 8/1997 |
| WO | WO 97-33859 A1 | 9/1997 |
| WO | WO 9733858 A1 | 9/1997 |
| WO | WO 9733859 A1 | 9/1997 |
| WO | WO 9804537 A1 | 2/1998 |
| WO | WO 9806402 A1 | 2/1998 |
| WO | WO 9809957 A1 | 3/1998 |
| WO | WO 98-17627 A1 | 4/1998 |
| WO | WO 9815560 A1 | 4/1998 |
| WO | WO 9825920 A1 | 6/1998 |
| WO | WO 9839324 A1 | 9/1998 |
| WO | WO 9854164 A1 | 12/1998 |
| WO | WO 9900127 A1 | 1/1999 |
| WO | WO 99-08671 A1 | 2/1999 |
| WO | WO 9906402 A1 | 2/1999 |
| WO | WO 9911658 A1 | 3/1999 |
| WO | WO 99-21824 A1 | 5/1999 |
| WO | WO 9921824 A1 | 5/1999 |
| WO | WO 99-31075 A1 | 6/1999 |
| WO | WO 9931075 A1 | 6/1999 |
| WO | WO 9932480 A1 | 7/1999 |
| WO | WO 9937296 A1 | 7/1999 |
| WO | WO 9938829 A1 | 8/1999 |
| WO | WO 9940072 A1 | 8/1999 |
| WO | WO 9940075 A1 | 8/1999 |
| WO | WO 9952894 A1 | 10/1999 |
| WO | WO 9952903 A1 | 10/1999 |
| WO | WO 99-31074 A2 | 11/1999 |
| WO | WO 9931074 A3 | 11/1999 |
| WO | WO 9957121 A1 | 11/1999 |
| WO | WO 99-61424 A1 | 12/1999 |
| WO | WO 0009480 A1 | 2/2000 |
| WO | WO 00-15611 A1 | 3/2000 |
| WO | WO 0001704 A3 | 4/2000 |
| WO | WO 0023067 A1 | 4/2000 |
| WO | WO 00-31020 A1 | 6/2000 |
| WO | WO 0031062 A1 | 6/2000 |
| WO | WO 00-50027 A1 | 8/2000 |
| WO | WO 0064927 A1 | 11/2000 |
| WO | WO 0029378 A3 | 12/2000 |
| WO | WO 0073298 A1 | 12/2000 |
| WO | WO 0078723 A1 | 12/2000 |
| WO | WO 0103685 A3 | 1/2001 |
| WO | WO 0105749 A1 | 1/2001 |
| WO | WO 0105750 A1 | 1/2001 |
| WO | WO 0105768 A1 | 1/2001 |
| WO | WO 0105813 A1 | 1/2001 |
| WO | WO 0107032 A1 | 2/2001 |
| WO | WO 0110866 A1 | 2/2001 |
| WO | WO 0128978 A1 | 4/2001 |
| WO | WO 0130780 A3 | 5/2001 |
| WO | WO 0140180 A3 | 6/2001 |
| WO | WO 0142190 A1 | 6/2001 |
| WO | WO 0142191 A1 | 6/2001 |
| WO | WO 0154481 A2 | 8/2001 |
| WO | WO 0155082 A2 | 8/2001 |
| WO | WO 0156358 A2 | 8/2001 |
| WO | WO 0162242 A1 | 8/2001 |
| WO | WO 0170673 A3 | 9/2001 |
| WO | WO 0185718 A1 | 11/2001 |
| WO | WO 0190052 A1 | 11/2001 |
| WO | WO 0190081 A1 | 11/2001 |
| WO | WO 02-00209 A2 | 1/2002 |
| WO | WO 0200584 A1 | 1/2002 |
| WO | WO 0204458 A1 | 1/2002 |
| WO | WO 0204459 A1 | 1/2002 |
| WO | WO 0210120 A1 | 2/2002 |
| WO | WO 0216315 A1 | 2/2002 |
| WO | WO 0218327 A3 | 3/2002 |
| WO | WO 0228411 A1 | 4/2002 |
| WO | WO 0228827 A1 | 4/2002 |
| WO | WO 0228881 A1 | 4/2002 |
| WO | WO 0228883 A1 | 4/2002 |
| WO | WO 0232376 A2 | 4/2002 |
| WO | WO 0234698 A3 | 5/2002 |
| WO | WO 0234711 A1 | 5/2002 |
| WO | WO 0242414 A3 | 5/2002 |
| WO | WO 0244324 A2 | 6/2002 |
| WO | WO 0258680 | 8/2002 |
| WO | WO 0262766 | 8/2002 |
| WO | WO 0276980 | 10/2002 |
| WO | WO 0279189 | 10/2002 |
| WO | WO 0285855 | 10/2002 |
| WO | WO 0285928 | 10/2002 |
| WO | WO 0287632 | 11/2002 |
| WO | WO 0288092 | 11/2002 |

| WO | WO 0292555 | 11/2002 |
| WO | WO 0294829 | 11/2002 |
| WO | WO 02100344 A2 | 12/2002 |
| WO | WO 0300250 | 1/2003 |
| WO | WO 0300642 | 1/2003 |
| WO | WO 0300643 | 1/2003 |
| WO | WO 0305971 | 1/2003 |
| WO | WO 0309872 | 2/2003 |
| WO | WO 0330905 | 4/2003 |
| WO | WO 0335067 | 5/2003 |
| WO | WO 0340086 | 5/2003 |

OTHER PUBLICATIONS

Magnus, *Nonepileptic Uses of Gabapentin, Epilepsia*, (40) (Suppl. 6): S66-S72 (1999).
Peto et al., *The TD$_{50}$: A Proposed General Convention for the Numerical Description of the Carcinogenic Potency of Chemicals in Chronic-Exposure Animal Experiments, Envir. Health Perspectives*, vol. 58, 1-8 (1984).
Peto et al., *The TD$_{50}$: A Proposed General Convention for the Numerical Description of the Carcinogenic Potency of Chemicals in Chronic-Exposure Animal Experiments, Envir. Health Perspectives*, vol. 58, 1-8 (1984).
Saudek et al., *A Preliminary Trial of the Programmable Implantable Medication System for Insulin Delivery, N. Engl. J Med.* vol. 321, 574-579 (1989).
Stewart, *Cyclohexanone Monooxygenase: A Useful Reagent for Asymmetric Baeyer-Villiger Reactions, Current Organic Chemistry*, vol. 2, 195-216, (1998).
Strukul, *Transition Metal Catalysis in the Baeyer—Villger Oxidation of Ketones, Agnew Chem. Int.* Ed vol. 37, pp. 1198-1209 (1998).
U.S. Appl. No. 10/167,797, Gallop et al.
U.S. Appl. No. 10/170,127, Gallop et al.
U.S. Appl. No. 10/313,825, Gallop et al.
Albrecht et al., "Modular branced peptides: Synthesis of potential vaccines," *Pept.: Chem., Struct. Biol., Proc. Am. Pept. Sym., 11th* (1990), Meeting Date (1989) 718-20.
Alderman, "A Review of Cellulose Ethers in Hydrophilic Matrices for Oral Controlled-Release Dosage Forms," (1984) 5(3):1-9.
Alex et al., "Design and synthesis of penicilloyl oxymethyl quinolone carbamates as a new class of dual-acting antibacterials," *European Journal of Medicinal Chemistry* (1995), 30(10): 815-18.
Alexander et al., "(Acyloxy)alkyl carbamate prodrugs of norfloxacin," *Journal of Medicinal Chemistry* (1991), 34(1): 78-81.
Alexander et al., "(Acyloxy)alkyl carbamates as novel bioreversible prodrugs for amines: increased permeation through biological membranes," *Journal of Medicinal Chemistry* (1988), 31(2): 318-22.
Andruszkiewicz et al., "4-Amino-3-alkybutanoic acids as substrates for γ-aminobutyric acid aminotransferase," *Journal of Biological Chemistry* (1990), 265(36): 22288-91.
Andruszkiewicz et al., "Chemoenzymatic synthesis of (R)- and (S)-4-amino-3-methylbutanoic acids," *Synthetic Communications* (1990), 20(1): 159-66.
Bak et al. "Synthesis and evaluation of the physicochemical properties of esterase-sensitive cyclic prodrugs of opioid peptides using an (acyloxy)alkyl linker," *Journal of Peptide Research* (1999), 53(4): 393-402.
Bak et al., "Acyloxyalkoxy-based cyclic prodrugs of opioid peptides: evaluation of the chemical and enzymic stability as well as their transport properties across Caco-2 cell monolayers," *Pharmaceutical Research* (1999), 16(1): 24-29.
Bamba et al., "Release Mechanisms In Gelforming Sustained Release Preparations," *Int. J. Pharm.* (1979) 2: 307-315.
Barluenga et al., "Cycloaddition Reactions of Chiral 2-Amino-1,3-butadienes with Nitroalkenes: Synthesis of Enantiomerically Pure 4-Nitrocyclohexanones," *Journal of Organic Chemistry* (1997), 62(20): 6746-6753.
Bitha et al., "Convergent synthesis of oral THF 1β-methylcarbapenems," *Journal of Antibiotics* (1999), 52(7): 643-648.

Bohm et al., "Determination of enantiomer purity of β- and γ-amino acids by NMR analysis of diastereoisomeric palladium complexes," *Helvetica Chimica Acta* (2000), 83(12): 3263-3278.
Bolm et al., "Metal-catalyzed Baeyer-Villiger Reactions. Transition Metals for Organic Synthesis" (1998) 213-8.
Borchardt "Rational design of peptides with enhanced membrane permeability," *Medicinal Chemistry: Today and Tomorrow, Proceedings of the AFMC International Medicinal Chemistry Symposium*, Tokyo, Sep. 3-8, 1995 (1997), Meeting Date 1995, 191-196.
Brenner et al., "Enantioselective preparation of γ-amino acids and γ-lactams from nitro olefins and carboxylic acids, with the valine-derived 4-isopropyl-5,5-diphenyl-1,3-oxazolindin-2-one as an auxiliary," *Helvetica Chimica Acta* (1999), 82(12): 2365-2379.
Brown et al., "Experiments towards the synthesis of corrins. IV. Oxidation and ring expansion of 2,4,4-trimethyl-Δ$^1$-pyrroline 1-oxide," *Journal of the Chemical Society*, Abstracts (1959) 2105-8.
Bryans et al., "3-Substituted GABA Analogs with Central Nervous System Activity: A Review," *Med. Res. Rev.* (1999) 19:149-177.
Butcher, "Carbamate esters: A Simple, Mild Method of Formation," *Synlett* (1994) 825-826.
Carvalho et al., "Triazene Drug Metabolites. Part 17Synthesis and plasma hydrolysis of acyloxymethyl carbamate derivatives of antitumor triazenes," *Bioorganic & Medicinal Chemistry* (2000), 8(7): 1719-1725.
Chen et al., "Evaluation of the permeation characteristics of a model opioid peptide, H-Tyr-D-Ala-Gly-Phe-D-Leu-OH (DADLE), and its cyclic prodrugs across the blood-brain barrier using an in situ perfused rat brain model," *Journal of Pharmacology and Experimental Therapeutics* (2002), 303(2): 849-857.
Cronin et al., "Gas chromatographic-mass spectral analysis of the five-carbon β-,γ-, and δ-amino alkanoic acids," *Analytical Biochemistry* (1982), 124(1): 139-49.
De Bont et al., "Synthesis and biological activity of β-glucuronyl carbamate-based prodrugs of paclitaxel as potential candidates for ADEPT," *Bioorganic & Medicinal Chemistry* (1997), 5(2): 405-414.
During et al., "Controlled Release of Dopamine from a Polymeric Brain Implant; In Vivo Characterization," *Ann. Neurol.* (1989) 25:351-356.
Folkmann et al., "Acyloxymethyl carbonochloridates. New intermediates in prodrug synthesis," *Synthesis* (1990), 12: 1159-66.
Frackenpohl et al., "The outstanding biological stability of β- and γ-peptides toward proteolytic enzymes: an in vitro investigation with fifteen peptidases," *ChemBioChem* (2001), 2(6): 445-455.
Gangwar et al., "Synthesis of a Novel Esterase-Sensitive Cyclic Prodrug of a Hexapeptide Using an (Acyloxy)alkoxy Promoiety," *Journal of Organic Chemistry* (1997), 62(5): 1356-1362.
Gangwar et al., "The effect of conformation on membrane permeability of an acyloxyalkoxy-linked cyclic prodrug of model hexapeptide," *Pharmaceutical Research* (1996), 13(11): 1657-1662.
Gogate et al., "N-(Acyloxyalkoxycarbonyl) derivatives as potential prodrugs of amines. II. Esterase-catalyzed release of parent amines from model prodrugs" *International Journal of Pharmaceutics* (1987), 40(3): 249-55.
Gogate et al., "N-(Acyloxyalkoxycarbonyl) derivatives as potential prodrugs of amines. I. Kinetics and mechanism of degradation in aqueous solutions" *International Journal of Pharmaceutics* (1987), 40(3): 235-48.
Goodson, "Dental Applications" *Medical Applications of Controlled Release* (1984) 2: 115-138.
Gudmundsson et al., "Prodrug strategies to enhance the permeation of opioid peptides through the intestinal mucosa," *Alfred Benzon Symposium* (1998), 43 (Peptide and Protein Drug Delivery), 259-272.
Gudmundsson et al., "The effect of conformation of the acyloxyalkoxy-based cyclic prodrugs of opioid peptides on their membrane permeability," *Journal of Peptide Research* (1999), 53(4): 403-413.
Hashimoto et al., "Acyclic analogs of kainoids: their syntheses and depolarizing activities," *Tetrahedron* (1996), 52(6): 1931-42.
Hashimoto et al., "Syntheses and neuroexcitatory activity of kainoids," *Tennen Yuki Kagobutsu Toronkai Koen Yoshisbu* (1989) 31: 175-82.

Hauske et al., "Synthesis of non-peptide scaffolding domains via a totally stereoselective iodolactonization protocol," *Tetrahedron Letters* (1993), 34(31): 4909-12.

Hennard et al., "Synthesis and Activities of Pyoverdin-Quinolone Adducts: A Prospective Approach to a Specific Therapy Against *Pseudomonas aeruginosa*," *Journal of Medicinal Chemistry* (2001), 44(13): 2139-2151.

Hintermann et al., "Polylithiated β-peptides. Like-selective C-terminal alkylation of Boc-β-HVal-β-Hala-β-HLeu-OMe," *European Journal of Organic Chemistry* (1998), 11: 2379-2387.

Honda et al., "Chiral synthesis of the key intermediate for 1β-methylcarbapenem antibiotics starting from (−)-carvone,"*Journal of the Chemical Society, Perkin Transactions 1: Organic and Bio-Organic Chemistry* (1972-1999) (1991), 12: 3027-32.

Howard et al., "Intracerebral drug delivery in rats with lesion-induced memory deficits," *J. Neurosurg.* (1989) 71:105-112.

Hunter et al., "Single isomer Technetium-99m Tamoxifen Conjugates," *Bioconjugate Chemistry* (2000), 11(2): 175-181.

Hunter et al., "Lysine conjugates for the labeling of peptides with technetium-99m and rhenium," *Journal of Labeled Compounds & Radiopharmaceuticals* (2000), 43(4): 403-412.

Iqbal et al., "Combinatorial synthesis of the peptidomimetic inhibitors of HIV 1 protease. *Indian Journal of Chemistry*, Section A: Inorganic, Bio-inorganic, Physical, Theoretical & Analytical Chemistry" (1997), 36A(6): 498-506.

Jako et al., "Stereoselective synthesis of 3-alkylated glutamic acids: application to the synthesis of secokainic acid," *Journal of Organic Chemistry* (1991), 56(19): 5729-33.

Jezyk et al., "Transport of Pregabalin in Rat Intestine and Caco-2 Monolayers" *Pharm. Res.* (1999) 16:519-526.

Jones et al., "New renin inhibitors containing novel analogs of statine," *Journal of Peptide Research* (1997), 50(2): 109-121.

Kayser et al., "Designer Yeast: an Enatioselective Oxidizing Reagent for Organic Synthesis," *Synlett* (1999) 1:153-158.

Kimura et al., "Synthesis and structure-activity relationships of 7-[3-(1-aminoalkyl)pyrrolidinyl]- and 7-[3-1-aminocycloalkyl)pyrrolidinyl]quinolone antibacterials," *Chemical & Pharmaceutical Bulletin* (1994), 42(7): 1442-54.

Kornyei et al., "Preliminary studies of some $^{99m}$Tc labeled potential myocardial metabolic agents in rabbits," *Radioactive Isotopes in Clinical Medicine and Research*, Proceedings of the International Badgastein Symposium, 22nd, Badgastein,Austria, Jan. 9-12, 1996 (1997), Meeting Date (1996) 417-421.

Kricheldorf, "Reactions with silylazides. 7. Trimethylsilyl 4-isocyanatocarboxylates and 4-aminocarboxylic acid N-carboxylic acid anhydrides," *Makromolekulare Chemie* (1975), 176(1): 57-59.

Langer, "New Methods of Drug Delivery," *Science* (1990) 249: 1527-1533.

Langer et al., "Chemical and physical structure of polymers as carriers for controlled realease of bioactive agents: a review," *JMS—Rev Macromol Chem Phys* (1983), C23(1): 61-126.

Leenders et al., "β-Glucuronyl carbamate based pro-moieties designed for prodrugs in ADEPT," *Tetrahedron Letters* (1995), 36(10): 1701-4.

Leenders et al., "Highly diastereoselective synthesis of anomeric β-O-glycopyranosyl carbamates from isocyanates," *Synthesis* (1996) 11: 1309-1312.

Levy et al., Inhibition of Calcification of Bioprosthetic Heart Valves by Local Controlled-Release Diphosphonate, *Science* (1985) 228: 190-2.

Li et al., "Synthesis of (alkoxycarbonyloxy) methyl, (acyloxy)methyl and (oxodioxolenyl) methyl carbamates as bioreversible prodrug moieties for amines," *Bioorganic and Medicinal Chemistry Letters* (1997), 7(22): 2909-2912.

Lin et al., "Mono and bis double ester prodrugs aminomethyl-THF 1β-methylcarbapenems" *Bioorganic & Medicinal Chemistry Letters* (1997), 7(14): 1811-1816.

Luyt et al., "An $N_2S_2$ Bifunctional Chelator for Technetium-99m and Rhenium: Complexation, Conjugation, and Epimerization to a Single Isomer," *Bioconjugate Chemistry* (1999), 10(3): 470-479.

Mahadevan et al., "Molecular dynamics simulations of conformational behavior of linear RGD peptidomimetics and cyclic prodrugs in aqueous and octane solutions," *Journal of Biomolecular Structure & Dynamics* (2002), 19(5): 775-788.

Mendes et al., "Synthesis, Stability and In Vitro Dermal Evaluation of Aminocarbonyloxymethyl Esters as Prodrugs of Carboxylic Acid Agents," *Bioorganic & Medicinal Chemistry* (2002), 10(3): 809-816.

Mulvihill et al., "Synthesis and application of novel glyoxylate-derived chloroformates," *Synthesis* (2002), (3): 365-370.

Mulvihill et al., "Synthesis of insecticidally active halofenozide [(acyloxy) alkoxy] carbonyl and (acyloxy)alkyl derivatives," *Synthesis* (2002), 1: 53-58.

Mulvihill et al., "Benzaldehyde-derived chloroformates and their application towards the synthesis of methoxyfenozides-N-[(acyloxy)benzyloxy]carbonyl derivatives," *Tetrahedron Letters* (2001), 42(44): 7751-7754.

Neidlein et al., "Pharmacokinetics of 4-oxa-5-exo-(N-methylcarbamoyloxy)tricyclo-[5.2.1.0.$^{2,6endo}$]dec-8-en-3one in the rat," *Arzneimittel-Forschung* (1988), 38(3): 359-63.

Neidlein et al., "Biotransformation of 4-oxa-5-exo-(N-methylcarbamoyloxy)tricyclo-[5.2.1.0.$^{2,6endo}$]dec-8-en-3one in the rat," *Arzneimittel-Forschung* (1988), 38(2): 260-6.

Neidlein et al., "In-vivo and in-vitro studies on synthetic reference compounds for metabolites of 4-oxa-5-exo-[(N-methylcarbamoyl)oxy]tricyclo-[5.2.1.0.$^{2,6endo}$]dec-8-en-3one in the rat," *Archiv der Pharmazie* (Weinheim, Germany) (1988), 321(3): 125-30.

Nikishin et al., "Free-radical addition of N-acetylamines to unsaturated compounds," *Izvestiya Akademii Nauk SSSR, Seriya Khimicheskaya* (1967) 9: 2056-61.

Nishimura et al., "Orally active 1-(cyclohexyloxycarbonyloxy)alkyl ester prodrugs of cefotiam," *Journal of Antibiotics* (1987), 40(1): 81-90.

Ohtake et al., "An efficient synthesis of the side chain intermediate of BO-2502A, a new 1β-methyl carbapenem, via diastereoselective lactamization as a key step," *Tetrahedron* (1998), 54(11): 2423-2432.

Omar et al., "Activated ester-carbamate type redox chemical delivery system for improved specific delivery of dopamine to the brain," *Saudi Pharmaceutical Journal* (1994), 2(1): 32-41.

Omar et al., "Synthesis and evaluation of redox chemical delivery system for brain-enhanced dopamine containing an activated carbamate-type ester," *Journal of Drug Targeting* (1994), 2(4): 309-16.

Pandey et al., "Spirocyclic non-peptide glycoprotein IIb-IIIa antagonists. Part 2: design of potent antagonists containing the 3-azaspiro[5.5]undec-9-yl template," *Bioorganic & Medicinal Chemistry Letters* (2001) 11(10): 1293-1296.

Park et al., "Synthesis of optically active 2-alkyl-3,4-iminobutanoic acids. β-Amino acids containing an aziridine heterocyle," *Journal of Organic Chemistry* (2001), 66(11): 3696-3703.

Pauletti et al., "Esterase-sensitive cyclic prodrugs of peptides: evaluation of an acyloxyalkoxy promoiety in a model hexapeptide," *Pharmaceutical Research* (1996), 13(11): 1615-1623.

Plummer et al., "Stereoslective Michael additions of nitromethane yielding 3R(1S N-substituted aminoethyl)pyrrolidines," *Tetrahedron Letters* (1993), 34(47): 7529-32.

Pop et al., "Novel redox derivatives of tryptophan," *Heterocycles* (1994), 38(9): 2051-64.

Pop et al., "Redox targeting of LY231617, an antioxidant with potential use in the treatment of brain damage," *International Journal of Pharmaceutics* (1996), 140(1): 33-44.

Pring et al., "Use of the 4-methoxybenzyl group for secondary carbamate protection," *Acta Pharmaceutica Suecica* (1986), 23(6): 404-5.

Prokai-Tatrai et al., "Redox derivatives of tranylcypromine: syntheses, properties, and monoamine oxidase inhibitor activity of some chemical delivery systems," *Journal of Pharmaceutical Sciences* (1991), 80(3): 255-61.

Rahmathullah et al., "Prodrugs for Amidines: Synthesis and Anti-*Pneumocystis carinii* Activity of Carbamates of 2,5-Bis(4-amidinophenyl)furan," *Journal of Medicinal Chemistry* (1999), 42(19): 3994-4000.

Reetz et al., "Stereoselective nucleophilic addition reactions of reactive pseudopeptides," *Angewandte Chemie* (1992), 104(12): 1638-41.

Rueping et al., "Folding of β- and γ-peptides—the influence of substitution patterns on the formation of secondary structures," *Peptides: The Wave of the Future*, Proceedings of the Second International and the Seventeenth American Peptide Symposium, San Diego, CA, United States, Jun. 9-14, 2001, 383-384.

Sammis et al., "Highly Enantioselective, Catalytic Conjugate Addition of Cyaninde to α,β-Unsaturated Imides," *Journal of the American Chemical Society* (2003), 125(15): 4442-4443.

Saulnier et al., "An efficient method for the synthesis of guanidino prodrugs," *Bioorganic & Medicinal Chemistry Letters* (1994), 4(16): 1985-90.

Seebach et al., "Preparation and determination of X-ray-crystal and NMR-solution structures of $\gamma^{2,3,4}$-peptides," *Chemical Communications* (Cambridge) (2001), 2: 207-208.

Seebach et al., "$\gamma^2$-, $\gamma^3$-, and $\gamma^{2,3,4}$-amino acids, coupling to γ-hexapeptides: CD spectra, NMR solution and X-ray crystal structures of γ-peptides," *Chemistry—A European Journal* (2002), 8(3): 573-584.

Sefton "Implantable pumps," (1987) *CRC Crit Rev Biomed Eng* 14(3): 201-240.

Smith "Supramolecular dendritic solubilization of a hydrophilic dye and tuning of its optical properties," *Chemical Communications* (Cambridge) (1999), 17: 1685-1686.

Song et al, "Synthesis of a novel cyclic prodrug of RGD peptidomimetic to improve its cell membrane permeation," *Bioorganic Chemistry* (2002), 30(4): 285-301.

Stark et al., "Enzyme-catalyzed prodrug approaches for the histamine H₃-receptor agonist (R)-αmethylhustamine," *Bioorganic & Medicinal Chemistry* (2001), 9(1): 191-198.

Stevenson et al., "Colonic absorption of antiepileptic agents," (1997) *Epilepsia* 38(1): 63-7.

Stratford et al., "Synthesis of aminomethyl-substituted cyclic imide derivatives for evaluation as anticonvulsants," *Journal of Medicinal Chemistry* (1983), 26(10): 1463-9.

Sun et al., "Prodrugs of 3-amido bearing pseudomycin analogues: novel antifungal agents," *Bioorganic & Medicinal Chemistry Letters* (2001), 11(14): 1881-1884.

Sun et al., "Synthesis and evaluation of novel pseudomycin side-chain analogues. Part 3," *Bioorganic & Medicinal Chemistry Letters* (2001), 11(23): 3055-3059.

Tang et al., "Characterization of the efflux transporter(s) responsible for restricting intestinal mucosa permeation of an acyloxyalkoxy-based cyclic prodrug of the opioid peptides DADLE," *Pharmaceutical Research* (2002), 19(6): 780-786.

Verma et al., "Osmotically controlled oral drug delivery," *Drug Develop. Indus. Pharm.* (2000), 26(7): 695-708.

Vrudhula et al., "Cephalosporin prodrugs of paclitaxel for immunologically specific activation by L-49-sFv-β-Lactamase fusion protein," *Bioorganic & Medicinal Chemistry Letters* (2003), 13(3): 539-542.

Williams et al., "The integration of SPR biosensors with mass spectrometry: possible applications for proteome analysis," *Tibtech* (2000), 18:45-48.

Xu et al., "Advances in research and bioactivities of compounds containing di-tert-butylphenol," *Yaoxue Xuebao* (2001), 36(11):877-880.

Yanagida et al., "Syntheses of acyclic analogs of kainoids and neuroexcitatory activity," *Tetrahedron Letters* (1989), 30(29): 3799-802.

Yang et al., "In vitro stability and in vivo pharmacokinetic studies of a model opioid peptide, H-Try-$_D$-Ala-Gly-Phe-$_D$-Leu-OH (DADLE), and its cyclic prodrugs," *Journal of Pharmacology and Experimental Therapeutics* (2002), 303(2): 840-848.

Zhu et al., Phosphate prodrugs of PD 154075, *Bioorganic & Medicinal Chemistry Letters* (2000), 10(10): 1121-1124.

PRODRUGS OF GABA ANALOGS, COMPOSITIONS AND USES THEREOF

This application is a continuation-in-part of U.S. patent application Ser. No. 10/171,485, filed Jun. 11, 2002, now U.S. Pat. No. 6,818,787, which claims the benefit under 35 U.S.C. § 119(e) of U.S. Provisional Application Ser. No. 60/297,521 filed Jun. 11, 2001; U.S. Provisional Application Ser. No. 60/298,514 filed Jun. 14, 2001; and U.S. Provisional Application Ser. No. 60/366,090 filed Mar. 19, 2002. The above applications are herein incorporated by reference in their entirety.

1. FIELD OF THE INVENTION

The present invention relates generally to prodrugs of GABA analogs, pharmaceutical compositions of prodrugs of GABA analogs, methods of making prodrugs of GABA analogs and methods of using prodrugs of GABA analogs and pharmaceutical compositions of prodrugs of GABA analogs. More particularly, the present invention relates to prodrugs of gabapentin and pregabalin, pharmaceutical compositions of prodrugs of gabapentin and pregabalin, methods of making prodrugs of gabapentin and pregabalin, methods of using prodrugs of gabapentin and pregabalin and pharmaceutical compositions of prodrugs of gabapentin and pregabalin.

2. BACKGROUND OF THE INVENTION

Gamma ("γ")-aminobutyric acid ("GABA") is one of the major inhibitory transmitters in the central nervous system of mammals. GABA is not transported efficiently into the brain from the bloodstream (i.e., GABA does not effectively cross the blood-brain barrier). Consequently, brain cells provide virtually all of the GABA found in the brain (GABA is biosynthesized by decarboxylation of glutamic acid with pyridoxal phosphate).

GABA regulates neuronal excitability through binding to specific membrane proteins (i.e., GABAA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., multiple sclerosis, action tremors, tardive dyskinesia), panic, anxiety, depression, alcoholism and manic behavior.

The implication of low GABA levels in a number of common disease states and/or common medical disorders has stimulated intensive interest in preparing GABA analogs, which have superior pharmaceutical properties in comparison to GABA (e.g., the ability to cross the blood brain barrier). Accordingly, a number of GABA analogs, with considerable pharmaceutical activity have been synthesized in the art (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Belliotti et al., International Publication No. WO 00/31020; Bryans et al., International Publication No. WO 00/50027; and Bryans et al., International Publication No. WO 02/00209).

Pharmaceutically important GABA analogs include, for example, gabapentin (1), pregabalin (2), vigabatrin (3), and baclofen (4) shown above. Gabapentin is a lipophilic GABA analog that can pass through the blood-brain barrier, which has been used to clinically treat epilepsy since 1994. Gabapentin also has potentially useful therapeutic effects in chronic pain states (e.g., neuropathic pain, muscular and skeletal pain), psychiatric disorders (e.g., panic, anxiety, depression, alcoholism and manic behavior), movement disorders (e.g., multiple sclerosis, action tremors, tardive dyskinesia), etc. (Magnus, *Epilepsia*, 1999, 40:S66–S72). Currently, gabapentin is also used in the clinical management of neuropathic pain. Pregabalin, which possesses greater potency in pre-clinical models of pain and epilepsy than gabapentin is presently in Phase III clinical trials.

A significant problem with many GABA analogs is intramolecular reaction of the γ amino group with the carboxyl functionality to form the γ-lactam, as exemplified for gabapentin below. Formation of γ-lactam (5) presents serious difficulties in formulating gabapentin because of its toxicity. For example, gabapentin has a toxicity ($LD_{50}$, mouse) of more than 8000 mg/kg, while the corresponding lactam (5) has a toxicity ($LD_{50}$, mouse) of 300 mg/kg. Consequently, formation of side products such as lactams during synthesis of GABA analogs and/or formulation and/or storage of GABA analogs or compositions of GABA analogs must

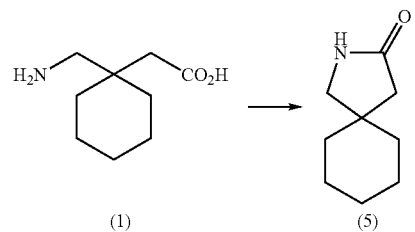

be minimized for safety reasons (particularly, in the case of gabapentin).

The problem of lactam contamination of GABA analogs, particularly in the case of gabapentin, has been partially overcome through use of special additional purification steps, precise choice of adjuvant materials in pharmaceutical compositions and careful control procedures (Augurt et al., U.S. Pat. No. 6,054,482). However, attempts to prevent lactam contamination have not been entirely successful, in either synthesis or storage of GABA analogs such as gabapentin or compositions thereof.

Rapid systemic clearance is another significant problem with many GABA analogs including gabapentin, which consequently require frequent dosing to maintain a therapeutic or prophylactic concentration in the systemic circulation (Bryans et al., *Med. Res. Rev.*, 1999, 19, 149–177). For example, dosing regimens of 300–600 mg doses of gabapentin administered three times per day are typically used for anticonvulsive therapy. Higher doses (1800–3600 mg/d in divided doses) are typically used for the treatment of neuropathic pain states.

Sustained released formulations are a conventional solution to the problem of rapid systemic clearance, as is well known to those of skill in the art (See, e.g., "Remington's Pharmaceutical Sciences," Philadelphia College of Pharmacy and Science, 17th Edition, 1985). Osmotic delivery systems are also recognized methods for sustained drug delivery (See, e.g., Verma et al., *Drug Dev. Ind. Pharm.*, 2000, 26:695–708). Many GABA analogs, including gabapentin and pregabalin, are not absorbed via the large intestine. Rather, these compounds are typically absorbed in the small intestine by the large neutral amino acid transporter ("LNAA") (Jezyk et al, *Pharm. Res.*, 1999, 16, 519–526). The rapid passage of conventional dosage forms through the proximal absorptive region of the gastrointestinal tract has prevented the successful application of sustained release technologies to many GABA analogs.

Thus, there is a significant need for effective sustained release versions of GABA analogs to minimize increased dosing frequency due to rapid systemic clearance of these compounds. There is also a need for pure GABA analogs, (particularly gabapentin and pregablin analogs) which are substantially pure and do not spontaneously lactamize during either formulation or storage.

3. SUMMARY OF THE INVENTION

The present invention addresses these and other needs by providing prodrugs of GABA analogs, pharmaceutical compositions of prodrugs of GABA analogs and methods for making prodrugs of GABA analogs. The present invention also provides methods for using prodrugs of GABA analogs, and methods for using pharmaceutical compositions of prodrugs of GABA analogs for treating or preventing common diseases and/or disorders.

Importantly, the prodrugs provided by the present invention may possess significant pharmaceutical advantages of particular use in medicine. First, the promoiety of the prodrugs of GABA analogs provided by the current invention are typically labile in vivo (i.e., cleaved by either enzymatic or chemical means to generate substantial quantities of a GABA analog before the prodrug is cleared from a patient. Second, the promoiety derivative provided by cleavage of the promoiety from the prodrug and any metabolite thereof, is typically non-toxic when administered to a mammal in accordance with dosing regimens typically followed with the GABA analog.

The compounds of the instant invention have a promoiety attached to the γ amino group of GABA analogs. This promoiety may be directly attached to the γ amino group of a GABA analog or optionally may be attached to the amino group of an α-amino acid promoiety, or to the hydroxy group of an α-hydroxy acid promoiety, which itself is attached to the γ amino group of the GABA analog.

The compounds of the invention may also have a promoiety attached to the carboxyl group of GABA analogs. The carboxyl promoiety will typically be an ester or thioester group. A wide variety of ester or thioester groups may be used to form carboxyl promoieties.

Accordingly, the compounds of the invention may include as many as four promoieties, including one carboxyl promoiety and up to three amino promoieties attached in sequence to the γ amino group (i.e., such that each promoiety is sequentially cleaved from the N-terminal end of the GABA analog). The compounds of the invention may contain two amino promoieties and one carboxyl promoiety, two amino promoieties, one amino promoiety and one carboxyl promoiety or one amino promoiety. Preferably, in those compounds of the invention which contain both an amino promoiety and a carboxyl promoiety, the carboxyl promoiety is hydrolyzed prior to the complete cleavage of the promoiety (ies) attached to the amine group.

In a first aspect, the present invention provides compounds of Formula (I), Formula (II) or Formula (III):

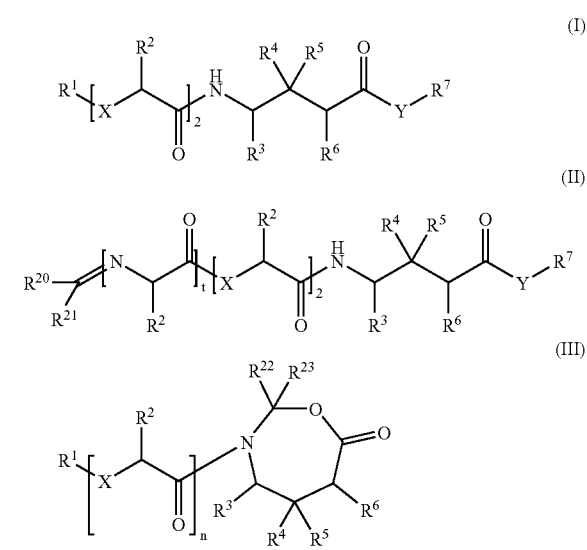

or a pharmaceutically acceptable salt, hydrate or solvate thereof, wherein:

m, n, t and u are independently 0 or 1;

X is O or $NR^{16}$;

W is O or $NR^{17}$;

Y is O or S;

$R^1$ is selected from the group consisting of hydrogen, $R^{24}C(O)$—, $R^{25}OC(O)$—, $R^{24}C(S)$—, $R^{25}OC(S)$—, $R^{25}SC(O)$—, $R^{25}SC(S)$—, $(R^9O)(R^{10}O)P(O)$—, $R^{25}S$—,

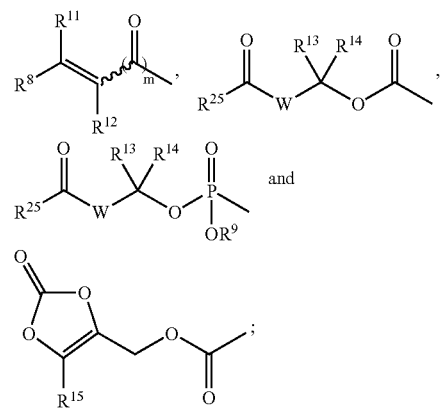

each $R^2$ is independently selected from the group consisting of hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy or optionally, $R^2$ and $R^{16}$ together with the atoms to which they are bonded form a cycloheteroalkyl or substituted cycloheteroalkyl ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl or optionally, $R^4$ and $R^5$ together with the carbon atom to which they are bonded form a cycloalkyl, substituted cycloalkyl, cycloheteroalkyl, substituted cycloheteroalkyl or bridged cycloalkyl ring;

$R^8$ and $R^{12}$ are independently selected from the group consisting of hydrogen, acyl, substituted acyl, alkoxycarbonyl, substituted alkoxycarbonyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl, or optionally $R^8$ and $R^{12}$ together with the carbon atoms to which they are bonded form a cycloalkyl, substituted cycloalkyl, cycloheteroalkyl or substituted cycloheteroalkyl ring;

$R^{11}$ is selected from the group consisting of hydrogen, alkyl, substituted alkyl, acyl, substituted acyl, aryl, substituted aryl, arylalkyl, substituted arylalkyl, carbamoyl, substituted carbamoyl, cyano, cycloalkyl, substituted cycloalkyl, heterocycloalkyl, substituted heterocycloalkyl, heteroaryl, substituted heteroaryl, heteroarylalkyl, substituted heteroarylalkyl, alkoxycarbonyl, substituted alkoxycarbonyl, cycloheteroalkyloxycarbonyl, substituted cycloheteroalkyloxycarbonyl, aryloxycarbonyl, substituted aryloxycarbonyl, heteroaryloxycarbonyl, substituted heteroaryloxycarbonyl and nitro;

$R^7$, $R^9$, $R^{10}$, $R^{15}$, $R^{16}$ and $R^{17}$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{13}$ and $R^{14}$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl or optionally, $R^{13}$ and $R^{14}$ together with the carbon atom to which they are bonded form a cycloalkyl, substituted cycloalkyl, cycloheteroalkyl or substituted cycloheteroalkyl ring;

$R^{20}$ and $R^{21}$ are independently selected from the group consisting of hydrogen, acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl or optionally $R^{20}$ and $R^{21}$ together with the carbon atom to which they are bonded form a cycloalkyl, substituted cycloalkyl, cycloheteroalkyl or substituted cycloheteroalkyl ring;

$R^{22}$ and $R^{23}$ are independently selected from the group consisting of hydrogen, alkyl, substituted alkyl, aryl, substituted aryl, arylalkyl and substituted arylalkyl or optionally, $R^{22}$ and $R^{23}$ together with the carbon atom to which they are bonded form a cycloalkyl, substituted cycloalkyl, cycloheteroalkyl or substituted cycloheteroalkyl ring;

$R^{24}$ is selected from the group consisting of hydrogen, acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{25}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

In a second aspect, the present invention provides pharmaceutical compositions of compounds of the invention. The pharmaceutical compositions generally comprise one or more compounds of the invention, and a pharmaceutically acceptable vehicle.

In a third aspect, the present invention provides methods for treating or preventing epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. The methods generally involve administering to a patient in need of such treatment or prevention a therapeutically effective amount of a compound of the invention.

In a fourth aspect, the current invention provides pharmaceutical compositions for treating or preventing epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome in a patient in need of such treatment or prevention. The methods generally involve administering to a patient in need of such treatment or prevention a therapeutically effective amount of a pharmaceutical composition of the invention.

In a fifth aspect, the invention comprises a GABA analog derivative compound, M-G, for administration to a patient in need of therapy, wherein M is a promoiety and G is derived from a GABA analog, H-G (where H is hydrogen). The promoiety M, once cleaved from G, and any metabolite thereof, exhibits a carcinogenically toxic dose ($TD_{50}$) in rats of greater than 0.2 mmol/kg/day. Further, the promoiety M cleaves from G at a sufficient rate in vivo, upon colonic administration to rats, to produce:

(i) a maximum concentration of H-G in plasma ($C_{max}$) of at least 120% of the $C_{max}$ of H-G in plasma is achieved by colonically administering an equimolar dose of H-G; and (ii) an AUC that is at least 120% of the AUC is achieved by colonically administering an equimolar dose of H-G.

Preferably, M-G is a derivative of Formula (XIV):

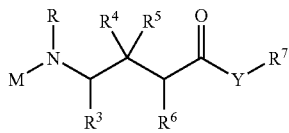

(XIV)

or a pharmaceutically acceptable salt, hydrate or solvate thereof, wherein:

R is hydrogen or R and $R^6$ together with the atoms to which they are bonded form an azetidine, substituted azetidine, pyrrolidine or substituted pyrrolidine ring; and Y, $R^3$, $R^4$, $R^5$, $R^6$ and $R^7$ are as previously defined.

Most preferably, M is a derivative of Formula (XV):

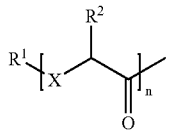

(XV)

wherein:

n, X, $R^1$ and $R^2$ are as previously defined.

4. DETAILED DESCRIPTION OF THE INVENTION

4.1 Definitions

"Active transport or active transport process" refers to the movement of molecules across cellular membranes that:

a) is directly or indirectly dependent on an energy mediated process (i.e., driven by ATP hydrolysis, ion gradient, etc.);

or b) occurs by facilitated diffusion mediated by interaction with specific transporter proteins.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

"Acylamino" by itself or as part of another substituent refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylcarbonylamino and the like.

"Alkylamino" by itself or as part of another substituent means a radical —NHR where R represents an alkyl or cycloalkyl group as defined herein. Representative examples include, but are not limited to, methylamino, ethylamino, 1-methylethylamino, cyclohexyl amino and the like.

"Alkoxy" by itself or as part of another substituent refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)-alkoxy where alkoxy is as defined herein.

"Alkylsulfonyl" by itself or as part of another substituent refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" by itself or as part of another substituent refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" by itself or as part of another substituent refers to a radical —SR where R is an alkyl or cycloalkyl group as defined herein that may be optionally substituted as defined herein. Representative examples include, but are not limited to methylthio, ethylthio, propylthio, butylthio and the like.

"Aryl" by itself or as part of another substituent refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably between 6 to 12 carbon atoms.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$–C$_{30}$) arylalkyl, e.g., the alkanyl, alkenyl or alkynyl moiety of the arylalkyl group is (C$_1$–C$_{10}$) and the aryl moiety is (C$_6$–C$_{20}$), more preferably, an arylalkyl group is (C$_6$–C$_{20}$) arylalkyl, e.g., the alkanyl, alkenyl or alkynyl moiety of the arylalkyl group is (C$_1$–C$_8$) and the aryl moiety is (C$_6$–C$_{12}$).

"Arylalkyloxy" by itself or as part of another substituent refers to an —O-arylalkyl group where arylalkyl is as defined herein.

"Aryloxycarbonyl" by itself or as part of another substituent refers to a radical —C(O)—O-aryl where aryl is as defined herein.

"AUC" is the area under the plasma drug concentration-versus-time curve extrapolated from zero time to infinity.

"Bridged cycloalkyl" by itself or as part of another substituent refers to a radical selected from the group consisting of

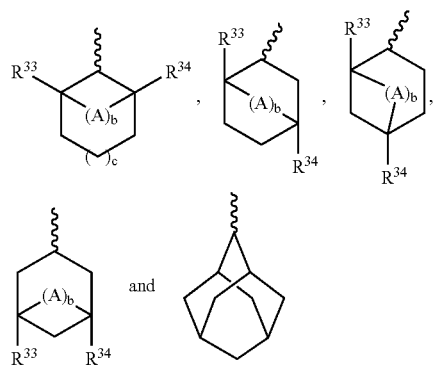

wherein:
A is (CR$^{35}$R$^{36}$)$_b$;
R$^{35}$ and R$^{36}$ are independently selected from the group consisting of hydrogen and methyl;
R$^{33}$ and R$^{34}$ are independently selected from the group consisting of hydrogen and methyl;
b is an integer from 1 to 4; and
c is an integer from 0 to 2.

"Carbamoyl" by itself or as part of another substituent refers to the radical —C(O)N(R)$_2$ where each R group is independently hydrogen, alkyl, cycloalkyl or aryl as defined herein.

"Carcinogenic potency (TD$_{50}$)" (see Peto et al., *Environmental Health Perspectives* 1984, 58, 1–8) is defined for a particular compound in a given animal species as that chronic dose-rate in mg/kg body wt/day which would induce tumors in half the test animals at the end of a standard lifespan for the species. Since the tumor(s) of interest often does occur in control animals, TD$_{50}$ is more precisely defined as: that dose-rate in mg/kg body wt/day which, if administered chronically for the standard lifespan of the species, will halve the probability of remaining tumorless throughout that period. A TD$_{50}$ can be computed for any particular type of neoplasm, for any particular tissue, or for any combination of these.

"C$_{max}$" is the highest drug concentration observed in plasma following an extravascular dose of drug.

"Compounds of the invention" refers to compounds encompassed by generic formulae disclosed herein and includes any specific compounds within that formula whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention. Further, it should be understood, when partial structures of the compounds of the invention are illustrated, that brackets indicate the point of attachment of the partial structure to the rest of the molecule.

"Composition of the invention" refers to at least one compound of the invention and a pharmaceutically acceptable vehicle, with which the compound is administered to a patient.

"Cyano" means the radical —CN.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is ($C_3$–$C_{10}$) cycloalkyl, more preferably ($C_3$–$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" by itself or as part of another substituent refers to a radical —C(O)—OR where R is cycloheteroalkyl is as defined herein.

"Derived from a bile acid" refers to a moiety that is structurally related to a compound of Formulae (XVII) or (XVIII):

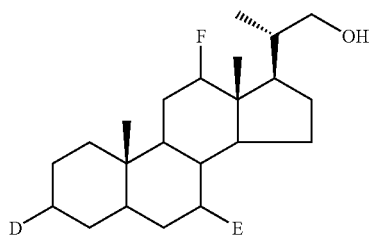

(XVII)

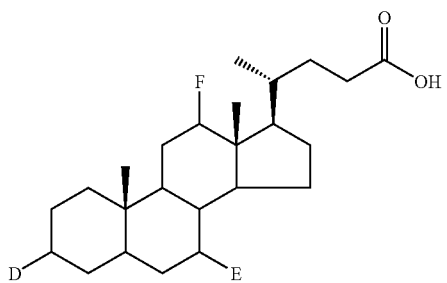

(XVIII)

wherein each of D, E and F are independently H or OH.

The structure of the moiety is identical to the compounds above except at 1 or 2 positions. At these positions, a hydrogen atom attached to a hydroxyl group and/or the hydroxyl moiety of the carboxylic acid group has been replaced with a covalent bond that serves as a point of attachment to another moiety, which is preferably a GABA analog or GABA analog derivative.

"Derived from a GABA analog" refers to a moiety that is structurally related to a GABA analog. The structure of the moiety is identical to the compound except at 1 or 2 positions. At these positions, a hydrogen atom attached to the amino group, and (optionally) the hydroxyl moiety of the carboxylic acid group has been replaced with a covalent bond that serves as a point of attachment to another moiety.

"Dialkylamino" by itself or as part of another substituent means a radical —NRR' where R and R' independently represent an alkyl or cycloalkyl group as defined herein. Representative examples include, but are not limited to, dimethylamino, methylethylamino, di-(1-methylethyl) amino, (cyclohexyl)(methyl)amino, (cyclohexyl)(ethyl) amino, (cyclohexyl)(propyl)amino and the like.

"GABA analog" refers to a compound, unless specified otherwise, as having the following structure:

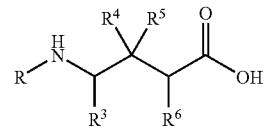

wherein:

R is hydrogen, or R and $R^6$ together with the atoms to which they are attached form an azetidine, substituted azetidine, pyrrolidine or substituted pyrrolidine ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl; and $R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are bonded form a cycloalkyl, substituted cycloalkyl, cycloheteroalkyl, substituted cycloheteroalkyl or bridged cycloalkyl ring.

"Halo" by itself or as part of another substituent means fluoro, chloro, bromo, or iodo.

"Heteroalkyloxy" by itself or as part of another substituent means an —O-heteroalkyl group where heteroalkyl is as defined herein.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5–20 membered heteroaryl, more preferably, between 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroaryloxycarbonyl" by itself or as part of another substituent refers to a radical —C(O)—OR where R is heteroaryl as defined herein.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Passive diffusion" refers to uptake of an agent that is not mediated by a specific transporter protein. An agent that is substantially incapable of passive diffusion has a permeability across a standard cell monolayer (e.g., Caco-2) in vitro of less than $5\times10^{-6}$ cm/sec, and usually less than $1\times10^{-6}$ cm/sec (in the absence of an efflux mechanism).

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —R$^{29}$, —O$^-$, =O, —OR$^{29}$, —SR$^{29}$, —S$^-$, =S, —NR$^{29}$R$^{30}$, =NR$^{29}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{29}$, —OS(O)$_2$O$^-$, —OS(O)$_2$R$^{29}$, —P(O)(O$^-$)$_2$, —P(O)(OR$^{29}$)(O$^-$), —OP(O)(OR$^{29}$)(OR$^{30}$), —C(O)R$^{29}$, —C(S)R$^{29}$, —C(O)OR$^{29}$, —C(O)NR$^{29}$R$^{30}$, —C(O)O$^-$, —C(S)OR$^{29}$, —NR$^{31}$C(O)NR$^{29}$R$^{30}$, —NR$^{31}$C(S)NR$^{29}$R$^{30}$, —NR$^{31}$C(NR$^{29}$)NR$^{29}$R$^{30}$ and —C(NR$^{29}$)NR$^{29}$R$^{30}$, where each X is independently a halogen; each R$^{29}$ and R$^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{31}$R$^{32}$, —C(O)R$^{31}$ or —S(O)$_2$R$^{31}$ or optionally R$^{29}$ and R$^{30}$ together with the atom to which they are both bonded form a cycloheteroalkyl or substituted cycloheteroalkyl ring; and R$^{31}$ and R$^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Transporter protein" refers to a protein that has a direct or indirect role in transporting a molecule into and/or through a cell. For example, a transporter protein may be, but is not limited to, solute carrier transporters, co-transporters, counter transporters, uniporters, symporters, antiporters, pumps, equilibrative transporters, concentrative transporters and other proteins, which mediate active transport, energy-dependent transport, facilitated diffusion, exchange mechanisms and specific absorption mechanisms. Transporter proteins, may also be, but are not limited to, membrane-bound proteins that recognize a substrate and effect its entry into or exit from a cell by a carrier-mediated transporter or by receptor-mediated transport. A transporter protein, may also be, but is not limited to, an intracellularly expressed protein that participates in trafficking of substrates through or out of a cell. Transporter proteins, may also be, but are not limited to, proteins or glycoproteins exposed on the surface of a cell that do not directly transport a substrate but bind to the substrate holding it in proximity to a receptor or transporter protein that effects entry of the substrate into or through the cell. Examples of carrier proteins include: the intestinal and liver bile acid transporters, dipeptide transporters, oligopeptide transporters, simple sugar transporters (e.g., SGLT1), phosphate transporters, monocarboxylic acid transporters, P-glycoprotein transporters, organic anion transporters (OAT), and organic cation transporters. Examples of receptor-mediated transport proteins include: viral receptors, immunoglobulin receptors, bacterial toxin receptors, plant lectin receptors, bacterial adhesion receptors, vitamin transporters and cytokine growth factor receptors.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

4.2 The Compounds of the Invention

Those of skill in the art will appreciate that compounds of Formulae (I), (II) and (III) share certain structural features in common. These compounds are all GABA analogs (i.e., γ-aminobutyric acid derivatives) to which promoieties have been attached. In particular, R$^2$, R$^3$, R$^4$, R$^5$, R$^6$, X and Y are common substituents found in compounds of Formulae (I), (II) and (III).

The compounds of the invention include compounds of Formula (I), Formula (II) or Formula (III):

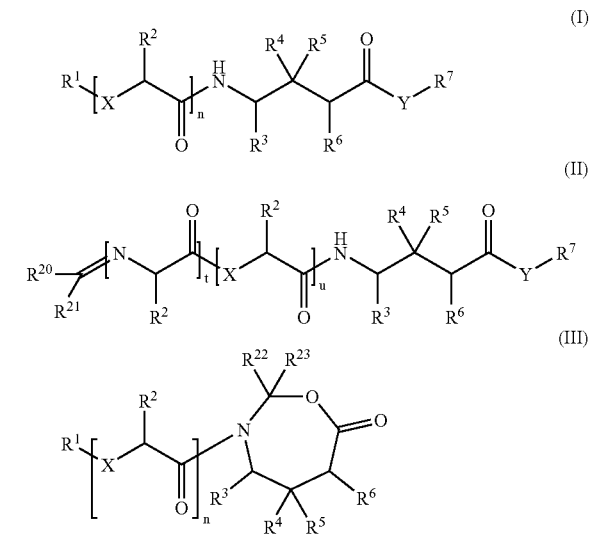

or a pharmaceutically acceptable salt, hydrate or solvate thereof, wherein:

n, t, u, X, Y, R$^1$, R$^2$, R$^3$, R$^4$, R$^5$, R$^6$, R$^7$, R$^{20}$, R$^{21}$, R$^{22}$ and R$^{23}$ are as previously defined above.

In a preferred embodiment, compounds of Formulae (I), (II) and (III) do not include the following compounds:

when R$^3$ and R$^6$ are both hydrogen, then R$^4$ and R$^5$ are not both hydrogen nor both methyl;

in a compound of Formula (I) when either n is 0 or when n is 1 and X is NR$^{16}$, then R$^1$ is not hydrogen;

in a compound of Formula (I) neither R$^1$, R$^7$O—, R$^{24}$C(O)—, R$^{25}$C(O)— nor R$^{25}$O— is a moiety derived from a bile acid;

in a compound of Formula (I) when R$^1$ is R$^{24}$C(O)— and n is 0, then R$^{24}$ is not methyl, tert-butyl, 2-aminoethyl, 3-aminopropyl, benzyl, phenyl or 2-(benzoyloxymethyl)phenyl;

in a compound of Formula (I) when R$^1$ is R$^{25}$OC(O)—, then R$^{25}$ is not R$^{26}$C(O)CR$^{13}$R$^{14}$—, wherein R$^{26}$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

in a compound of Formula (I) when $R^1$ is $R^{25}OC(O)$— and n is 0, then $R^{25}$ is not methyl, tert-butyl or benzyl;

in a compound of Formula (I) when n is 0 and $R^1$ is $R^{25}C(O)OCR^{13}R^{14}OC(O)$— then if either $R^{13}$ or $R^{14}$ is hydrogen, alkoxycarbonyl, substituted alkoxycarbonyl, carbamoyl, cycloalkoxycarbonyl or substituted cycloalkoxycarbonyl, the other of $R^{13}$ or $R^{14}$ is not hydrogen;

in a compound of Formula (I) when n is 1, X is NH, $R^3$, $R^5$ and $R^6$ are each hydrogen, and $R^4$ is cyclohexyl, then $R^2$ is not benzyl;

in a compound of Formula (II) when t is 1, u is 0, then neither $R^{20}$ nor $R^{21}$ is 2-hydroxy-3-methyl-5-chlorophenyl; and in a compound of Formula (II) when u is 1 and X is O, then t is 1.

In one embodiment of compounds of Formulae (I), (II) and (III), when $R^3$ and $R^6$ are each hydrogen, then $R^4$ and $R^5$ are neither both hydrogen nor both methyl. In another embodiment of compounds of Formula (I), when either n is 0 or when n is 1 and X is $NR^{16}$, then $R^1$ is not hydrogen. In still another embodiment, of compounds of Formula (I), neither $R^1$, $R^7O$—, $R^{24}C(O)$—, $R^{25}C(O)$— nor $R^{25}O$— is a moiety derived from a bile acid. In still another embodiment of compounds of Formula (I), when $R^1$ is $R^{24}C(O)$— and n is 0, then $R^{24}$ is not alkyl, substituted alkyl, arylalkyl, aryl or substituted aryl. In still another embodiment of compounds of Formula (I), when $R^1$ is $R^{24}C(O)$— and n is 0, then $R^{24}$ is not $C_{1-4}$ alkanyl, benzyl, phenyl or substituted phenyl. In still another embodiment of compounds of Formula (I), when $R^1$ is $R^{24}C(O)$— and n is 0, then $R^{24}$ is not methyl, tert-butyl, 2-aminoethyl, 3-aminopropyl, benzyl, phenyl or 2-(benzoyloxymethyl)-phenyl. In still another embodiment of compounds of Formula (I) when $R^1$ is $R^{25}OC(O)$—, then $R^{25}$ is not $R^{26}C(O)CR^{13}R^{14}$—. In still another embodiment of compounds of Formula (I) when $R^1$ is $R^{25}OC(O)$— and n is 0, then $R^{25}$ is not alkyl or arylalkyl. In still another embodiment of compounds of Formula (I) when $R^1$ is $R^{25}OC(O)$— and n is 0, then $R^{25}$ is not $C_{1-4}$ alkanyl or benzyl. In still another embodiment of compounds of Formula (I) when $R^1$ is $R^{25}OC(O)$— and n is 0, then $R^{25}$ is not methyl, tert-butyl or benzyl. In still another embodiment of compounds of Formula (I) when n is 0 and $R^1$ is $R^{25}C(O)OCR^{13}R^{14}OC(O)$— then if either $R^{13}$ or $R^{14}$ is hydrogen, alkoxycarbonyl, substituted alkoxycarbonyl, carbamoyl, cycloalkoxycarbonyl or substituted cycloalkoxycarbonyl, the other of $R^{13}$ or $R^{14}$ is not hydrogen. In still another embodiment of compounds of Formula (I) when $R^3$, $R^5$ and $R^6$ are each hydrogen, then $R^4$ is not cyclohexyl. In still another embodiment of compounds of Formula (I) when n is 1, X is NH, $R^3$, $R^5$, $R^6$ are each hydrogen and $R^2$ is benzyl, then $R^4$ is not cyclohexyl.

In one embodiment of compounds of Formula (II), neither $R^{20}$ nor $R^{21}$ is 2-hydroxy-3-methyl-5-chlorophenyl. In one embodiment of compounds of Formula (II), when u is 1 and X is O, then t is 1.

In one embodiment of compounds of Formulae, (I) (II) and (III), n is 0. In another embodiment, n is 1. When n is 1, and X is $NR^{16}$, preferably the α-amino acid is of the L-stereochemical configuration.

In another embodiment of compounds of Formulae (I) and (II), $R^7$ is selected from the group consisting of hydrogen, alkyl, substituted alkyl, aryl, substituted aryl, arylalkanyl, substituted arylalkanyl, cycloalkanyl, substituted cycloalkanyl, cycloheteroalkanyl and substituted cycloheteroalkanyl.

In a preferred embodiment, Y is O and $R^7$ is hydrogen. In still another embodiment, Y is O and $R^7$ is alkanyl, substituted alkanyl, alkenyl, substituted alkenyl, aryl or substituted aryl. Preferably, $R^7$ is methyl, ethyl, benzyl, —C(CH$_3$)═CH$_2$, —CH$_2$C(O)N(CH$_3$)$_2$,

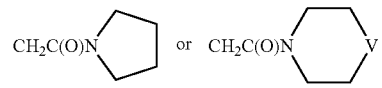

where V is O or CH$_2$.

In one preferred embodiment of compounds of Formulae (I), (II) and (III), $R^2$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl. Preferably, $R^2$ is selected from the group consisting hydrogen, alkanyl, substituted alkanyl, aryl, substituted aryl, arylalkanyl, substituted arylalkanyl, cycloalkanyl, heteroarylalkyl and substituted heteroarylalkanyl.

In another embodiment compounds of Formulae (I), (II) and (III), X is NH and $R^2$ is hydrogen, cycloalkanyl or alkanyl. Preferably, $R^2$ is hydrogen, methyl, isopropyl, isobutyl, sec-butyl, t-butyl, cyclopentyl or cyclohexyl. In another embodiment, X is NH and $R^2$ is substituted alkanyl. Preferably, $R^2$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In still another embodiment, X is NH and $R^2$ is selected from the group consisting of aryl, arylalkanyl, substituted arylalkanyl and heteroarylalkanyl. Preferably, $R^2$ is phenyl, benzyl, 4-hydroxybenzyl, 4-bromobenzyl, 2-imidazolyl, 4-imidazolylmethyl, 3-indolylmethyl or 2-indolyl. In yet another embodiment, X is $NR^{16}$ and $R^2$ and $R^{16}$ together with the atoms to which they are attached form a cycloheteroalkyl or substituted cycloheteroalkyl ring. Preferably $R^2$ and $R^{16}$ together with the atoms to which they are attached form an azetidine, pyrrolidine or piperidine ring.

In still another embodiment of compounds of Formulae (I), (II) and (III), $R^3$ is hydrogen. In still another embodiment, $R^6$ is hydrogen. In yet another embodiment, $R^3$ and $R^6$ are independently selected from the group consisting of hydrogen, alkyl, substituted alkyl, aryl, substituted aryl, cycloalkyl and substituted cycloalkyl. Preferably, $R^3$ and $R^6$ are independently selected from the group consisting of hydrogen and alkanyl. More preferably, $R^3$ is hydrogen or alkanyl and $R^6$ is hydrogen.

In still another preferred embodiment of compounds of Formulae (I), (II) and (III), $R^4$ and $R^5$ are independently selected from the group consisting of hydrogen, alkyl, substituted alkyl, cycloalkyl, substituted cycloalkyl, cycloheteroalkyl and substituted cycloheteroalkyl. Preferably, $R^4$ and $R^5$ are independently selected from the group consisting of hydrogen, alkanyl and substituted alkanyl.

In another embodiment of compounds of Formulae (I), (II) and (III), $R^4$ and $R^5$ together with the carbon atom to which they are attached form a cycloalkanyl or substituted cycloalkanyl ring. Preferably, $R^4$ and $R^5$ together with the carbon atom to which they are attached form a cyclobutyl, substituted cyclobutyl, cyclopentyl, substituted cyclopentyl, cyclohexyl or substituted cyclohexyl ring. In another embodiment, $R^4$ and $R^5$ together with the carbon atom to which they are attached form a cycloheteroalkyl or substituted cycloheteroalkyl ring. In still another embodiment, $R^4$ and $R^5$ together with the carbon atom to which they are attached form a bridged cycloalkyl ring.

In one embodiment of compounds of Formula (I), n is 1, $R^1$ is $R^{24}C(O)$— or $R^{24}C(S)$— and $R^{24}$ is alkyl, substituted alkyl, heteroalkyl, substituted heteroalkyl, aryl, substituted aryl, heteroaryl or substituted heteroaryl. Preferably, $R^{24}$ is methyl, ethyl, 2-propyl, t-butyl, —CH$_2$OCH(CH$_3$)$_2$, phenyl or 3-pyridyl.

In another embodiment of compounds of Formula (I), n is 1, $R^1$ is $R^{25}OC(O)$— or $R^{25}SC(O)$— and $R^{25}$ is alkyl, substituted alkyl, heteroalkyl, aryl, substituted aryl, heteroaryl or substituted heteroaryl. Preferably, $R^{25}$ is ethyl, 2-propyl, neopentyl, —CH$_2$OCH(CH$_3$)$_2$, phenyl or 2-pyridyl.

One preferred embodiment of compounds of Formula (I) includes compounds of Formula (IV):

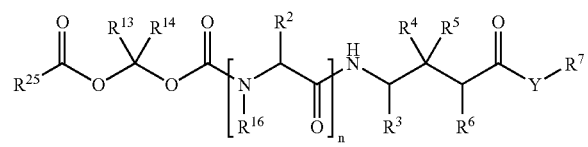

(IV)

or a pharmaceutically acceptable salt, hydrate or solvate thereof, wherein:

n, Y, $R^2$, $R^3$, $R^4$, $R^5$, $R^6$, $R^7$, $R^{13}$, $R^{14}$, $R^{16}$ and $R^{25}$ are as previously defined.

In a preferred embodiment, the compounds of Formula (IV), do not include the following compounds:

when either $R^{13}$ or $R^{14}$ is hydrogen, alkoxycarbonyl, substituted alkoxycarbonyl, carbamoyl, cycloalkoxycarbonyl or substituted cycloalkoxycarbonyl, then the other of $R^{13}$ or $R^{14}$ is not hydrogen; and $R^{25}C(O)$ is not a moiety derived from a bile acid.

In one embodiment of compounds of Formulae (IV), $R^{13}$ and $R^{14}$ are independently hydrogen, alkyl, substituted alkyl, alkoxycarbonyl, aryl, arylalkyl, carbamoyl, cycloalkyl, substituted cycloalkyl, cycloalkoxycarbonyl or heteroaryl (preferably, when $R^{13}$ is alkoxycarbonyl, cycloalkoxycarbonyl or carbamoyl then $R^{14}$ is methyl). More preferably, $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In another embodiment of compounds of Formula (IV), $R^{13}$ and $R^{14}$ are independently hydrogen, alkanyl, substituted alkanyl, cycloalkanyl or substituted cycloalkanyl. Preferably, $R^{13}$ and $R^{14}$ are hydrogen, alkanyl or cycloalkanyl. More preferably, $R^{13}$ and $R^{14}$ are independently hydrogen, methyl, ethyl, propyl, isopropyl, butyl, isobutyl, sec-butyl, tert-butyl, cyclopentyl or cyclohexyl. Even more preferably, $R^{13}$ is methyl, ethyl, propyl, isopropyl, butyl, isobutyl, sec-butyl, tert-butyl, cyclopentyl or cyclohexyl and $R^{14}$ is hydrogen, or $R^{13}$ is methyl and $R^{14}$ is methyl.

In still another embodiment of compounds of Formula (IV), $R^{13}$ and $R^{14}$ are independently hydrogen, aryl, arylalkyl or heteroaryl. More preferably, $R^{13}$ and $R^{14}$ are independently hydrogen, phenyl, benzyl, phenethyl or 3-pyridyl. Even more preferably, $R^{13}$ is phenyl, benzyl, phenethyl or 3-pyridyl and $R^{14}$ is hydrogen.

In still another embodiment of compounds of Formula (IV), $R^{13}$ and $R^{14}$ are independently hydrogen, alkyl, substituted alkyl, alkoxycarbonyl, carbamoyl, or cycloalkoxycarbonyl. Preferably, when $R^{13}$ is alkoxycarbonyl, cycloalkoxycarbonyl or carbamoyl then $R^{14}$ is methyl. More preferably, $R^{13}$ is methoxycarbonyl, ethoxycarbonyl, isopropoxycarbonyl, butoxycarbonyl, isobutoxycarbonyl, sec-butoxycarbonyl, tert-butoxycarbonyl or cyclohexyloxycarbonyl and $R^{14}$ is methyl.

In still another embodiment of compounds of Formula (IV), $R^{13}$ and $R^{14}$ together with the carbon atom to which they are attached form a cycloalkyl, substituted cycloalkyl, cycloheteroalkyl or substituted cycloheteroalkyl ring. Preferably, $R^{13}$ and $R^{14}$ together with the carbon atom to which they are attached form a cycloalkyl ring. More preferably, $R^{13}$ and $R^{14}$ together with the carbon atom to which they are attached form a cyclobutyl, cyclopentyl or cyclohexyl ring.

In still another embodiment of compounds of Formula (IV), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl. Preferably, $R^{25}$ is acyl, substituted acyl, alkyl, substituted alkyl, aryl, arylalkyl, cycloalkyl or heteroaryl. More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment of compounds of Formula (IV), $R^{25}$ is acyl or substituted acyl. More preferably, $R^{25}$ is acetyl, propionyl, butyryl, benzoyl or phenacetyl.

In still another embodiment of compounds of Formula (IV), $R^{25}$ is alkanyl or substituted alkanyl. Preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1, 3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl. More preferably, $R^{25}$ is methyl, ethyl, propyl, isopropyl, butyl, 1,1-dimethoxyethyl or 1,1-diethoxyethyl.

In still another embodiment of compounds of Formula (IV), $R^{25}$ is aryl, arylalkyl or heteroaryl. Preferably, $R^{25}$ is phenyl, 4-methoxyphenyl, benzyl, phenethyl, styryl or 3-pyridyl.

In still another embodiment of compounds of Formula (IV), $R^{25}$ is cycloalkyl or substituted cycloalkyl. More preferably $R^{25}$ is cyclopropyl, cyclobutyl, cyclopentyl or cyclohexyl.

In still another embodiment of compounds of Formula (IV), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, alkoxycarbonyl, aryl, arylalkyl, carbamoyl, cycloalkyl, cycloalkoxycarbonyl or heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. Even more preferably, $R^{25}$ is methyl, ethyl, propyl, isopropyl, butyl, isobutyl, sec-butyl, 1,1-dimethoxyethyl, 1,1-diethoxyethyl, 1,1-dimethoxybenzyl, 1,1-diethoxybenzyl, 1,1-dimethoxy-2-phenethyl, 1,1-diethoxy-2-phenethyl, acetyl, propionyl, butyryl, benzoyl, phenacetyl, phenyl, 4-methoxyphenyl, benzyl, phenethyl, cyclohexyl or 3-pyridyl, and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl or 3-pyridyl.

In still another embodiment of compounds of Formula (IV), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl and $R^{13}$ and $R^{14}$ together with the atom to which they are attached form a cycloalkyl, substituted cycloalkyl, cycloheteroalkyl or substituted cycloheteroalkyl ring. Preferably, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl, and $R^{13}$ and $R^{14}$ together with the atom to which they are attached form a cyclobutyl, cyclopentyl or a cyclohexyl ring.

In still another embodiment of compounds of Formula (IV), $R^{25}$ is acyl or substituted acyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is acetyl, propionyl, butyryl, benzoyl or phenacetyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment of compounds of Formula (IV), $R^{25}$ is alkanyl or substituted alkanyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment of compounds of Formula (IV), $R^{25}$ is aryl, substituted aryl, arylalkyl, substituted arylalkyl, heteroaryl or substituted heteroaryl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably $R^{25}$ is phenyl, 4-methoxyphenyl, benzyl, phenethyl, styryl or 3-pyridyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment of compounds of Formula (IV), $R^{25}$ is cycloalkyl or substituted cycloalkyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is cyclopropyl, cyclobutyl, cyclopentyl or cyclohexyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment of compounds of Formula (IV), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroalkyl, heteroaryl, substituted heteroaryl, heteroarylalkyl or substituted heteroarylalkyl, and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, alkanyl, substituted alkanyl, cycloalkanyl or substituted cycloalkanyl. More preferably, $R^{25}$ is acyl, substituted acyl, alkyl, substituted alkyl, aryl, arylalkyl, cycloalkyl or heteroaryl and $R^{13}$ and $R^{14}$ are independently hydrogen, methyl, ethyl, propyl, isopropyl, butyl, isobutyl, sec-butyl, tert-butyl, cyclopentyl or cyclohexyl. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment of compounds of Formula (IV), $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, aryl, arylalkyl or heteroaryl. More preferably, $R^{25}$ is acyl, substituted acyl, alkyl, substituted alkyl, aryl, arylalkyl, cycloalkyl or heteroaryl and $R^{13}$ and $R^{14}$ are independently hydrogen, phenyl, benzyl, phenethyl or 3-pyridyl. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment of compounds of Formula (IV), $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, alkoxycarbonyl, substituted alkoxycarbonyl, carbamoyl, cycloalkoxycarbonyl or substituted cycloalkoxycarbonyl (preferably, when $R^{13}$ is alkoxycarbonyl, substituted alkoxycarbonyl, carbamoyl, cycloalkoxycarbonyl or substituted cycloalkoxycarbonyl then $R^{14}$ is methyl; more preferably, $R^{13}$ is methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl or cyclohexyloxycarbonyl, and $R^{14}$ is methyl). In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment of compounds of Formula (IV), $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl, substituted cycloalkyl, cycloheteroalkyl or substituted cycloheteroalkyl ring. Preferably, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. More preferably $R^{25}$ is acyl, substituted acyl, alkyl, substituted alkyl, aryl, arylalkyl, cycloalkyl or heteroaryl, and $R^{13}$ and $R^{14}$ together with the atom to which they are attached form a cyclobutyl, cyclopentyl or cyclohexyl ring. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment of compounds of Formulae (I) and (III), $R^1$ is

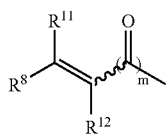

m is 0, and $R^8$, $R^{11}$ and $R^{12}$ are as previously defined.

In one embodiment of compounds of Formulae (I) and (III), $R^{11}$ is acyl, alkoxycarbonyl, aryloxycarbonyl, cycloalkoxycarbonyl or carbamoyl, $R^8$ is hydrogen, alkoxycarbonyl, alkyl, aryl, arylalkyl or cyano and $R^{12}$ is hydrogen, alkoxycarbonyl, alkyl, substituted alkyl, aryl, or arylalkyl.

In another embodiment of compounds of Formulae (I) and (III), $R^{11}$ is selected from the group consisting of acetyl, propionyl, butyryl, isobutyryl, pivaloyl, cyclopentanecarbonyl, cyclohexanecarbonyl, benzoyl, phenacetyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclopentyloxycarbonyl, cyclohexyloxycarbonyl, phenoxycarbonyl, benzyloxycarbonyl, carbamoyl, N-methylcarbamoyl, N-ethylcarbamoyl, N-propylcarbamoyl, N-isopropylcarbamoyl, N-butylcarbamoyl, N-isobutylcarbamoyl, N-sec-butylcarbamoyl, N-tert-butylcarbamoyl, N-cyclopentylcarbamoyl, N-cyclohexylcarbamoyl, N-phenylcarbamoyl, N-benzylcarbamoyl, N,N-dimethylcarbamoyl, N,N-diethylcarbamoyl, N,N-dipropylcarbamoyl, N,N-diisopropylcarbamoyl, N,N-dibutylcarbamoyl, N,N-dibenzylcarbamoyl, N-pyrrolidinylcarbamoyl, N-piperidinylcarbamoyl and N-morpholinylcarbamoyl. More preferably, $R^{11}$ is selected from the group consisting of acetyl, propionyl, butyryl, isobutyryl, cyclohexanecarbonyl, benzoyl, phenacetyl, methoxycarbonyl, ethoxycarbonyl, propoxycarbonyl, isopropoxycarbonyl, butoxycarbonyl, cyclohexyloxycarbonyl, phenoxycarbonyl, benzyloxycarbonyl, carbamoyl, N-methylcarbamoyl, N-ethylcarbamoyl, N-propylcarbamoyl, N-isopropylcarbamoyl, N-phenylcarbamoyl, N-benzylcarbamoyl, N,N-dimethylcarbamoyl, N,N-diethylcarbamoyl, N,N-dipropylcarbamoyl, N-pyrrolidinylcarbamoyl, N-piperidinylcarbamoyl and N-morpholinylcarbamoyl.

In still another embodiment of compounds of Formulae (I) and (III), $R^8$ is selected from the group consisting of hydrogen, methyl, ethyl, propyl, isopropyl, phenyl, benzyl, methoxycarbonyl, ethoxycarbonyl, propoxycarbonyl, isopropoxycarbonyl, butoxycarbonyl, phenoxycarbonyl, benzyloxycarbonyl and cyano. More preferably $R^8$ is selected from the group consisting of hydrogen, methyl, ethyl, isopropyl, phenyl, benzyl, methoxycarbonyl, ethoxycarbonyl and butoxycarbonyl.

In still another embodiment of compounds of Formulae (I) and (III), $R^{12}$ is selected from the group consisting of hydrogen, methyl, ethyl, propyl, isopropyl, phenyl, benzyl, methoxycarbonyl, ethoxycarbonyl, propoxycarbonyl, isopropoxycarbonyl, butoxycarbonyl, phenoxycarbonyl and benzyloxycarbonyl. More preferably $R^{12}$ is selected from the group consisting of hydrogen, methyl, ethyl, isopropyl, phenyl, benzyl, methoxycarbonyl, ethoxycarbonyl and butoxycarbonyl.

In still another embodiment of compounds of Formulae (I) and (III), $R^{11}$ is selected from the group consisting of hydrogen, alkoxycarbonyl, alkyl, substituted alkyl, aryl, arylalkyl and $R^8$ and $R^{12}$ together with the carbon atoms to which they are attached form a cycloalkyl, substituted cycloalkyl, cycloheteroalkyl or substituted cycloheteroalkyl ring. Preferably, $R^{11}$ is selected from the group consisting of hydrogen, methyl, ethyl, isopropyl, phenyl, benzyl, methoxycarbonyl, ethoxycarbonyl and butoxycarbonyl, and $R^8$ and $R^{12}$ together with the carbon atoms to which they are attached form a cycloalkyl, substituted cycloalkyl, cycloheteroalkyl or substituted cycloheteroalkyl ring. More preferably, $R^{11}$ is hydrogen or methyl and $R^8$ and $R^{12}$ together with the carbon atoms to which they are attached form a cyclopent-1-ene, cyclohex-1-ene, 2-cyclopenten-1-one, 2-cyclohexen-1-one, 2-(5H)-furanone or 5,6-dihydro-pyran-2-one ring.

In still another embodiment of compounds of Formulae (I) and (III), $R^{12}$ is selected from the group consisting of hydrogen, alkoxycarbonyl, alkyl, substituted alkyl, aryl, arylalkyl and $R^8$ and $R^{11}$ together with the carbon atoms to which they are attached form a cycloalkyl, substituted cycloalkyl, cycloheteroalkyl or substituted cycloheteroalkyl ring. Preferably, $R^{12}$ is selected from the group consisting of hydrogen, methyl, ethyl, isopropyl, phenyl, benzyl, methoxycarbonyl, ethoxycarbonyl and butoxycarbonyl, and $R^8$ and $R^{11}$ together with the carbon atoms to which they are attached form a cycloalkyl, substituted cycloalkyl, cycloheteroalkyl or substituted cycloheteroalkyl ring. More preferably, $R^{12}$ is selected from the group consisting of hydrogen, methyl, ethyl, isopropyl, phenyl, benzyl, methoxycarbonyl, ethoxycarbonyl and butoxycarbonyl, and $R^8$ and $R^{11}$ together with the carbon atoms to which they are attached form a γ-butyrolactone, δ-valerolactone or 2,2-dimethyl-1,3-dioxan-4,6-dione ring.

In still another embodiment of compounds of Formulae (I) and (III), $R^1$ is

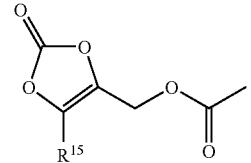

and $R^{15}$ is selected from the group consisting of alkyl, substituted alkyl, cycloalkyl, substituted cycloalkyl, aryl, substituted aryl, heteroaryl and substituted heteroaryl. Preferably, $R^{15}$ is methyl, ethyl, propyl, isopropyl, cyclopentyl, cyclohexyl, phenyl, 4-hydroxyphenyl, benzyl, 4-hydroxybenzyl or 3-pyridyl.

In still another embodiment, of Formulae (I) and (III), $R^1$ is

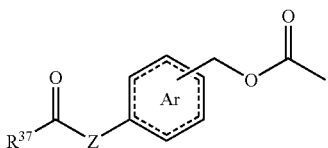

where R$^{37}$ is hydrogen, alkyl, substituted alkyl, acyl, aryl, substituted aryl, arylalkyl, substituted arylalkyl, cycloalkyl, heterocycloalkyl, substituted cycloheteroalkyl, heteroaryl, substituted heteroaryl, heteroarylalkyl or substituted heteroarylalkyl;

Z is O, N or S; and

Ar is aryl, substituted aryl, heteroaryl or substituted heteroaryl.

Preferably, Z and $CH_2OC(O)$— are in a conjugated relationship with one another (e.g., 1,4 or 1,2 related in a six membered ring system).

In still another embodiment, of Formulas (I) and (III), R$^1$ is

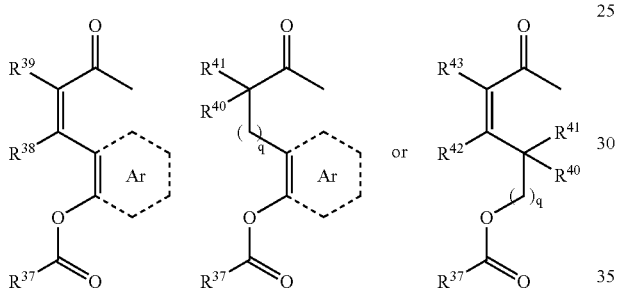

where q is 0 or 1;

R$^{38}$ and R$^{39}$ are independently hydrogen, alkyl, substituted alkyl, cycloalkyl, substituted alkyl, aryl, substituted aryl, heteroaryl and substituted heteroaryl;

R$^{40}$ and R$^{41}$ are independently hydrogen, alkyl, substituted alkyl, cycloalkyl, substituted alkyl, aryl, substituted aryl, heteroaryl and substituted heteroaryl; or together with the carbon atom to which they are attached form a cycloalkyl ring R$^{42}$ and R$^{43}$ are independently alkyl, substituted alkyl, cycloalkyl, substituted alkyl, aryl, substituted aryl, heteroaryl and substituted aryl or together with the carbon atoms to which they are attached form an aryl, substituted aryl, heteroaryl or substituted aryl ring; and R$^{37}$ is as previously defined.

In a preferred embodiment of compounds of Formulae (I)–(IV), Y is O, R$^3$, R$^6$ and R$^7$ are hydrogen and R$^4$ and R$^5$ together with the carbon atom to which they are attached form a cycloalkyl, substituted cycloalkyl, cycloheteroalkyl, substituted cycloheteroalkyl, bridged cycloalkyl or substituted bridged cycloalkyl ring. In another preferred embodiment of compounds of Formulae (I)–(IV), R$^4$ and R$^5$ together with the carbon atom to which they are attached form a cycloalkyl or substituted cycloalkyl ring. In one embodiment n is 0, t is 0 and u is 0. In another embodiment, n is 1 and R$^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$SCH$_3$, CH$_2$SH, —CH$_2$(CH$_2$)$_3$NH$_2$ or —CH$_2$CH$_2$CH$_2$NHC(NH)NH$_2$. In still another embodiment, n is 1 and R$^2$ and R$^{16}$ together with the atoms to which they are attached form a pyrrolidine ring.

In still another preferred embodiment of compounds of Formulae (I)–(IV), R$^4$ and R$^5$ together with the carbon atom to which they are attached form a cyclobutyl or substituted cyclobutyl ring. Preferably, the substituted cyclobutyl ring is substituted with one or more substituents selected from the group consisting of alkanyl, substituted alkanyl, halo, hydroxy, carboxyl and alkoxycarbonyl.

In still another preferred embodiment of compounds of Formulae (I)–(IV), R$^4$ and R$^5$ together with the carbon atom to which they are attached form a cyclopentyl or substituted cyclopentyl ring. Preferably, the cyclopentyl ring is substituted with alkanyl, substituted alkanyl, halo, hydroxy, carboxyl or alkoxycarbonyl. More preferably, the cyclopentyl ring is substituted with alkanyl. Even more preferably, the cyclopentyl ring is selected from the group consisting of

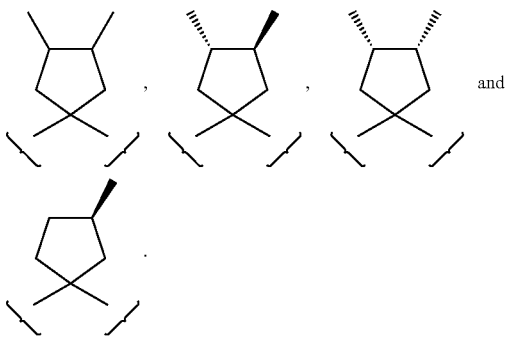

Preferably, in a more specific version of the above embodiments, R$^7$ is hydrogen.

In still another preferred embodiment of compounds of Formulae (I)–(IV), R$^4$ and R$^5$ together with the carbon atom to which they are attached form a cyclohexyl or substituted cyclohexyl ring. Preferably, the cyclohexyl ring is substituted with alkanyl, substituted alkanyl, halo, hydroxy, carboxyl or alkoxycarbonyl. More preferably, the cyclohexyl ring is substituted with alkanyl. Even more preferably, the cyclohexyl ring is selected from the group consisting of

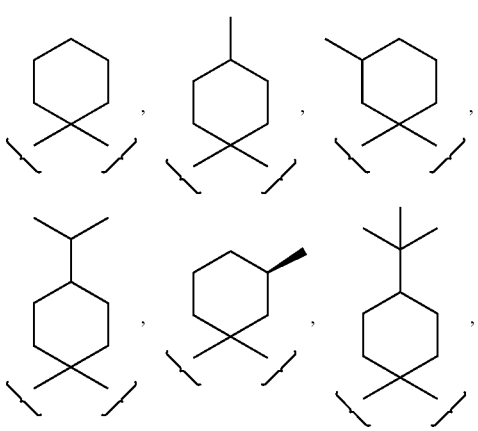

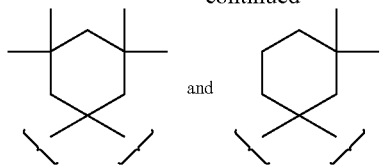

Preferably, in a more specific version of the above embodiments, $R^7$ is hydrogen.

In still another preferred embodiment of compounds of Formulae (I)–(IV), $R^4$ and $R^5$ together with the carbon atom to which they are attached form a cycloheteroalkyl or substituted cycloheteroalkyl ring.

In one embodiment, n is 0. In another embodiment, n is 1, and $R^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In still another embodiment, n is 1 and $R^2$ and $R^{16}$ together with the atoms to which they are attached form a pyrrolidine ring. Preferably, $R^4$ and $R^5$ together with the carbon atom to which they are attached form a cycloheteroalkanyl ring. More preferably, the cycloheteroalkanyl ring is selected from the group consisting of

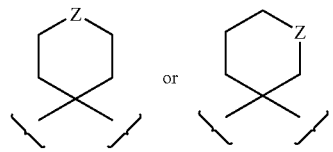

wherein Z is O, S(O)$_p$ or NR$^{18}$;
p is 0, 1 or 2; and
$R^{18}$ is selected from the group consisting of hydrogen, alkyl, substituted alkyl, acyl and alkoxycarbonyl. More preferably, the cycloheteroalkanyl ring is selected from the group consisting of

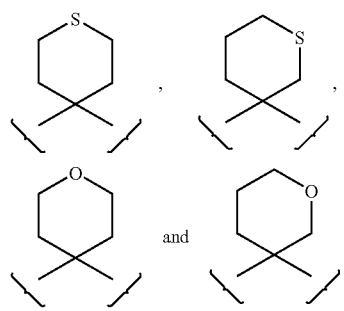

Preferably, in a more specific version of the above embodiments, $R^7$ is hydrogen.

In still another embodiment of compounds of Formulae (I)–(IV), $R^4$ and $R^5$ together with the carbon atom to which they are attached form a bridged cycloalkyl ring. In one embodiment, n is 0. In another embodiment, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In another embodiment, n is 1 and $R^2$ and $R^{16}$ together with the atoms to which they are attached form a pyrrolidine ring. Preferably, the bridged cycloalkyl group is

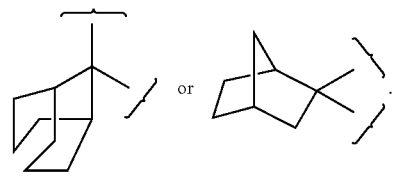

Preferably, in a more specific version of the above embodiments, $R^7$ is hydrogen.

In still another embodiment of compounds of Formulae (I)–(IV), Y is O, $R^6$ and $R^7$ are hydrogen, $R^4$ is alkyl or cycloalkyl, $R^5$ is hydrogen or alkyl and $R^3$ is hydrogen or alkyl. In one embodiment, n is 0. In another embodiment, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In still another embodiment, n is 1 and $R^2$ and $R^{16}$ together with the atoms to which they are attached form a pyrrolidine ring. Preferably, $R^4$ is cycloalkyl, $R^5$ is hydrogen or methyl, and $R^3$ is hydrogen or methyl. Preferably, $R^3$ is hydrogen, $R^4$ is isobutyl and $R^5$ is hydrogen.

In still another embodiment of compounds of Formulae (I)–(IV), Y is O, $R^5$ and $R^7$ are hydrogen or alkanyl, $R^3$ and $R^6$ are hydrogen and $R^4$ is substituted heteroalkyl. Preferably, $R^4$ is

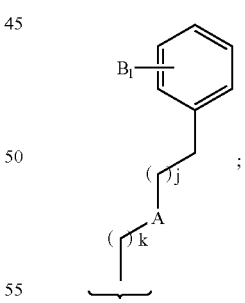

A is NR$^{19}$, O or S;
B is alkyl, substituted alkyl, alkoxy, halogen, hydroxy, carboxyl, alkoxycarbonyl or amino;
$R^{19}$ is hydrogen, alkyl, cycloalkyl or aryl;
j is an integer from 0 to 4;
k is an integer from 1 to 4; and
l is an integer from 0 to 3.
More preferably, k is 1.

In still another embodiment of compounds of Formulae (I)–(IV), Y is O, $R^5$ and $R^7$ are hydrogen or alkanyl, $R^3$ and $R^6$ are hydrogen and $R^4$ is substituted alkanyl, cycloalkanyl or substituted cycloalkanyl. Preferably, $R^4$ is selected from the group consisting of

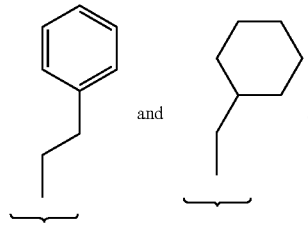

Preferably, $R^4$ is

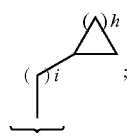

h is an integer from 1 to 6; and
i is an integer from 0 to 6.

More preferably, h is 1, 2, 3 or 4 and i is 0 or 1. Even more preferably, $R^4$ is selected from the group consisting of

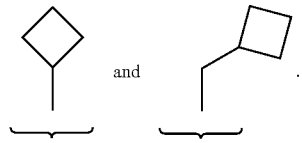

Preferably, compounds of Formulae (I)–(IV) are derived from a GABA analog of Formula (XIII):

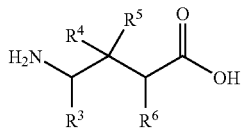

wherein the GABA analog of Formula (XIII) is selected from the group consisting of:
1-Aminomethyl-1-cyclohexane acetic acid;
1-Aminomethyl-1-(3-methylcyclohexane) acetic acid;
1-Aminomethyl-1-(4-methylcyclohexane) acetic acid;
1-Aminomethyl-1-(4-isopropylcyclohexane) acetic acid;
1-Aminomethyl-1-(4-tert-butylcyclohexane) acetic acid;
1-Aminomethyl-1-(3,3-dimethylcyclohexane) acetic acid;
1-Aminomethyl-1-(3,3,5,5-tetramethylcyclohexane) acetic acid;
1-Aminomethyl-1-cyclopentane acetic acid;
1-Aminomethyl-1-(3-methylcyclopentane) acetic acid;
1-Aminomethyl-1-(3,4-dimethylcyclopentane) acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl) acetic acid;
3-Aminomethyl-3-(tetrahydropyran-3-yl) acetic acid;
4-Aminomethyl-4-(tetrahydrothiopyran-4-yl) acetic acid;
3-Aminomethyl-3-(tetrahydrothiopyran-3-yl) acetic acid;
3-Aminomethyl-5-methyl-hexanoic acid;
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butyric acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

Particularly preferred embodiments of Formula (I) include compounds of Formulae (V) and (VI):

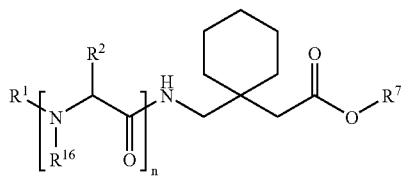

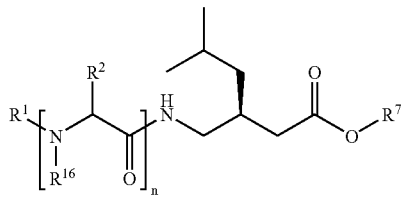

where $R^1$, $R^2$, $R^7$ and $R^{16}$ are as previously defined.

In one embodiment of compounds of Formulae (V) and (VI), n is 0. In another embodiment, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. Preferably, in the above embodiments, $R^7$ is hydrogen.

In another embodiment of compounds of Formulae (V) and (VI), n is 1, $R^1$ is $R^{24}$C(O)— or $R^{24}$C(S)—; and $R^{24}$ is alkyl, substituted alkyl, heteroalkyl, aryl, substituted aryl, heteroaryl or substituted heteroaryl. Preferably, $R^{24}$ is methyl, ethyl, 2-propyl, t-butyl, —CH$_2$OCH(CH$_3$)$_2$, phenyl or 3-pyridyl. Preferably, in this embodiment, $R^7$ is hydrogen, alkanyl, substituted alkanyl, alkenyl, substituted alkenyl, aryl or substituted aryl. More preferably, $R^7$ is hydrogen, methyl, ethyl, benzyl, —C(CH$_3$)=CH$_2$, —CH$_2$C(O)N(CH$_3$)$_2$,

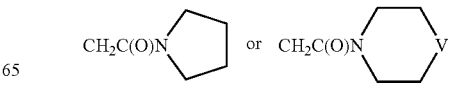

where V is O or CH$_2$. Most preferably, R$^7$ is hydrogen.

In still another embodiment of compounds of Formulae (V) and (VI), n is 1, R$^1$ is R$^{25}$OC(O)— or R$^{25}$SC(O)—; and R$^{25}$ is alkyl, substituted alkyl, heteroalkyl, aryl, substituted aryl, heteroaryl or substituted heteroaryl. Preferably, R$^{25}$ is ethyl, 2-propyl, neopentyl, —CH$_2$OCH(CH$_3$)$_2$, phenyl or 2-pyridyl. Preferably in this embodiment, R$^7$ is hydrogen, alkanyl, substituted alkanyl, alkenyl, substituted alkenyl, aryl or substituted aryl. More preferably, R$^7$ is hydrogen, methyl, ethyl, benzyl, —C(CH$_3$)=CH$_2$, —CH$_2$C(O)N(CH$_3$)$_2$,

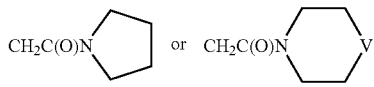

where V is O or CH$_2$. Most preferably, R$^7$ is hydrogen.

In still another embodiment of compounds of Formulae (V) and (VI), R$^1$ is

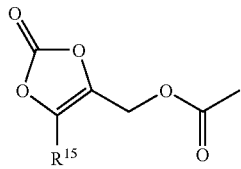

and R$^{15}$ is selected from the group consisting of alkyl, substituted alkyl, cycloalkyl, substituted cycloalkyl, aryl, substituted aryl, heteroaryl and substituted heteroaryl. Preferably, R$^{15}$ is methyl, ethyl, propyl, isopropyl, cyclopentyl, cyclohexyl, phenyl, 4-hydroxyphenyl, benzyl, 4-hydroxybenzyl or 3-pyridyl. In a more specific version of this embodiment, R$^7$ is hydrogen, alkanyl, substituted alkanyl, alkenyl, substituted alkenyl, aryl or substituted aryl. More preferably, R$^7$ is hydrogen, methyl, ethyl, benzyl, —C(CH$_3$)=CH$_2$, —CH$_2$C(O)N(CH$_3$)$_2$,

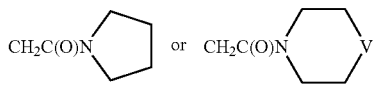

where V is O or CH$_2$. Preferably, R$^7$ is hydrogen.

Particularly preferred embodiments of compounds of Formulae (V) and (VI) are compounds selected from the group consisting of:
1-{[((5-methyl-2-oxo-1,3-dioxol-4-en-4-yl)methoxy)carbonyl]aminomethyl}-1-cyclohexane acetic acid; and
3-{[((5-methyl-2-oxo-1,3-dioxol-4-en-4-yl)methoxy)carbonyl]aminomethyl}-5-methyl-hexanoic acid.

In still another embodiment of compounds of Formulae (V) and (VI), R$^1$ is

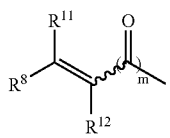

m is 0, and R$^8$, R$^{11}$ and R$^{12}$ are as previously defined. In one embodiment of compounds of Formulae (V) and (VI), R$^{11}$ is acyl, alkoxycarbonyl, aryloxycarbonyl, cycloalkoxycarbonyl, carbamoyl or substituted carbamoyl, R$^8$ is hydrogen, alkoxycarbonyl, alkyl, aryl, arylalkyl or cyano and R$^{12}$ is hydrogen, alkoxycarbonyl, alkyl, substituted alkyl, aryl, or arylalkyl. In another embodiment of compounds of Formulae (V) and (VI), R$^{11}$ is selected from the group consisting of acetyl, propionyl, butyryl, isobutyryl, pivaloyl, cyclopentanecarbonyl, cyclohexanecarbonyl, benzoyl, phenacetyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclopentyloxycarbonyl, cyclohexyloxycarbonyl, phenoxycarbonyl, benzyloxycarbonyl, carbamoyl, N-methylcarbamoyl, N-ethylcarbamoyl, N-propylcarbamoyl, N-isopropylcarbamoyl, N-butylcarbamoyl, N-isobutylcarbamoyl, N-sec-butylcarbamoyl, N-tert-butylcarbamoyl, N-cyclopentylcarbamoyl, N-cyclohexylcarbamoyl, N-phenylcarbamoyl, N-benzylcarbamoyl, N,N-dimethylcarbamoyl, N,N-diethylcarbamoyl, N,N-dipropylcarbamoyl, N,N-diisopropylcarbamoyl, N,N-dibutylcarbamoyl, N,N-dibenzylcarbamoyl, N-pyrrolidinylcarbamoyl, N-piperidinylcarbamoyl and N-morpholinylcarbamoyl. In still another embodiment of compounds of Formulae (V) and (VI), R$^{11}$ is selected from the group consisting of acetyl, propionyl, butyryl, isobutyryl, cyclohexanecarbonyl, benzoyl, phenacetyl, methoxycarbonyl, ethoxycarbonyl, propoxycarbonyl, isopropoxycarbonyl, butoxycarbonyl, cyclohexyloxycarbonyl, phenoxycarbonyl, benzyloxycarbonyl, carbamoyl, N-methylcarbamoyl, N-ethylcarbamoyl, N-propylcarbamoyl, N-isopropylcarbamoyl, N-phenylcarbamoyl, N-benzylcarbamoyl, N,N-dimethylcarbamoyl, N,N-diethylcarbamoyl, N,N-dipropylcarbamoyl, N-pyrrolidinylcarbamoyl, N-piperidinylcarbamoyl and N-morpholinylcarbamoyl.

In one embodiment of compounds of Formulae (V) and (VI), R$^8$ is selected from the group consisting of hydrogen, methyl, ethyl, propyl, isopropyl, phenyl, benzyl, methoxycarbonyl, ethoxycarbonyl, propoxycarbonyl, isopropoxycarbonyl, butoxycarbonyl, phenoxycarbonyl, benzyloxycarbonyl and cyano. Preferably, R$^8$ is selected from the group consisting of hydrogen, methyl, ethyl, isopropyl, phenyl, benzyl, methoxycarbonyl, ethoxycarbonyl and butoxycarbonyl.

In still another embodiment of compounds of Formulae (V) and (VI), R$^{12}$ is selected from the group consisting of hydrogen, methyl, ethyl, propyl, isopropyl, phenyl, benzyl, methoxycarbonyl, ethoxycarbonyl, propoxycarbonyl, isopropoxycarbonyl, butoxycarbonyl, phenoxycarbonyl and benzyloxycarbonyl. Preferably R$^{12}$ is selected from the group consisting of hydrogen, methyl, ethyl, isopropyl, phenyl, benzyl, methoxycarbonyl, ethoxycarbonyl and butoxycarbonyl.

In still another embodiment of compounds of Formulae (V) and (VI), R$^{11}$ is selected from the group consisting of hydrogen, alkoxycarbonyl, alkyl, substituted alkyl, aryl, arylalkyl and R$^8$ and R$^{12}$ together with the carbon atoms to which they are attached form a cycloalkyl, substituted cycloalkyl, cycloheteroalkyl or substituted cycloheteroalkyl ring. Preferably, R$^{11}$ is selected from the group consisting of hydrogen, methyl, ethyl, isopropyl, phenyl, benzyl, methoxycarbonyl, ethoxycarbonyl and butoxycarbonyl, and R$^8$ and R$^{12}$ together with the carbon atoms to which they are attached form a cycloalkyl, substituted cycloalkyl, cycloheteroalkyl or substituted cycloheteroalkyl ring. More preferably, R$^{11}$ is hydrogen or methyl and R$^8$ and R$^{12}$ together with the carbon atoms to which they are attached form a 2-cyclopenten-1-one, 2-cyclohexen-1-one, 2-(5H)-furanone or 5,6-dihydro-pyran-2-one ring.

In still another embodiment of compounds of Formulae (V) and (VI), $R^{12}$ is selected from the group consisting of hydrogen, alkoxycarbonyl, alkyl, substituted alkyl, aryl, arylalkyl and $R^8$ and $R^{11}$ together with the carbon atoms to which they are attached form a cycloalkyl, substituted cycloalkyl, cycloheteroalkyl or substituted cycloheteroalkyl ring. Preferably, $R^{12}$ is selected from the group consisting of hydrogen, methyl, ethyl, isopropyl, phenyl, benzyl, methoxycarbonyl, ethoxycarbonyl and butoxycarbonyl, and $R^8$ and $R^{11}$ together with the carbon atoms to which they are attached form a cycloalkyl, substituted cycloalkyl, cycloheteroalkyl or substituted cycloheteroalkyl ring. More preferably, $R^{12}$ is selected from the group consisting of hydrogen, methyl, ethyl, isopropyl, phenyl, benzyl, methoxycarbonyl, ethoxycarbonyl and butoxycarbonyl, and $R^8$ and $R^{11}$ together with the carbon atoms to which they are attached form a γ-butyrolactone, δ-valerolactone or 2,2-dimethyl-1,3-dioxan-4,6-dione ring.

In a more specific version of the above embodiments of compounds of Formulae (V) and (VI), $R^7$ is hydrogen, alkanyl, substituted alkanyl, alkenyl, substituted alkenyl, aryl or substituted aryl. More preferably, $R^7$ is hydrogen, methyl, ethyl, benzyl, —C(CH$_3$)=CH$_2$, —CH$_2$C(O)N(CH$_3$)$_2$,

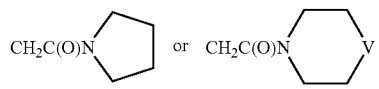

where V is O or CH$_2$. Most preferably $R^7$ is hydrogen.

Particularly preferred embodiments of compounds of Formulae (V) and (VI) are compounds selected from the group consisting of:

Piperidinium 1-{(1-methyl-3-oxo-but-1-enyl)aminomethyl}-1-cyclohexane acetate;

Piperidinium 1-{1-[(2-oxo-tetrahydrofuran-3-ylidene)ethyl]aminomethyl}-1-cyclohexane acetate;

Piperidinium 1-{(2-carbomethoxy-cyclopent-1-enyl)aminomethyl}-1-cyclohexane acetate; and Piperidinium 1-{(1-methyl-2-(ethoxycarbonyl)-3-ethoxy-3-oxoprop-1-enyl)aminomethyl}-1-cyclohexane acetate.

In a particularly preferred embodiment, compounds of Formula (IV) have the structure of Formulae (VII) or (VIII):

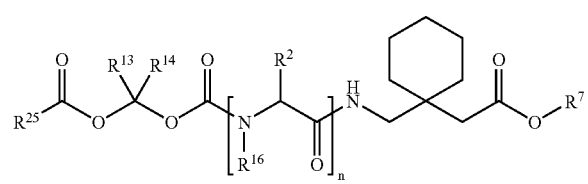

(VII)

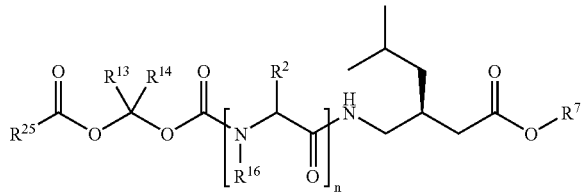

(VIII)

or a pharmaceutically acceptable salt, hydrate or solvate thereof, wherein:

n, $R^2$, $R^7$, $R^{13}$, $R^{14}$, $R^{16}$ and $R^{25}$ are as previously defined.

In one preferred embodiment, the compounds of Formulae (VII) and (VIII) do not include the following compounds:

if either $R^{13}$ or $R^{14}$ is hydrogen, alkoxycarbonyl, substituted alkoxycarbonyl, carbamoyl, cycloalkoxycarbonyl or substituted cycloalkoxycarbonyl, then the other of $R^{13}$ or $R^{14}$ is not hydrogen; and $R^{25}$C(O) is not a moiety derived from a bile acid.

In one embodiment of compounds of Formulae (VII) and (VIII), n is 0. In another embodiment, n is 1. When n is 1, preferably the α-amino acid is of the L-stereochemical configuration.

In another embodiment of compounds of Formulae (VII) and (VIII), $R^7$ is hydrogen, alkanyl, substituted alkanyl, alkenyl, substituted alkenyl, aryl or substituted aryl. Preferably, $R^7$ is hydrogen, methyl, ethyl, benzyl, —C(CH$_3$)=CH$_2$, —CH$_2$C(O)N(CH$_3$)$_2$,

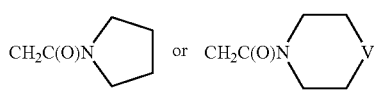

where V is O or CH$_2$. Most preferably, $R^7$ is hydrogen.

In still another embodiment of compounds of Formulae (VII) and (VIII), n is 0. In still another embodiment of compounds of Formulae (VII) and (VIII), n is 1, $R^{16}$ is hydrogen and $R^2$ is hydrogen, methyl, 2-propyl, 2-butyl, isobutyl, tert-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. Preferably $R^{16}$ is hydrogen and $R^2$ is hydrogen, methyl, 2-propyl, 2-butyl, isobutyl, tert-butyl, cyclohexyl, phenyl or benzyl. In still another embodiment, n is 1 and $R^2$ and $R^{16}$ together with the atoms to which they are attached form a pyrrolidine ring.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2- yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3- dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclopentyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butoxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyloxycarbonyl and $R^{14}$ is methyl.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is benzyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenethyl and $R^{14}$ is hydrogen.

In still another embodiment of compounds of Formulae (VII) and (VIII), $R^{25}$ is selected from the group consisting of methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is 3-pyridyl and $R^{14}$ is hydrogen.

Particularly preferred embodiments of compounds of Formulae (VII) and (VIII) include compounds selected from the group consisting of:

1-{[(α-Acetoxyethoxy)carbonyl]aminomethyl}-1-cyclohexane acetic acid;
1-{[(α-Propanoyloxyethoxy)carbonyl]aminomethyl}-1-cyclohexane acetic acid;
1-{[(α-Butanoyloxyethoxy)carbonyl]aminomethyl}-1-cyclohexane acetic acid;
1-{[(α-Isobutanoyloxyethoxy)carbonyl]aminomethyl}-1-cyclohexane acetic acid;
1-{[(α-Pivaloxyethoxy)carbonyl]aminomethyl}-1-cyclohexane acetic acid;
1-{[(α-Benzoyloxyethoxy)carbonyl]aminomethyl}-1-cyclohexane acetic acid;
1-{[(α-Acetoxybutoxy)carbonyl]aminomethyl}-1-cyclohexane acetic acid;
1-{[(α-Butanoyloxybutoxy)carbonyl]aminomethyl}-1-cyclohexane acetic acid;
1-{[(α-Isobutanoyloxybutoxy)carbonyl]aminomethyl}-1-cyclohexane acetic acid;
1-{[(α-Benzoyloxybutoxy)carbonyl]aminomethyl}-1-cyclohexane acetic acid;
1-{[(α-Acetoxyisobutoxy)carbonyl]aminomethyl}-1-cyclohexane acetic acid;
1-{[(α-Propanoyloxyisobutoxy)carbonyl]aminomethyl}-1-cyclohexane acetic acid;
1-{[(α-Butanoyloxyisobutoxy)carbonyl]aminomethyl}-1-cyclohexane acetic acid;
1-{[(α-Isobutanoyloxyisobutoxy)carbonyl]aminomethyl}-1-cyclohexane acetic acid;
1-{[(α-Pivaloxyisobutoxy)carbonyl]aminomethyl}-1-cyclohexane acetic acid;
1-{[(α-2,2-Diethoxypropanoyloxyisobutoxy)carbonyl]aminomethyl}-1-cyclohexane acetic acid;
1-{[(α-2-(1,3-Dioxolan-2-yl)propanoyloxyisobutoxy)carbonyl]aminomethyl}-1-cyclohexane acetic acid;
1-{[(α-(2-Amino-2-methylpropanoyl)oxyisobutoxy)carbonyl]aminomethyl}-1-cyclohexane acetic acid;
1-{[(α-Benzoyloxyisobutoxy)carbonyl]aminomethyl}-1-cyclohexane acetic acid;
1-{[(α-Nicotinoyloxyisobutoxy)carbonyl]aminomethyl}-1-cyclohexane acetic acid;
1-{[(α-Acetoxyisopropoxy)carbonyl]aminomethyl}-1-cyclohexane acetic acid;
1-{[(α-Butanoyloxyisopropoxy)carbonyl]aminomethyl}-1-cyclohexane acetic acid;
1-{[(α-Isobutanoyloxyisopropoxy)carbonyl]aminomethyl}-1-cyclohexane acetic acid;
1-{[(α-Benzoyloxyisopropoxy)carbonyl]aminomethyl}-1-cyclohexane acetic acid;
1-{[(α-Acetoxybenzyloxy)carbonyl]aminomethyl}-1-cyclohexane acetic acid;
1-{[(α-Benzoyloxybenzyloxy)carbonyl]aminomethyl}-1-cyclohexane acetic acid;
1-{[(1-(3-Methylbutanoyloxy)-2-phenylethoxy)carbonyl]aminomethyl}-1-cyclohexane acetic acid;
1-{[(1-Benzoyloxy-2-phenylethoxy)carbonyl]aminomethyl}-1-cyclohexane acetic acid;
1-{[N-[(α-Isobutanoyloxyethoxy)carbonyl]-4-bromophenylalaninyl]-aminomethyl}-1-cyclohexane acetic acid;
3-{[(α-Isobutanoyloxyethoxy)carbonyl]aminomethyl}-5-methylhexanoic acid;
3-{[(α-Isobutanoyloxyisobutoxy)carbonyl]aminomethyl}-5-methylhexanoic acid;
3-{[(α-Benzoyloxyisobutoxy)carbonyl]aminomethyl}-5-methylhexanoic acid; and
1-{[(α-Propanoyloxybutoxy)carbonyl]aminomethyl}-1-cyclohexane acetic acid.

In one embodiment, the compounds of the invention have the structure of Formula (II):

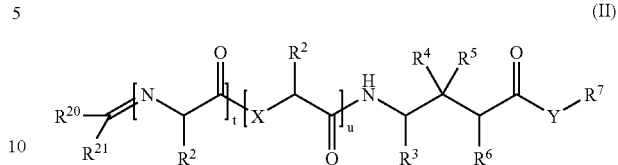

(II)

In an embodiment of compounds of Formula (II), when $R^3$, $R^5$ and $R^6$ are hydrogen, $R^4$ is not phenyl or substituted phenyl. More preferably, $R^4$ is not 4-chlorophenyl.

In a preferred embodiment, the compounds of Formula (II) have the structure of Formulae (IX) and (X):

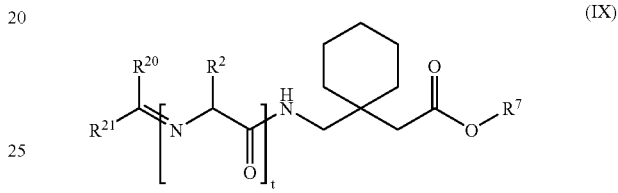

(IX)

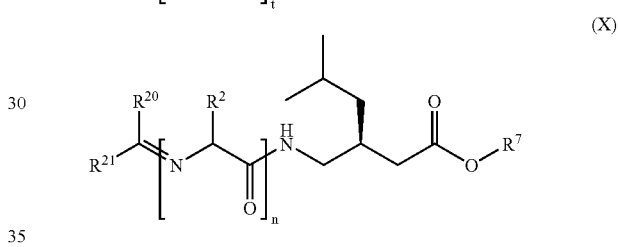

(X)

In one embodiment of compounds of Formulae (IX) and (X), t is 0. In another embodiment, t is 1 and $R^2$ is hydrogen, methyl, 2-propyl, 2-butyl, isobutyl, t-butyl, cyclopentyl, cyclohexyl, phenyl, benzyl, 4-hydroxybenzyl, 4-bromobenzyl, 2-imidazolyl, 4-imidazolylmethyl, 3-indolylmethyl, 2-indolyl, $—CH_2OH$, $—CH(OH)CH_3$, $—CH_2CO_2H$, $—CH_2CH_2CO_2H$, $—CH_2CONH_2$, $—CH_2CH_2CONH_2$, $—CH_2CH_2SCH_3$, $—CH_2SH$, $—CH_2(CH_2)_3NH_2$ or $—CH_2CH_2CH_2NHC(NH)NH_2$.

In still another embodiment of compounds of Formulae (IX) or (X), $R^{20}$ and $R^{21}$ are independently selected from the group consisting of alkyl, substituted alkyl, aryl, substituted aryl, heteroaryl and substituted heteroaryl. Preferably, $R^{20}$ and $R^{21}$ are independently selected from the group consisting of alkyl, substituted aryl and heteroaryl. In one embodiment, $R^{20}$ is methyl and $R^{21}$ is methyl. Preferably, in this last embodiment, $R^7$ is hydrogen, methyl, ethyl, benzyl, $—C(CH_3)=CH_2$, $—CH_2C(O)N(CH_3)_2$,

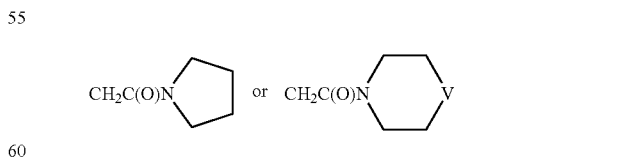

where V is O or $CH_2$. Most preferably, $R^7$ is hydrogen.

In another embodiment of compounds of Formulae (IX) or (X), $R^{20}$ and $R^{21}$ together with the carbon atom to which they are attached form a cycloalkyl or substituted cycloalkyl ring. In one embodiment, $R^{20}$ and $R^{21}$ together with the carbon atom to which they are attached form a cyclohexyl ring. Preferably, in this last embodiment, $R^7$ is hydrogen, methyl, ethyl, benzyl, —C(CH$_3$)=CH$_2$, —CH$_2$C(O)N(CH$_3$)$_2$,

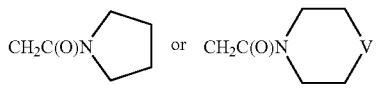

where V is O or CH$_2$. Most preferably, $R^7$ is hydrogen.

In one embodiment, the compounds of the invention have the structure of Formula (III):

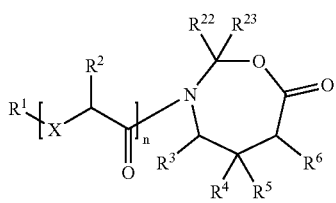

(III)

In one embodiment of the compounds of Formula (III), n is 1, $R^1$ is hydrogen and $R^2$ is arylalkyl. Preferably, $R^2$ is benzyl. In another embodiment of the compounds of Formula (III), n is 0 and $R^1$ is $R^{25}$OC(O)—. Preferably, $R^{25}$ is alkyl or substituted alkyl. More preferably, $R^{25}$ is ethyl. In still another embodiment of the compounds of Formula (III), $R^{22}$ and $R^{23}$ are hydrogen. In still another embodiment, $R^{22}$ and $R^{23}$ are alkyl or substituted alkyl. Preferably, $R^{22}$ and $R^{23}$ are methyl.

In a preferred embodiment, the compounds of Formula (III) have the structure of Formula (XI):

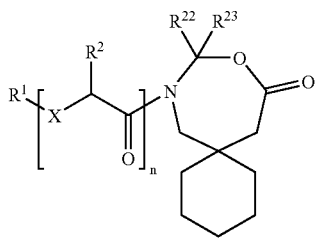

(XI)

In one embodiment of the compounds of Formula (XI), n is 1, X is NH, Y is O, $R^1$ is hydrogen, $R^2$ is benzyl, $R^{22}$ is methyl and $R^{23}$ are methyl. In another embodiment, n is 0, Y is O, $R^1$ is $R^{25}$OC(O)—, $R^{25}$ is ethyl, $R^{22}$ is hydrogen and $R^{23}$ is hydrogen.

In another embodiment, the compounds of Formula (III) have the structure of Formula (XII):

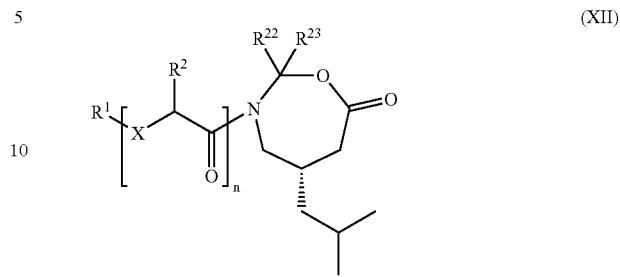

(XII)

In one embodiment of the compounds of Formula (XII), n is 1, X is NH, Y is O, $R^1$ is hydrogen, $R^2$ is benzyl, $R^{22}$ is methyl and $R^{23}$ are methyl. In another embodiment, n is 0, Y is O, $R^1$ is $R^{25}$OC(O)—, $R^{25}$ is ethyl, $R^{22}$ is hydrogen and $R^{23}$ is hydrogen.

The instant invention also comprises a GABA analog derivative, M-G, for administration to a patient in need of therapy, wherein M is a promoiety and G is derived from a GABA analog, H-G (where H is hydrogen). The promoiety M, once cleaved from G, and any metabolite thereof, exhibits a carcinogenically toxic dose (TD$_{50}$) in rats of greater than 0.2 mmol/kg/day. Further, the promoiety M is cleaved from G at a sufficient rate in vivo, upon colonic administration to rats, to produce:

(i) a maximum concentration of H-G in plasma (C$_{max}$) of at least 120% of the C$_{max}$ of H-G in plasma achieved by colonically administering an equimolar dose of H-G; and (ii) an AUC that is at least 120% of the AUC achieved by colonically administering an equimolar dose of H-G.

Preferably, M-G has the structure of Formula (XIV):

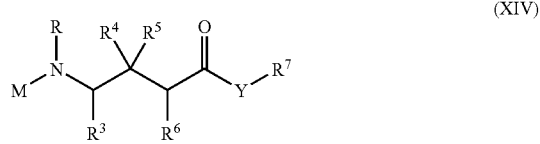

(XIV)

or a pharmaceutically acceptable salt, hydrate or solvate thereof, wherein:

M is a promoiety;

Y is O or S;

R is hydrogen, or R and $R^6$ together with the atoms to which they are attached form an azetidine, substituted azetidine, pyrrolidine or substituted pyrrolidine ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring; and $R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

In a preferred embodiment, M has the structure of Formula (XV):

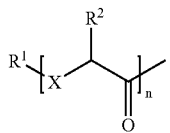

(XV)

wherein:

n, X, $R^1$ and $R^2$ are as previously defined

In one embodiment, M-G include compounds wherein H-G, once cleaved from M, is substantially free of any lactam having the structure of Formula (XVI):

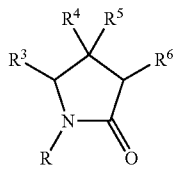

(XVI)

wherein R is hydrogen and $R^3$, $R^4$, $R^5$ and $R^6$ are as previously defined Preferably, promoiety M or any metabolite formed from M does not form formaldehyde or pivalic acid upon cleavage of G-M. In one embodiment, the promoiety M is cleaved from G at a sufficient rate in vivo, upon colonic administration to rats, to produce a $C_{max}$ of H-G in plasma of at least 200%, and most preferably at least 1000%, of the $C_{max}$ of H-G in plasma achieved by colonically administering an equimolar dose of H-G. Preferably, the promoiety M is cleaved from G at a sufficient rate in vivo, upon colonic administration to rats, to produce an AUC of H-G in plasma of at least 200%, and most preferably at least 500%, of the AUC of H-G in plasma achieved by colonically administering an equimolar dose of H-G. In another embodiment, the promoiety M is cleaved from H-G at a sufficient rate in vivo, following oral administration to dogs (e.g., using an osmotic mini-pump device) at a dose of about 60 μmol equivalent of H-G per kg, to produce a plasma concentration of H-G at 12 hours post dosing of at least 200% of the plasma concentration of H-G achieved from an equimolar dose of H-G following the same mode of administration.

4.3 Synthesis of the Compounds of the Invention

The compounds of the invention may be obtained via the synthetic methods illustrated in Schemes 1–17. Those of skill in the art will appreciate that a preferred synthetic route to the compounds of the invention consists of attaching promoieties to GABA analogs. Numerous methods have been described in the art for the synthesis of GABA analogs (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Bellioti et al., International Publication No. WO 00/31020; and Bryans et al., International Publication No. WO 00/50027). Other methods are known in the art for synthesizing GABA analogs, which are readily accessible to the skilled artisan. The promoieties described herein, are known in the art and may be prepared and attached to GABA analogs by established procedures (See e.g., Green et al., "Protective Groups in Organic Chemistry", (Wiley, $2^{nd}$ ed. 1991); Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Accordingly, starting materials useful for preparing compounds of the invention and intermediates thereof are commercially available or can be prepared by well-known synthetic methods. Other methods for synthesis of the prodrugs described herein are either described in the art or will be readily apparent to the skilled artisan in view of the references provided above and may be used to synthesize the compounds of the invention. Accordingly, the methods presented in the Schemes herein are illustrative rather than comprehensive.

In any of the Schemes below, after the amino group of a GABA analog has been functionalized with a promoiety or other protecting group, the carboxylic acid group may be converted to an ester or thioester by many synthetic methods, which are well-known to the skilled artisan. In one preferred embodiment, GABA analogs may be reacted with an alcohol or thiol in the presence of a coupling reagent (e.g., carbodiimide and dimethylaminopyridine) to provide the ester. In another preferred embodiment, GABA analogs may be reacted with an alkyl halide in the presence of base to yield the ester. Other methods for converting GABA analogs to esters or thioesters are well within the purview of the skilled artisan in view of the references provided herein.

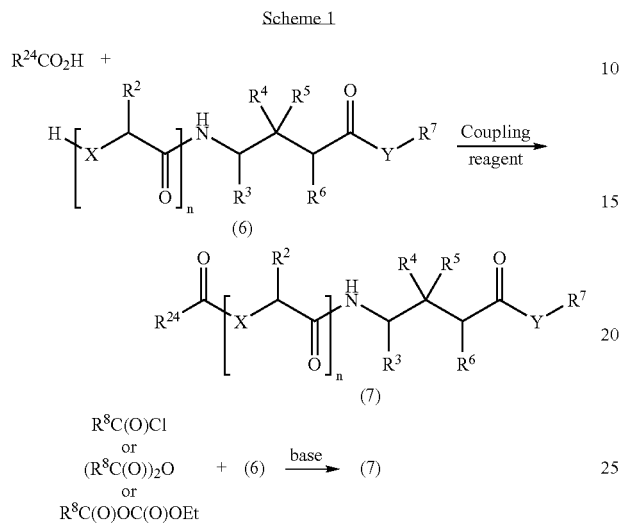

As illustrated above in Scheme 1, carboxylic acids can be directly coupled to the terminal amino (or hydroxyl) group of GABA analog derivatives (6) to provide adducts (7). Reagents for effecting this reaction are well known to the skilled artisan and include, but are not limited to, carbodiimides, aminium salts, phosphonium salts, etc. Alternatively, reaction of carboxylic acid derivatives such as acyl chlorides, symmetrical anhydrides or mixed anhydrides with GABA analogs (6) in the presence of base (e.g., hydroxide, tertiary amines, etc.) may be used to synthesize (7).

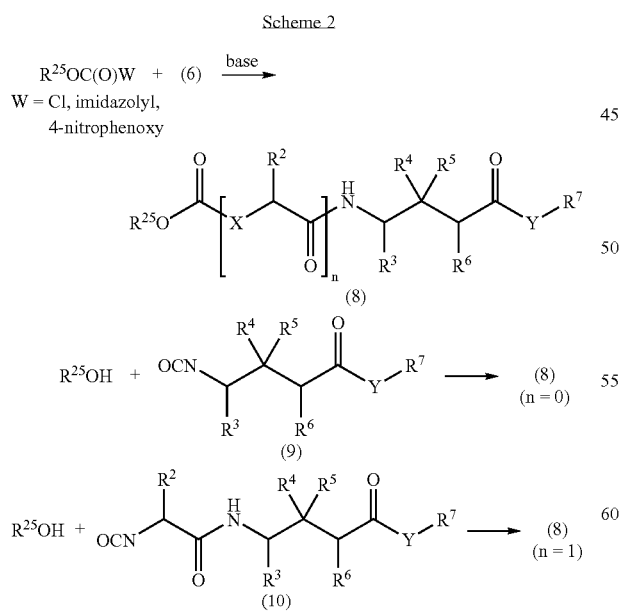

As illustrated in Scheme 2, GABA analog derivatives (6) may be converted to carbamates (8) by treatment with various carbonic acid derivatives in the presence of base (e.g., hydroxide, tertiary amines, etc.). Alternatively, the well-known addition of alcohols to isocyanates (9) or (10) may be used to synthesize (8).

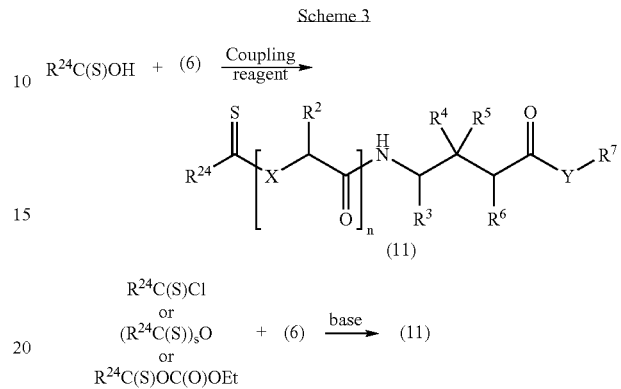

As illustrated in Scheme 3, GABA analog derivatives (6) may be converted to thioamides (11) by reaction with thioacids in the presence of coupling agents. Reagents for effecting this reaction are well known to the skilled artisan and include, but are not limited to, carbodiimides, aminium salts, phosphonium salts, etc. Alternatively, reaction of thio acid derivatives such as thioacyl chlorides, symmetrical anhydrides or mixed anhydrides with (6) in the presence of base (e.g., hydroxide, tertiary amines, etc.) may be used to synthesize thioamides (11). In yet another method, amides (7) may be converted to thioamides (11) by heating in the presence of phosphorus pentasulfide (when n=0).

Thiocarbamates (12) and (13) may be synthesized from the reaction of the corresponding thiocarbonate derivatives (i.e., P=O, Q=S and P=S Q=O, respectively) where W is chloride, imidazolyl or 4-nitrophenoxy with GABA analog derivatives (6) in the presence of base. Thiocarbamate (13) may also be formed by reaction of a thiol with isocyanates (9) or (10). Dithiocarbamate (14) (P=S, Q=S) may be made by reaction of GABA analog derivatives (6) with the dithiocarbonate derivative (i.e., P and Q=S) where W is chloride, imidazolyl or 4-nitrophenoxy in the presence of base (see Scheme 4).

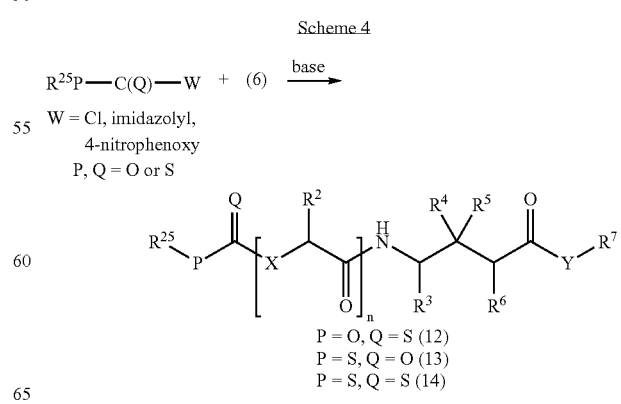

One method for synthesis of compounds of Formula (IV) is illustrated in Scheme 5.

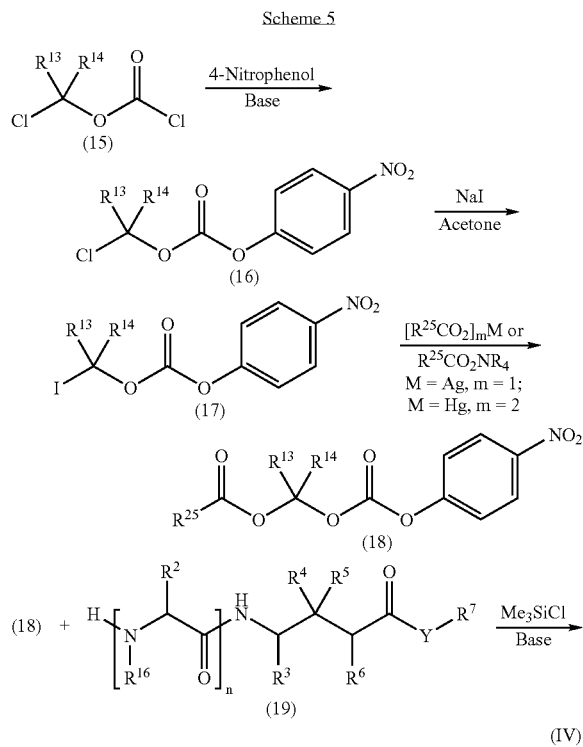

Chloroformate (15) is treated with an aromatic leaving group such as p-nitrophenol in the presence of base to provide p-nitrophenylcarbonate (16). Halide interchange provides iodide (17), which is reacted with a metal or tetraalkylammonium salt of a carboxylic acid to afford compound (18). Treatment of (18) with GABA analog derivative (19), optionally in the presence of trimethylsilyl chloride, affords a compound of Formula (IV). Methods for making related acyloxyalkyl carbamate compounds have been described in the art (Alexander, U.S. Pat. No. 4,760,057; Alexander, U.S. Pat. No. 4,916,230; Alexander, U.S. Pat. No. 5,466,811; Alexander, U.S. Pat. No. 5,684,018).

Alternatively compounds of Formula (IV) can be prepared from carbonate (18) in a stepwise fashion as illustrated in Scheme 6. Here reaction of (18) with an α-amino acid (20), optionally protected as an ester, affords intermediate (21) which upon deprotection (if necessary) provides compound (22), which is then coupled to GABA analog (23) using standard peptide coupling reagents well known in the art.

Scheme 6

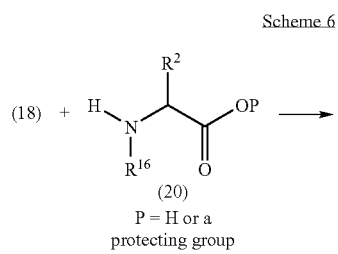

P = H or a protecting group

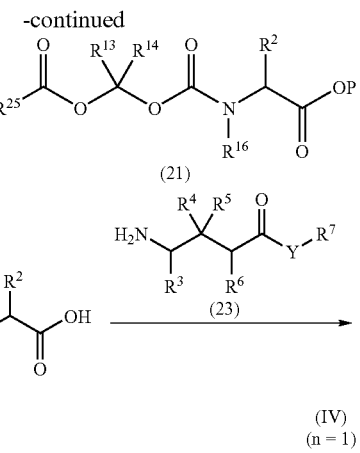

Another method for synthesis of compounds of Formula (IV) proceeds via carbonylation of GABA analog derivative (19) to an intermediate carbamic acid species, which is captured by an in situ alkylation reaction in an adaptation of the methods disclosed in the art (Butcher, *Synlett*, 1994, 825–6; Ferres et al., U.S. Pat. No. 4,036,829). Carbon dioxide gas is bubbled into a solution containing (19) and a base (e.g., $Cs_2CO_3$, $Ag_2CO_3$ or AgO) in a solvent such as DMF or NMP. The activated halide is added, optionally in the presence of iodide ion as a catalyst, and the carbonylation continued until the reaction is completed. This method is illustrated in Scheme 7 for the preparation of compounds of Formula (IV) from halide (24).

Scheme 7

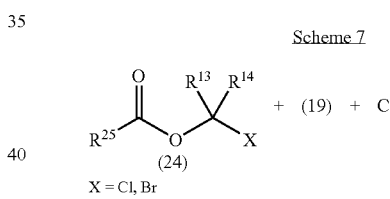

X = Cl, Br

Alternatively compounds of Formula (IV) can be prepared in a stepwise fashion as illustrated in Scheme 8. Carbonylation and alkylation of carboxyl protected α-amino acid (20) provides intermediate (21), which upon deprotection is coupled to GABA analog (23) as previously described in Scheme 6.

Scheme 8

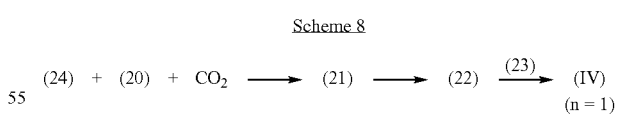

Yet another method for synthesis of compounds of Formula (IV) relies upon oxidation of ketocarbamate derivatives of GABA analogs (Gallop et al., co-pending U.S. patent application Ser. No. 10/167,797 entitled "Methods for Synthesis of Prodrugs from 1-Acyl-Alkyl Derivatives and Compositions Thereof"). As illustrated in Scheme 9, oxidation of ketocarbamate (25) affords compounds of Formula (IV). Preferred solvents include, but are not limited to, t-butanol, diethylether, acetic acid, hexane, dichloroethane, dichloromethane, ethyl acetate, acetonitrile, methanol, chloroform and water. Generally, the oxidant may be an organism (e.g., yeast or bacteria), or a chemical reagent (e.g., an enzyme or peroxide). Preferred oxidants include those, which have been successfully used in Baeyer-Villager oxidations of ketones to esters or lactones (Strukul, *Angnew. Chem. Int. Ed.*, 1998, 37, 1198; Renz et al., *Eur. J. Org. Chem.* 1999, 737; Beller et al., in "Transition Metals in Organic Synthesis" Chapter 2, Wiley VCH; Stewart, *Current Organic Chemistry*, 1998, 2, 195; Kayser et al., *Synlett*, 1999, 1, 153).

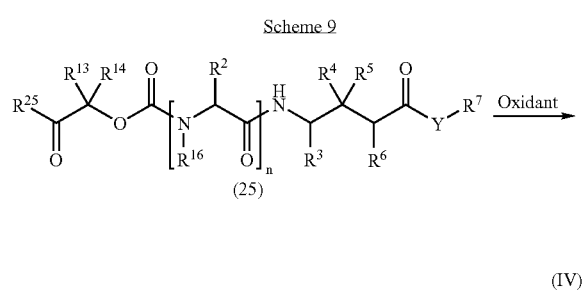

Other compounds of this invention may be amenable to synthesis from the appropriate ketocarbamate derivative via this Baeyer-Villiger type oxidation, provided that they do not contain chemical functionality susceptible to decomposition or other transformation under conditions of the reaction.

Ketocarbamates (25) may be prepared from the corresponding α-hydroxyketone compounds (26) either directly, via reaction with isocyanate (9), or by first converting the α-hydroxyketone compound to a haloformate or activated carbonate intermediate (27) and subsequently reacting with compound (19), as illustrated in Scheme 10.

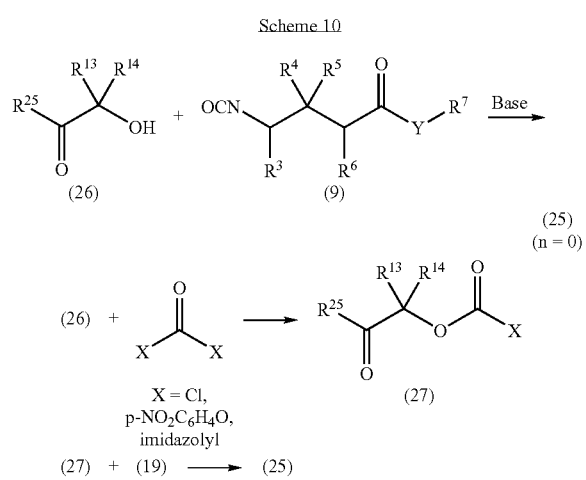

Alternatively ketocarbamate (25) can be prepared in a stepwise manner via the α-amino acid carbamate (28) as illustrated in Scheme 11, following the coupling methodologies described above.

Note that one method for preparation of isocyanate derivatives of GABA analogs (i.e., compounds (9)) used in Scheme 10 above begins with the appropriate six-membered anhydride (29) as illustrated in Scheme 12. The anhydride ring is opened by reaction with an alcohol or thiol nucleophile to afford carboxylic acid (30). This compound is converted to the intermediate acyl azide in either a 2-step sequence (i.e., first activation of the carboxyl group as a mixed anhydride, acyl halide or synthetic equivalent and then displacement with azide) or directly (e.g., by treatment with $Ph_2P(O)N_3$). Curtius rearrangement of the acyl azide intermediate by thermolysis in an appropriate solvent (e.g., toluene) at a temperature between 0° C. to 120° C. affords isocyanate (9). Optionally, the isocyanate is not isolated but rather is generated in situ and quenched by reaction with α-hydroxyketone (26) to afford the desired product (25).

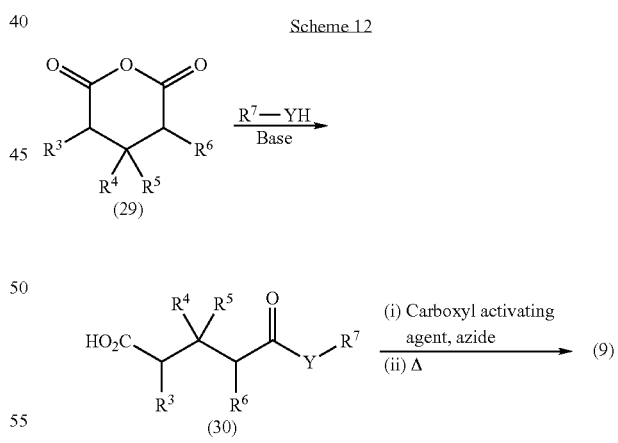

One method for synthesis of oxodioxolenylmethyl carbamate prodrugs (36) is disclosed in Scheme 13. Hydroxyketone (31) is treated with phosgene or carbonyldiimidazole in the presence of base to yield cyclic carbonate (32). Free radical bromination with N-bromosuccinimide and azoisobutryonitrile provides bromide (33), which is converted to alcohol (34). Alcohol (34) is transformed to dicarbonate (35) by reaction with 4-nitrophenyl chloroformate, which is then reacted with GABA analog derivatives (19) to provide prodrugs (36). Alternatively, reaction of compound (34) with isocyanate (9) provides compound (36), where n is 0.

Scheme 13

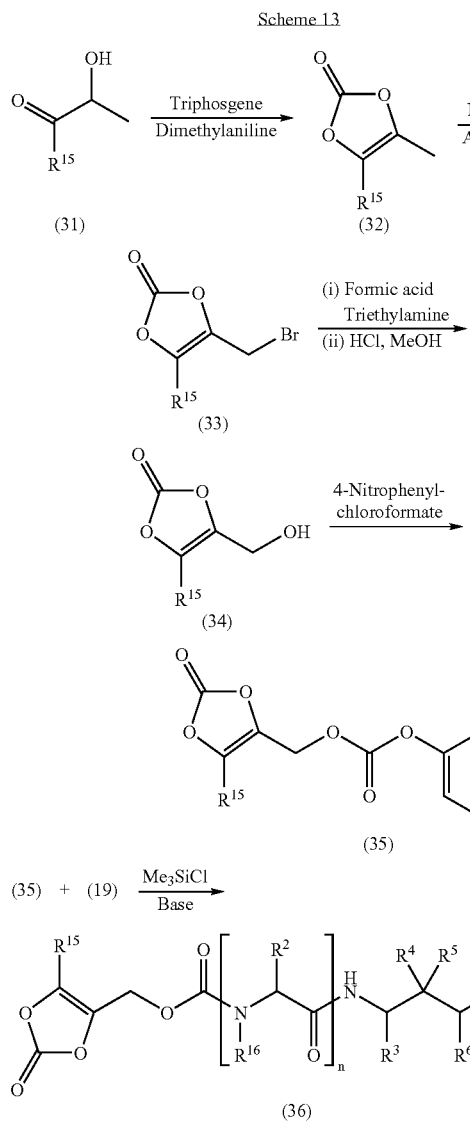

Prodrugs (41) may be synthesized by the method disclosed in Scheme 14. Carboxylic acid (37) is coupled to alcohol (38) (e.g., dicylohexylcarbodiimide and pyridine) to provide ester (39). Ester (39) is converted to activated carbonate (40) by reaction with 4-nitrophenyl chloroformate, which is then reacted with GABA analog derivative (19) to provide prodrug (41).

Scheme 14

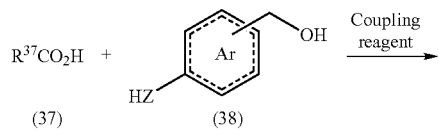

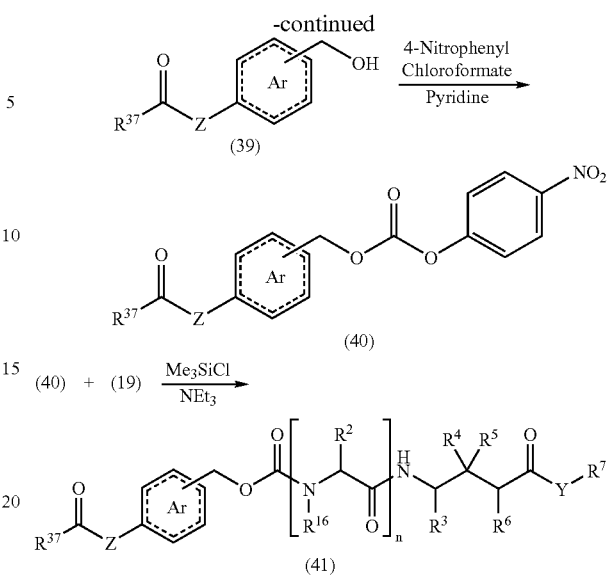

Enamine prodrugs such as (43) may be synthesized simply by reacting activated carbonyl compounds (42) with GABA analog derivatives (19) (where $R^{16}$=H), optionally in the presence of a secondary amine as catalyst, under dehydrating conditions as shown in Scheme 15.

Scheme 15

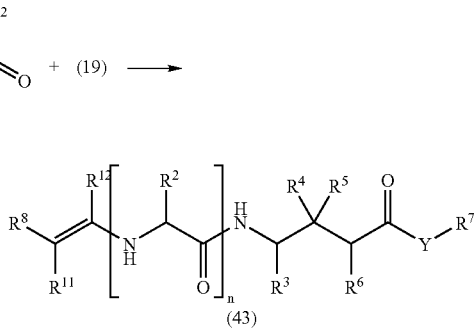

Compounds (III) may be synthesized by the route illustrated in Scheme 16. Reaction of GABA analog (23) with an α-activated ester derivative (44) provides amino ester (45). The amino group of (45) is blocked by acylation to yield (46) (e.g., using the methods described above) and the free acid is esterified under standard conditions to yield the diester (47). Dieckman condensation followed by decarboxylation yields ketone (48). Peroxy acid oxidation then provides lactone (III).

Scheme 16

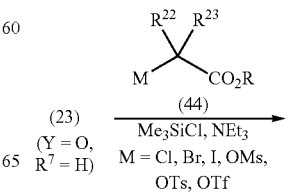

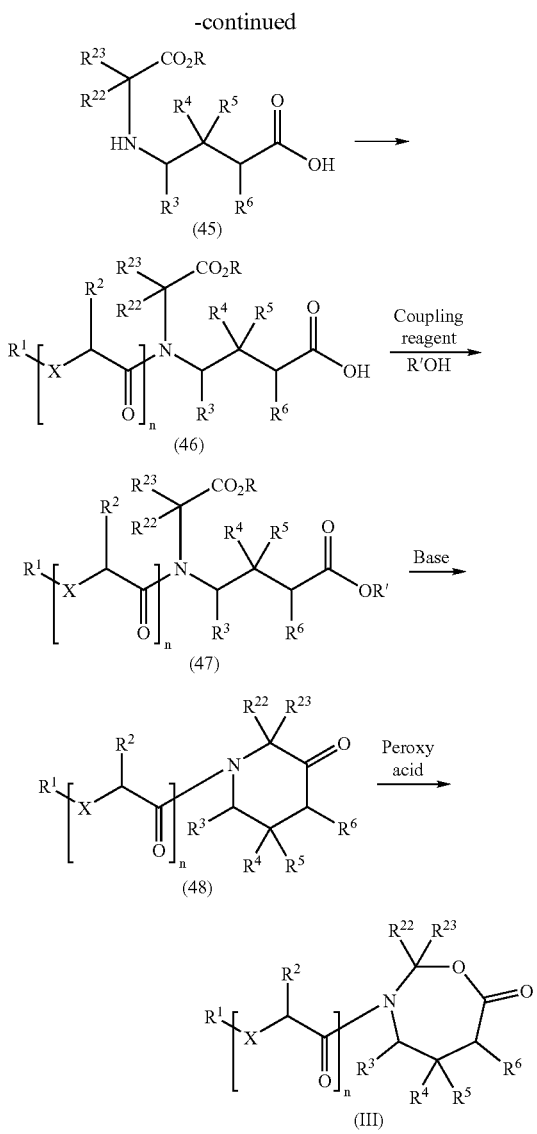

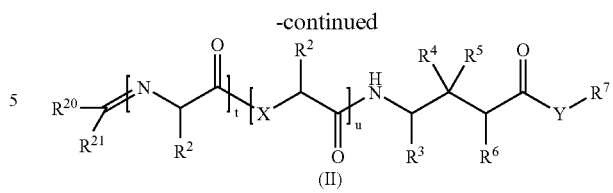

Phosphorus prodrugs may be synthesized by conventional methods known in the art. Similarly, prodrugs with S—N bond may be synthesized by using procedures described in the art.

4.4 Therapeutic Uses of the Compounds of the Invention

In accordance with the invention, a compound and/or composition of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. Further, in certain embodiments, the compounds and/or compositions of the invention are administered to a patient, preferably a human, as a preventative measure against various diseases or disorders. Thus, the compounds and/or compositions of the invention may be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome. Accordingly, the compounds and/or compositions of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or compositions of the invention in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,169; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., Imine prodrugs (II) may be synthesized as depicted in Scheme 17 by treating ketones or ketone equivalents (49) with GABA analog derivatives (50) under dehydrating conditions.

Scheme 17

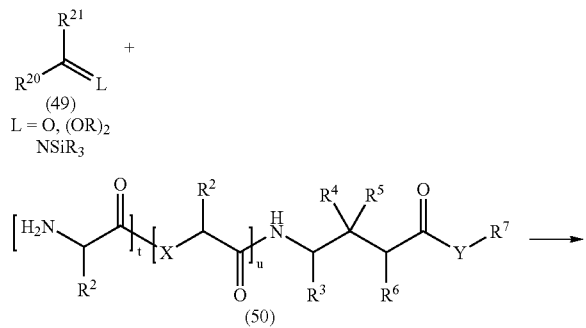

International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bellioti et al., International Publication No. WO 00/31020; Bryans et al., International Publication No. WO 00/50027; and Bryans et al, International Publication No. WO 02/00209).

The suitability of the compounds of the invention and/or compositions thereof in treating or preventing various diseases or disorders such as epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be assayed by methods described in the art (see references above). Accordingly, it is well with the capability of those of skill in the art to assay and use the compounds of the invention and/or compositions thereof to treat or prevent the above diseases or disorders.

4.5 Therapeutic/Prophylactic Administration

The compounds and/or compositions of the invention may be advantageously used in human medicine. As previously described in Section 4.4 above, compounds and/or compositions of the invention are useful for the treatment or prevention of epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome.

When used to treat or prevent the above disease or disorders compounds and/or compositions of the invention may be administered or applied singly, in combination with other agents. The compounds and/or compositions of the invention may also be administered or applied singly, in combination with other pharmaceutically active agents, including other compounds of the invention.

The current invention provides methods of treatment and prophylaxis by administration to a patient of a therapeutically effective amount of a composition or compound of the invention. The patient may be an animal, is more preferably a mammal, and most preferably a human.

The present compounds and/or compositions of the invention, which comprise one or more compounds of the invention, are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In particularly preferred embodiments, the compounds and/or compositions of the invention can be delivered via sustained release systems, preferably oral sustained release systems. In one embodiment, a pump may be used (see Langer, supra; Sefton, 1987, *CRC Crit Ref Biomed Eng.* 14:201; Saudek et al., 1989, *N. Engl. J. Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.*, 1984, 5(3) 1–9). Factors affecting drug release are well known to the skilled artisan and have been described in the art (Bamba et al., *Int. J. Pharm.*, 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.*, 2000, 26:695–708). In a preferred embodiment, OROS™ osmotic devices are used for oral sustained release delivery devices (Thecuwes et al., U.S. Pat. No. 3,845,770; Theeuwes et al., U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115–138 (1984)). Other controlled-release systems discussed in Langer, 1990, *Science* 249:1527–1533 may also be used.

The compounds and/or compositions of the invention preferably provide GABA analogs (e.g., gabapentin and pregablin) upon in vivo administration to a patient. While not wishing to bound by theory, the promoiety or promoieties of the compounds and/or compositions of the invention may be cleaved either chemically and/or enzymatically. One or more enzymes present in the stomach, intestinal lumen, intestinal tissue, blood, liver, brain or any other suitable tissue of a mammal may enzymatically cleave the promoicty or promoicties of the compounds and/or compositions of the invention. The mechanism of cleavage is not important to the current invention. Preferably, GABA analogs formed by cleavage of prodrugs from the compounds of the invention do not contain substantial quantities of lactam contaminant (preferably, less than 0.5% by weight, more preferably, less than 0.2% by weight, most preferably less than 0.1% by weight). The extent of release of lactam contaminant from the prodrugs of this invention may be assessed using the standard in vitro analytical methods.

While not wishing to bound by theory, the promoiety or promoieties of the compounds and/or compositions of the invention may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety or promoieties of the compounds of the invention are cleaved prior to absorption by the gastrointestinal tract, the resulting GABA analogs may be absorbed into the systemic circulation conventionally (e.g. via the large neutral amino acid transporter located in the small intestine). If the promoiety or promoieties of the compounds of the invention are cleaved after absorption by the gastrointestinal tract, these GABA analog prodrugs may have the opportunity to be absorbed into the systemic circulation either by passive diffusion, active transport or by both passive and active processes.

If the promoiety or promoieties of the compounds of the invention are cleaved after absorption by the gastrointestinal tract, these GABA analog prodrugs may have the opportunity to be absorbed into the systemic circulation from the large intestine. In this situation, the compounds and/or compositions of the invention are preferably administered as sustained release systems. In a preferred embodiment, the compounds and/or compositions of the invention are delivered by oral sustained release administration. Preferably, in this embodiment, the compounds and/or compositions of the invention are administered twice per day (more preferably, once per day).

4.6 Compositions of the Invention

The present compositions contain a therapeutically effective amount of one or more compounds of the invention, preferably in purified form, together with a suitable amount of a pharmaceutically acceptable vehicle, to provide the form for proper administration to a patient. When administered to a patient, the compounds of the invention and pharmaceutically acceptable vehicles are preferably sterile. Water is a preferred vehicle when a compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

In one embodiment, the compositions of the invention are free of lactam side products formed by intramolecular cyclization. In a preferred embodiment, the compositions of the invention are stable to extended storage (preferably, greater than one year) without substantial lactam formation (preferably, less than 0.5% lactam by weight, more preferably, less than 0.2% lactam by weight, most preferably, less than 0.1% lactam by weight).

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No.

5,112,598; Biesalski, U.S. Pat. No. 5,556,611). A compound of the invention may also be formulated in rectal or vaginal compositions such as suppositories or retention enemas, e.g., containing conventional suppository bases such as cocoa butter or other glycerides. In addition to the formulations described previously, a compound of the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

4.7 Methods of Use And Doses

A compound of the invention, or compositions thereof, will generally be used in an amount effective to achieve the intended purpose. For use to treat or prevent diseases or disorders such as epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders or ethanol withdrawal syndrome the compounds of the invention or compositions thereof, are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the parent GABA analog drug, but are generally about 0.001 mg to about 200 mg of a compound of the invention per kilogram body weight. When the GABA analog is gabapentin, typical daily doses of the parent drug in adult patients are 900 mg/day to 3600 mg/day and the dose of gabapentin prodrug may be adjusted to provide an equivalent molar quantity of gabapentin. Other GABA analogs may be more potent than gabapentin (e.g., pregabalin), and lower doses may be appropriate for both the parent drug and any prodrug (measured on an equivalent molar basis). Dosage ranges may be readily determined by methods known to the skilled artisan.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

4.8. Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent.

5. EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | | |
|---|---|---|
| AIBN | = | 2,2'-azobis(isobutyronitrile) |
| Atm | = | atmosphere |
| Boc | = | tert-butyloxycarbonyl |
| Cbz | = | carbobenzyloxy |
| CPM | = | counts per minute |
| DCC | = | dicyclohexylcarbodiimide |
| DMAP | = | 4-N,N-dimethylaminopyridine |
| DMEM | = | Dulbecco's minimun eagle medium |
| DMF | = | N,N-dimethylformamide |
| DMSO | = | dimethylsulfoxide |

-continued

| | | |
|---|---|---|
| Fmoc | = | 9-fluorenylmethyloxycarbonyl |
| g | = | gram |
| h | = | hour |
| HBSS | = | Hank's buffered saline solution |
| L | = | liter |
| LC/MS | = | liquid chromatography/mass spectroscopy |
| M | = | molar |
| min | = | minute |
| mL | = | milliliter |
| mmol | = | millimoles |
| NBS | = | N-bromosuccinimide |
| NHS | = | N-hydroxysuccinimide |
| PBS | = | phosphate buffered saline |
| THF | = | tetrahydrofuran |
| TFA | = | trifluoroacetic acid |
| TMS | = | trimethylsilyl |
| μL | = | microliter |
| μM | = | micromolar |
| v/v | = | volume to volume |

Example 1

1-{[(α-Pivaloyloxymethoxy)carbonyl]aminomethyl}-1-Cyclohexane Acetic Acid (51)

Step A: Chloromethyl p-Nitrophenyl Carbonate (52)

p-Nitrophenol (100 g, 0.72 moles) was dissolved in anhydrous tetrahydrofuran (3 L) and stirred vigorously. To this solution was added chloromethyl chloroformate (70 mL, 0.79 moles) at room temperature followed by triethylamine (110 mL). After stirring for 1 hour, the reaction mixture was filtered and the filtrate was concentrated and then diluted with ethyl acetate (1 L). The organic solution was washed with 10% potassium carbonate (3×500 mL) and 1N HCl (2×300 mL), brine (2×300 mL) and dried over anhydrous sodium sulfate. Removal of the solvent gave 157 g (95%) of the title compound (52) as a solid. The compound was unstable to LC-MS. $^1$H NMR (CDCl$_3$, 400 MHz): 5.86 (s, 2H), 7.44 (d, J=9 Hz, 2H), 8.33 (d, J=9 Hz, 2H).

Step B: Iodomethyl p-Nitrophenyl Carbonate (53)

Chloromethyl p-nitrophenyl carbonate (52) (100 g, 0.43 moles), sodium iodide (228 g, 1.30 moles) and 50 g of dried molecular sieves (4 Å) were added to 2 L of acetone under nitrogen with mechanical stirring. The resulting mixture was stirred at 40° C. for 5 hours (monitored by $^1$H NMR). Upon completion, the solid materials were removed by filtration and the solvent was removed under reduced pressure. The residue was redissolved in dichloromethane (1 L) and washed twice with saturated aqueous sodium carbonate (300 mL) followed by water (300 mL). The organic layer was separated and dried over anhydrous sodium sulfate. Removal of solvent gave 123.6 g (89%) of the title compound (53) as a solid upon standing. The compound was found to be unstable to LC-MS. $^1$H NMR (CDCl$_3$, 400 MHz): 6.06 (s, 2H), 7.42 (d, J=9 Hz, 2H), 8.30 (d, J=9 Hz, 2H). $^{13}$C NMR (CDCl$_3$, 100 MHz): 155.1, 151.0, 146.0, 125.8, 125.7, 121.9, 33.5.

Step C: Silver Pivalate (54)

Pivalic acid (50 g, 0.49 moles) was dissolved in acetonitrile (1.3 L) followed by addition of silver oxide (70 g, 0.29 moles) with vigorous stirring. Then, 660 mL of water was added under nitrogen. The resulting suspension was stirred at 70° C. in dark for 1 hour. After filtration through a pad of Celite, removal of the solvent gave 86 g (82%) of the title compound (54) as a pale white solid, which was used in the next reaction without further purification.

Other silver salts described in this application are prepared following similar procedures.

Step D: p-Nitrophenyl Pivaloyloxymethyl Carbonate (55)

To a solution of iodomethyl p-nitrophenyl carbonate (53) (62 g, 0.19 moles) in anhydrous toluene (1 L) was added silver pivalate (80 g, 0.38 moles). After stirring at 55° C. under nitrogen for 3 h, the reaction mixture was allowed to cool to room temperature and filtered through a pad of Celite. The filtrate was washed with 10% potassium carbonate (500 mL). Removal of the solvent yielded 43 g (75%) of the title compound (55) as a yellow oil. $^1$H NMR (CDCl$_3$, 400 MHz): 1.25 (s, 9H), 5.88 (s, 2H), 7.40 (d, J=9 Hz, 2H), 8.29 (d, J=9 Hz, 2H). $^{13}$C NMR (CDCl$_3$, 100 MHz): 177.0, 155.3, 151.6, 145.8, 125.6, 121.9, 83.1, 39.1, 27.0.

Step E: 1-{[(α-Pivaloyloxymethoxy)carbonyl]aminomethyl}-1-Cyclohexane Acetic Acid (51)

Gabapentin free base (24 g, 0.14 moles) was slurried in anhydrous dichloromethane (100 mL) and then treated with chlorotrimethylsilane (18.6 mL, 0.28 moles) and triethylamine (10 mL, 0.15 moles), respectively. The resulting suspension was warmed with stirring until complete dissolution of any solid was achieved. The above gabapentin solution was added via an equalizing addition funnel to a gently refluxed and mechanically stirred solution of p-nitrophenyl pivaloyloxymethyl carbonate (55) (20 g, 67 mmol) and triethylamine (10 mL, 0.15 moles) in dichloromethane (100 mL) under nitrogen. The resulting yellow solution was stirred for 1.5 hours. Upon completion (monitored by ninhydrin stain), the mixture was filtered and the filtrate was concentrated. The residue was dissolved in ethyl acetate (500 mL) and washed with 1N HCl (3×100 mL), brine (2×100 mL) and dried over anhydrous sodium sulfate. After removing the solvent, the crude product was dissolved in ethanol (300 mL) and then 1 g of 5% Pd/C was added. The resulting mixture was shaken under 50 psi hydrogen atmosphere for 15 minutes and then filtered through a pad of Celite. After concentration, the residue was dissolved in ethyl acetate, washed with 5% H$_2$SO$_4$ and dried over anhydrous sodium sulfate. After removing the solvent under reduced pressure, the residue was purified by chromatography on silica gel (4:1 hexanes:ethyl acetate) to afford 15 g (68%) of the title compound (51) as a solid. M.p.: 79–81° C.; $^1$H NMR (CDCl$_3$, 400 MHz): 1.21 (s, 9H), 1.3–1.5 (m, 10H), 2.32 (s, 2H), 3.26 (s, 2H), 5.33 (m, 1H), 5.73 (s, 2H). $^{13}$C NMR (CDCl$_3$, 400 MHz): 21.7, 26.2, 27.3, 34.3, 38.2, 39.2, 80.6, 155.9, 176.8, 178.0. MS (ESI) m/z 328.36 (M−H)$^-$, 330.32 (M+H)$^+$, 352.33 (M+Na)$^+$.

Example 2

1-{[(α-Acetoxyethoxy)carbonyl]aminomethyl}-1-Cyclohexane Acetic Acid (56)

Step A: 1-Chloroethyl-p-Nitrophenyl Carbonate (57)

To an ice cold reaction mixture containing p-nitrophenol (1.39 g, 10 mmol) and pyridine (0.81 g, 10 mmol) in dichloromethane (60 mL) was added 1-chloroethyl chloroformate (1.2 mL, 11 mmol). The mixture was stirred at 0° C. for 30 min and then at room temperature for 1 hour. After removing the solvent under reduced pressure, the residue was dissolved in ether, washed with water, 10% citric acid and water. The ether layer was dried over $Na_2SO_4$ and evaporated under reduced pressure to give 2.4 g (97%) of the title compound (57) as an off-white solid. $^1$H NMR ($CDCl_3$): 1.93 (d, 3H), 6.55 (q, 1H), 7.42 (d, 2H), 8.28 (d, 2H).

Step B: α-Acetoxyethyl-p-Nitrophenyl Carbonate (58)

A mixture of 1-chloroethyl-p-nitrophenyl carbonate (57) (0.5 g, 2 mmol) and mercuric acetate (1.5 g, 4.4 mmol) in acetic acid (15 mL) was stirred at room temperature for 24 hours. After removal of acetic acid under reduced pressure, the residue was dissolved in ether and washed with water, 0.5% (v/v) aqueous $NaHCO_3$, and water. The ether layer was dried over $Na_2SO_4$, and concentrated to dryness. Chromatography of the resulting residue on silica gel, (hexanes: ethyl acetate (95:5)) gave 0.45 g (84%) of the title compound (58). $^1$H NMR ($CDCl_3$, 400 MHz): 1.55 (d, J=5.6 Hz, 3H), 2.07 (s, 3H), 6.78 (q, J=5.6 Hz, 1H), 7.36 (d, J=9.6 Hz, 2H), 8.22 (d, J=9.6 Hz, 2H).

Step C: 1-{[(α-Acetoxyethoxy)carbonyl]aminomethyl}-1-Cyclohexane Acetic Acid (56)

To a mixture containing gabapentin (633 mg, 3.7 mmol) and triethylamine (1.03 mL, 7.4 mmol) in dichloromethane (20 mL) was added trimethylchlorosilane (0.93 mL, 7.4 mmol) and the mixture was stirred until a clear solution was formed. A solution containing α-acetoxyethyl-p-nitrophenyl carbonate (58) (1 g, 3.7 mmol) in dichloromethane (10 mL) was then added and the resulting mixture was stirred for 30 minutes. The reaction mixture was washed with 10% citric acid (20 mL) and the organic layer was separated. The aqueous layer was further extracted with ether (3×10 mL) and the combined organic extracts were dried over $MgSO_4$. After filtration, the organic solvent was removed under reduced pressure. Chromatography of the resulting residue on silica gel, (hexanes:ethyl acetate (4:1)), gave 700 mg (63%) of the title compound (56). $^1$H NMR ($CDCl_3$, 400 MHz): 1.27–1.60 (m, 10H), 1.55 (d, 3H), 2.08 (s, 3H), 2.38 (s, 2H), 3.25 (m, 2H), 5.31 (t, 1H), 6.81 (q, 1H). MS (ESI) m/z 302.22 $(M+H)^+$. The acid form was quantitatively converted to the corresponding sodium salt by dissolution in water (5 mL), addition of an equimolar quantity of 0.5 N $NaHCO_3$, followed by lyophilization.

Example 3

1-{[(α-Benzoyloxybenzyloxy)carbonyl]aminomethyl}-1-Cyclohexane Acetic Acid (59)

Step A: p-Nitrophenyl α-Benzoylbenzylcarbonate (60)

To a solution of benzoin (2.0 g, 9.4 mmol) in 60 mL of $CH_2Cl_2$ was added DMAP (1.21 g, 9.9 mmol) and p-nitrophenyl-chloroformate (1.99 g, 9.9 mmol), respectively, at room temperature. After stirring for 3 hours at room temperature, the reaction was quenched with water and extracted with ethyl acetate/hexane (2×100 mL). The combined organic extracts were dried over anhydrous sodium sulfate. Removal of the solvent under reduced pressure afforded the title compound (60), which was used in the next reaction without purification.

Step B: 1-{[(α-Benzoylbenzyloxy)carbonyl]aminomethyl}-1-Cyclohexane Acetic Acid (61)

To a suspension of gabapentin (1.70 g, 9.9 mmol) in $CH_2Cl_2$ at 0° C. was added triethylamine (2.76 mL, 19.8 mmol) and TMSCl (2.51 mL, 19.8 mmol). The reaction was then stirred for 30 minutes at room temperature. To this mixture was added compound (60) (prepared above in Step A) in $CH_2Cl_2$ and the resulting mixture was stirred at room temperature for 5 hours. The reaction mixture was diluted with dichloromethane, washed with brine and the organic phase was dried over $Na_2SO_4$. After removing the solvent under reduced pressure, the residue was purified by chromatography on silica gel, eluting with 5% methanol in $CH_2Cl_2$, to give 3.78 g (90% over two steps) of the title compound (61). $^1$H NMR ($CDCl_3$, 400 MHz): δ 1.48–1.35 (m, 10H), 2.30 (s, 2H), 3.24 (d, J=7.2 Hz, 2H), 5.58 (t, J=6.8 Hz, 1H), 6.85 (s, 1H), 7.50–7.33 (m, 8H), 7.93 (d, J=7.2 Hz, 2H).

Step C: 1-{[(α-Benzoyloxybenzyloxy)carbonyl]aminomethyl}-1-Cyclohexane Acetic Acid (59)

To a solution of 1-{[(α-benzoylbenzyloxy)carbonyl]aminomethyl}-1-cyclohexane acetic acid (61) (1.89 g, 4.6 mmol) in 40 mL of $CH_2Cl_2$ was added 77% mCPBA (2.07 g, 9.2 mmol) and $NaHCO_3$ (0.78 g, 9.2 mmol), respectively, at room temperature and the resulting mixture was stirred at room temperature overnight. The reaction mixture was acidified with 10% citric acid and extracted with $CH_2Cl_2$. The organic extract was washed with brine and dried over $Na_2SO_4$. After removing the solvent under reduced pressure, the residue was purified by reverse phase preparative HPLC (acetonitrile-water, 0.1% formic acid) to afford 960 mg (49%) of the title compound (59). $^1$H NMR ($CDCl_3$, 400 MHz): δ 1.58–1.35 (m, 10H), 2.34 (s, 2H), 3.26 (dd, J=6.8, 0.8 Hz, 2H), 5.38 (t, J=6.8 Hz, 1H), 7.46–7.26 (m, 5H), 7.63–7.55 (m, 3H), 7.89 (s, 1H), 8.08 (dd, J=8.8, 1.2 Hz, 2H).

Example 4

1-{[(α-Acetoxybenzyloxy)carbonyl]aminomethyl}-1-Cyclohexane Acetic Acid (62)

Following the procedure of Example 3, and substituting 1-hydroxy-1-phenyl-propan-2-one for benzoin, provided 300 mg of the title compound (62). $^1$H NMR ($CDCl_3$, 400 MHz): δ 1.41 (m, 10H), 2.19 (s, 3H), 2.33 (s, 2H), 3.27 (dd, J=6.6, 1.6 Hz, 2H), 5.36 (t, J=6.6 Hz, 1H), 7.40 (m, 3H), 7.52 (m, 2H), 7.63 (s, 1H).

Example 5

1-{[(α-Benzoyloxyethoxy)carbonyl]aminomethyl}-1-Cyclohexane Acetic Acid (63)

Following the procedure of Example 3, and substituting 2-hydroxy-1-phenyl-1-propanone for benzoin, provided 5 mg of the title compound (63). $^1$H NMR ($CDCl_3$, 400 MHz): δ 1.44–1.36 (m, 10H), 1.62 (d, J=5.6 Hz, 3H), 2.34 (s, 2H), 3.24 (d, J=6.8 Hz, 2H), 5.28 (t, J=6.8 Hz, 1H), 7.06 (q, J=5.6 Hz, 1H), 7.44 (m, 2H), 7.56 (m, 1H), 8.03 (dd, J=8.4, 1.6 Hz, 2H).

Example 6

1-{[(1-Benzoyloxy-2-phenylethoxy)carbonyl]aminomethyl}-1-Cyclohexane Acetic Acid (64)

Step A: 2-Phenyl-[1,3]-dithiane (65)

To a solution of benzaldehyde (10.6 g, 100 mmol) and 1,3-propane dithiol in $CH_2Cl_2$ (150 mL) at room temperature was dropwise added $BF_3.Et_2O$ (6.3 mL, 50 mmol) and the resulting mixture was stirred at room temperature for 2 hours. The reaction mixture was then diluted with $CH_2Cl_2$, filtered and the filtrate washed with brine, saturated $NaHCO_3$, brine and dried over $Na_2SO_4$. The solvent was removed under reduced pressure to afford a white solid, which was recrystallized from a 1:1 mixture of ether and hexane to afford 17.0 g (87%) of the title compound (65) as white crystalline needles. $^1H$ NMR ($CDCl_3$, 400 MHz): δ 1.91 (m, 1H), 2.14 (m, 1H), 2.89 (m, 2H), 3.04 (m, 2H), 5.16 (s, 1H), 7.35–7.28 (m, 3H), 7.46 (m, 2H).

Step B: 2-Phenyl-1-(2-phenyl-[1,3]-dithian-2-yl)-ethanol (66)

To a solution of 2-phenyl-[1,3]-dithiane (65) (4.0 g, 20.4 mmol) in THF at −30° C. was added a 1.6 M solution of n-butyllithium in THF (15.3 mL, 24.4 mmol). After stirring for 30 minutes at −30° C., a solution of phenylacetylaldehyde (2.45 g, 20.4 mmol) in tetrahydrofuran was added dropwise at −30° C. The resulting reaction mixture was stirred for another hour at 0° C. The reaction was quenched with saturated $NH_4Cl$ solution and extracted with ethyl acetate. The combined organic extracts were washed with saturated $NH_4Cl$ solution, brine and dried over $Na_2SO_4$. After filtrating and concentrating, the crude product was purified by flash chromatography on silica gel, (25% ethyl acetate in hexanes), to afford 2.63 g (71%) of the title compound (66). $^1H$ NMR ($CDCl_3$, 400 MHz): δ 1.97 (m, 2H), 2.23 (dd, J=4.0, 1.2 Hz, 1H), 2.43 (dd, J=13.6, 10.2 Hz, 1H), 2.77 (m, 4H), 3.02 (d, J=13.6 Hz, 1H), 4.07 (m, 1H), 7.44–7.13 (m, 8H), 8.02 (dd, J=8.4, 1.4 Hz, 2H).

Step C: 2-Hydroxy-1,3-diphenyl-propan-1-one (67)

To a solution of 2-phenyl-1-(2-phenyl-[1,3]-dithian-2-yl)-ethanol (66) (2.50 g, 7.9 mmol) in 100 mL of a 9:1 mixture of acetonitrile and water was added mercuric perchlorate hydrate (4.1 g, 10.3 mmol). The resulting mixture was stirred at room temperature for 5 minutes and thin layer chromatography indicated that the reaction was completed. The mixture was diluted with ethyl acetate, filtered through a pad of Celite and the filtrate was washed with saturated $NaHCO_3$, brine and dried over $Na_2SO_4$. The solvent was removed under reduced pressure and the crude product was purified by flash chromatography on silica gel, (20% ethyl acetate in hexanes) to afford 1.32 g (74%) of the title compound (67). $^1H$ NMR ($CDCl_3$, 400 MHz): δ 2.90 (dd, J=14.4, 7.0 Hz, 1H), 3.20 (dd, J=14.4, 4.0 Hz, 1H), 3.70 (d, J=6.8 Hz, 1H), 5.35 (m, 1H), 7.28–7.11 (m, 5H), 7.53 (m, 2H), 7.65 (m, 1H), 7.93 (d, J=7.2 Hz, 2H).

Step D: 1-{[(1-Benzoyloxy-2-phenylethoxy)carbonyl]aminomethyl}-1-Cyclohexane Acetic Acid (64)

Following the procedure of Example 3, and substituting 2-hydroxy-1,3-diphenyl-propan-1-one for benzoin, provided 181 mg of the title compound (64). $^1H$ NMR ($CDCl_3$, 400 MHz): δ 1.45–1.29 (m, 10H), 2.24 (d, J=13.6 Hz, 1H), 2.28 (d, J=13.6 Hz, 1H), 3.22 (m, 4H), 5.26 (t, J=6.6 Hz, 1H), 7.16 (t, J=5.6 Hz, 1H), 7.33–7.25 (m, 5H), 7.40 (m, 2H), 7.57 (m, 1H), 8.02 (m, 2H).

Example 7

1-{[(1-(3-Methylbutanoyloxy)-2-phenylethoxy)carbonyl]aminomethyl}-1-Cyclohexane Acetic Acid (68)

Following the procedure of Example 6 and substituting 3-methylbutyraldehyde for benzaldehyde in Step A, provided 95 mg of the title compound (68). $^1H$ NMR ($CDCl_3$, 400 MHz): δ 0.88–0.90 (m, 6H), 1.16–1.29 (m, 10H), 2.06 (m, 1H), 2.16 (m, 2H), 2.26 (m, 2H), 3.08 (d, J=6.8 Hz, 2H), 3.19 (m, 2H), 5.22 (t, J=6.8 Hz, 1H), 6.93(t, J=6 Hz, 1H), 7.31–7.23 (m, 5H).

Example 8

1-{[(α-Benzoyloxybutoxy)carbonyl]aminomethyl}-1-Cyclohexane Acetic Acid (69)

Following the procedure of Example 6 and substituting butyraldehyde for phenylacetaldehyde in Step B, provided 240 mg of the title compound (69). $^1H$ NMR ($CDCl_3$, 400 MHz): δ 0.99 (t, J=7.6 Hz, 3H), 1.52–1.38 (m, 12H), 1.89 (m, 2H), 2.31 (s, 2H), 3.24 (m, 2H), 5.34 (t, J=6.6 Hz, 1H), 6.70 (t, J=5.6 Hz, 1H), 7.42 (m, 2H), 7.56 (m, 1H), 8.04 (m, 2H).

Example 9

1-{[(α-Acetoxybutoxy)carbonyl]aminomethyl}-1-Cyclohexane Acetic Acid (70)

Following the procedure of Example 6, and substituting acetaldehyde for benzaldehyde in Step A and substituting butyraldehyde for phenylacetaldehyde in Step B respectively, provided 42 mg of the title compound (70). $^1H$ NMR ($CD_3OD$, 400 MHz): δ 0.95 (m, 3H), 1.52–1.31 (m, 12H), 1.72 (m, 2H), 2.02 (s, 3H), 2.27 (s, 2H), 3.20 (s, 2H), 6.67 (t, J=5.6 Hz, 1H).

Example 10

1-{[(α-Butanoyloxybutoxy)carbonyl]aminomethyl}-1-Cyclohexane Acetic Acid (71)

Following the procedure of Example 3, and substituting butyroin for benzoin, provided 210 mg of the title compound (71). $^1H$ NMR ($CDCl_3$, 400 MHz); δ 0.93 (m, 6H), 1.37–1.76 (m, 16H), 2.30 (m, 4H), 3.23 (m, 2H), 5.25 (broad triplet, 1H), 6.73 (m, 1H). MS (ESI) m/z 356.45 (M−H)$^+$.

Example 11

1-{[(α-Propanoyloxyethoxy)carbonyl]aminomethyl}-1-Cyclohexane Acetic Acid (72)

Step A: 1-Iodoethyl-p-Nitrophenyl Carbonate (73)

A mixture of 1-chloroethyl-p-nitrophenyl carbonate (0.5 g, 2 mmol) and NaI (0.6 g, 4 mmol) in dry acetone was stirred for 3 hours at 40° C. After filtration, the filtrate was concentrated under reduced pressure to afford 480 mg (72%)

of the title compound (73), which was used in the next reaction without further purification.

Step B: α-Propanoyloxyethyl-p-Nitrophenyl Carbonate (74)

A mixture of 1-iodoethyl-p-nitrophenyl carbonate (73) (0.51 g, 1.5 mmol) and silver propionate (0.54 g, 3 mmol) in toluene (20 mL) was stirred at 50° C. for 24 hours. The reaction mixture was filtered to remove solids and the filtrate concentrated under reduced pressure. Chromatography of the resulting residue on silica gel, (20% $CH_2Cl_2$/hexanes and then 40% $CH_2Cl_2$/hexanes), gave 0.39 g (92%) of the title compound (74). $^1$H NMR ($CDCl_3$, 400 MHz): 1.16 (t, J=7.6 Hz, 3H), 1.61 (d, J=5.6 Hz, 3H), 2.41 (q, J=7.6 Hz, 2H), 6.84 (q, 1H, J=5.6 Hz), 7.39 (d, J=9.2 Hz, 2H), 8.28 (d, J=9.2 Hz, 2H).

Step C: 1-{[(α-Propanoyloxyethoxy)carbonyl]aminomethyl}-1-Cyclohexane Acetic Acid (72)

To a mixture of gabapentin (160 mg, 2.76 mmol) and triethylamine (0.77 mL, 5.5 mmol) in dichloromethane (30 mL) was added trimethylchlorosilane (0.71 mL, 5.5 mmol) and the resulting mixture was stirred until a clear solution was formed. To the above solution was added a solution of α-propanoyloxyethyl-p-nitrophenyl carbonate (74) (0.39 g, 1.4 mmol) in dichloromethane (10 mL). After stirring for 30 minutes the reaction mixture was washed with 10% citric acid (20 mL) and the organic layer was separated. The aqueous layer was further extracted with ether (3×10 mL) and the combined organic extracts were dried over $MgSO_4$. After removing the solvent under reduced pressure, the residue was purified by reverse phase preparative HPLC (acetonitrile, water, 1% formic acid) to afford 190 mg (44%) of the title compound (72). $^1$H NMR ($CD_3OD$, 400 MHz): 1.09 (t, J=7.6 Hz, 3H), 1.36–1.54 (m, 10H), 1.44 (d, J=5.6 Hz, 3H), 2.28 (s, 2H), 2.31 (q, J=7.6 Hz, 2H), 3.22 (s, 2H), 6.67 (q, J=5.6 Hz, 1H). MS (ESI) m/z 316.25 $(M+H)^+$.

Example 12

1-{[(α-Butanoyloxyethoxy)carbonyl]aminomethyl}-1-Cyclohexane Acetic Acid (75)

Step A: α-Butanoyloxyethyl-p-Nitrophenyl Carbonate (76)

A mixture of 1-iodoethyl-p-nitrophenyl carbonate (73) (1.5 g, 4.5 mmol) and silver butyrate (1.3 g, 6.7 mmol) in toluene (40 mL) was stirred at 90° C. in an oil bath for 24 h. The reaction mixture was filtered and the filtrate was concentrated under reduced pressure. Chromatography of the resulting residue on silica gel, (20% $CH_2Cl_2$/hexanes and then 40% $CH_2Cl_2$/hexanes), gave 0.46 g (36%) of the title compound (76). $^1$H NMR ($CDCl_3$, 400 MHz): 0.95 (t, J=7.6 Hz, 3H), 1.61 (d, J=5.6 Hz, 3H), 1.67 (m. 2H), 2.41 (t, J=7.6 Hz, 2H), 6.84 (q, 1H, J=5.6 Hz), 7.39 (d, J=9.2 Hz, 2H), 8.28 (d, J=9.2 Hz, 2H). MS (ESI) m/z 298.28 $(M+H)^+$.

Step B: 1-{[(α-Butanoyloxyethoxy)carbonyl]aminomethyl}-1-Cyclohexane Acetic Acid (75)

To a mixture containing gabapentin (530 mg, 3.1 mmol) and triethylamine (0.89 mL, 6.4 mmol) in dichloromethane (30 mL) was added trimethylchlorosilane (0.83 mL, 6.4 mmol) and the resulting mixture was stirred until a clear solution was formed. To this solution was added a solution of α-butanoyloxyethyl-p-nitrophenyl carbonate (76) (0.46 g, 1.6 mmol) in dichloromethane (10 mL) and the resulting mixture was stirred for 30 min. The reaction mixture was washed with 10% citric acid (20 mL) and the organic phase was separated. The aqueous layer was further extracted with ether (3×10 mL) and the combined organic phases were dried over $MgSO_4$, then concentrated in vacuo. The resulting residue was purified by reverse phase preparative HPLC (acetonitrile, water 0.1% formic acid) to afford 70 mg (21%) of the title compound (75). $^1$H NMR (CD3OD, 400 MHz): 0.95 (t, J=7.6 Hz, 3H), 1.32–1.58 (m, 10H), 1.42 (d, J=5.6 Hz, 3H), 1.67 (m, 2H), 2.24 (s, 2H), 2.30 (t, J=7.6 Hz, 2H), 3.24 (s, 2H), 6.74 (q, J=5.6 Hz, 1H). MS (ESI) m/z 330.28 $(M+H)^+$.

The acid form was quantitatively converted to the corresponding sodium salt by dissolution in water (5 mL), addition of an equimolar quantity of 0.5 N $NaHCO_3$, followed by lyophilization.

Example 13

1-{[(α-Isobutanoyloxyethoxy)carbonyl]aminomethyl}-1-Cyclohexane Acetic Acid (77)

Following the procedure of Example 12, and substituting silver isobutyrate for silver butyrate, provided 70 mg (21%) of the title compound (77). $^1$H NMR ($CD_3OD$, 400 MHz): 1.12 (d, J=7.2 Hz, 3H), 1.14 (d, J=7.2 Hz, 3H), 1.32–1.58 (m, 10H), 1.44 (d, J=5.6 Hz, 3H), 2.28 (s, 2H), 2.56 (m, 1H), 3.25 (m, 2H), 6.73 (q, J=5.6 Hz, 1H). MS (ESI) m/z 330.30 $(M+H)^+$.

The acid form was quantitatively converted to the corresponding sodium salt by dissolution in water (5 mL), addition of an equimolar quantity of 0.5 N $NaHCO_3$, followed by lyophilization.

Example 14

1-{[(α-Pivaloxyethoxy)carbonyl]aminomethyl}-1-Cyclohexane Acetic Acid (78)

Following the procedure of Example 12, and substituting silver pivalate for silver butyrate, provided 80 mg (36%) of the title compound (78). $^1$H NMR ($CDCl_3$, 400 MHz): 1.13 (s, 9H), 1.32–1.58 (m, 10H), 1.41 (d, J=5.6 Hz, 3H), 2.27 (s, 2H), 3.25 (m, 2H), 5.41 (t, 1H), 6.73 (q, J=5.6 Hz, 1H). MS (ESI) m/z 344.20 $(M+H)^+$.

The acid form was quantitatively converted to the corresponding sodium salt by dissolution in water (5 mL), addition of an equimolar quantity of 0.5 N $NaHCO_3$, followed by lyophilization.

Example 15

1-{[(α-Acetoxyisobutoxy)carbonyl]aminomethyl}-1-Cyclohexane Acetic Acid (79)

Following the procedure of Example 2, and substituting 1-chloro-2-methylpropyl chloroformate for 1-chloroethyl chloroformate, provided 212 mg (38%) of the title compound (79). $^1$H NMR ($CD_3OD$, 400 MHz): 0.99 (m, 6H), 1.32–1.58 (m, 10H), 1.88 (m, 1H), 2.08 (s, 3H), 2.38 (s, 2H), 3.25 (s, 2H), 6.52 (d, J=4.4 Hz,1H); MS (ESI) m/z 330.30 $(M+H)^+$.

Example 16

1-{[(α-Propanoyloxyisobutoxy)carbonyl]aminomethyl}-1-Cyclohexane Acetic Acid (80)

Following the procedure of Example 11, and substituting 1-chloro-2-methylpropyl-p-nitrophenyl carbonate for 1-chloroethyl-p-nitrophenyl carbonate, provided 190 mg (44%) of the title compounds (80). $^1$H NMR (CD$_3$OD, 400 MHz): 0.90 (d, J=6.6 Hz, 3H), 0.91 (d, J=6.6 Hz, 3H), 0.98 (t, J=7.6 Hz, 3H), 1.32–1.58 (m, 10H), 1.83 (m, 1H), 2.18 (s, 2H), 2.28 (q, J=7.6 Hz, 2H), 3.25 (s, 2H), 6.52 (d, J=4.4 Hz, 1H). MS (ESI) m/z 344.34 (M+H)$^+$.

Example 17

1-{[(α-Butanoyloxyisobutoxy)carbonyl]aminomethyl}-1-Cyclohexane Acetic Acid (81)

Following the procedure of Example 2 and substituting 1-chloro-2-methylpropyl chloroformate and mercuric butyrate for 1-chloroethyl chloroformate and mercuric acetate, respectively, provided 95 mg (36%) of the title compound (81). $^1$H NMR (CD$_3$OD, 400 MHz): 1.12 (t, J=7.6 Hz, 3H), 1.13 (d, J=6.6 Hz, 3H), 1.14 (d, J=6.6 Hz, 3H), 1.32–1.58 (m, 10H), 1.87 (m, 2H), 2.22 (m, 1H), 2.42 (s, 2H), 2.46 (t, J=7.6 Hz, 2H), 3.44 (m, 2H), 6.78 (d, J=4.8 Hz, 1H). MS (ESI) m/z 358.30 (M+H)$^+$.

Example 18

1-{[(α-Isobutanoyloxyisobutoxy)carbonyl]aminomethyl}-1-Cyclohexane Acetic Acid (82)

Following the procedure of Example 2, and substituting 1-chloro-2-methylpropyl chloroformate and mercuric isobutyrate for 1-chloroethyl chloroformate and mercuric acetate, respectively, provided 95 mg (36%) of the title compound (82). $^1$H NMR (CD$_3$OD, 400 MHz): 0.95 (d, J=7.2 Hz, 3H), 0.97 (d, J=7.2 Hz, 3H), 1.05 (d, J=6.6 Hz, 3H), 1.06 (d, J=6.6 Hz, 3H), 1.32–1.58 (m, 10H), 1.98 (m, 1H), 2.24 (s, 2H), 2.45 (m, 1H), 3.24 (m, 2H), 6.42 (d, J=4.8 Hz, 1H). MS (ESI) m/z 358.27 (M+H)$^+$.

Example 19

1-{[(α-Pivaloxyisobutoxy)carbonyl]aminomethyl}-1-Cyclohexane Acetic Acid (83)

Following the procedure of Example 12, and substituting 1-chloro-2-methylpropyl-p-nitrophenyl carbonate and silver pivalate for 1-chloroethyl-p-nitrophenyl carbonate and silver butyrate, respectively, provided 10 mg (9%) of the title compound (83). $^1$H NMR (CD$_3$OD, 400 MHz): 0.98 (d, J=6.6 Hz, 3H), 0.99 (d, J=6.6 Hz, 3H), 1.19 (s, 9H), 1.32–1.58 (m, 10H), 2.08 (m, 1H), 2.28 (s, 2H), 3.21 (m, 2H), 6.49 (d, 1H); MS (ESI) m/z 372.31 (M+H)$^+$.

Example 20

1-{[(α-Benzoyloxyisobutoxy)carbonyl]aminomethyl}-1-Cyclohexane Acetic Acid (84)

Following the procedure of Example 11, and substituting 1-chloro-2-methylpropyl-p-nitrophenyl carbonate and silver benzoate for 1-chloroethyl 1-p-nitrophenyl carbonate and silver propionate, respectively, provided 109 mg (40%) of the title compound (84). $^1$H NMR (CD$_3$OD, 400 MHz): 1.18 (d, J=7.2 Hz, 6H), 1.32–1.58 (m, 10H), 2.42 (m, 1H), 2.28 (s, 2H), 3.45 (s, 2H), 6.99 (d, J=4.8 Hz, 1H), 7.76 (m, 2H), 7.92 (m, 1H), 8.26 (m, 2H). MS (ESI) m/z 392.22 (M+H)$^+$.

Example 21

1-{[(α-Acetoxyisopropoxy)carbonyl]aminomethyl}-1-Cyclohexane Acetic Acid (85)

Step A: Isopropenyl-p-Nitrophenyl Carbonate (86)

To a mixture of p-nitrophenol (5.76 g, 41.5 mmol) and isopropenyl chloroformate (5 g, 41.5 mmol) in dichloromethane (200 mL) at 0° C. was added a solution of pyridine (3.4 mL, 42 mmol) in dichloromethane (50 mL). The resulting mixture was stirred at 0° C. for 30 minutes and then at room temperature for 1 hour. After removing the solvent under reduced pressure, the residue was dissolved in ether and washed with water, 10% citric acid and water again. The ether layer was dried over Na$_2$SO$_4$ and evaporated under reduced pressure to give 8.7 g (94%) of the title compound (86) as an off-white solid. $^1$H NMR (CDCl$_3$, 400 MHz): 2.05 (s, 3H), 4.81 (m, 1H), 4.95 (d, J=2 Hz, 1H), 7.42 (d, J=9.2 Hz, 2H), 8.28 (d, J=9.2 Hz, 2H).

Step B: 2-Chloroisopropyl-p-Nitrophenyl Carbonate (87)

Isopropenyl-p-nitrophenyl carbonate (86) (8.7 g, 39 mmol) was dissolved in 4 M hydrogen chloride/dioxane in a sealed vessel. The mixture was stirred at room temperature for 16 hours. Removal of the solvent under reduced pressure gave 10 g (100%) of the title compound (87), which was used in the next reaction without further purification. $^1$H NMR (CDCl$_3$, 400 MHz): 2.10 (s, 6H), 7.42 (d, 2H, J=9.2 Hz), 8.28 (d, J=9.2 Hz, 2H).

Step C: α-Acetoxyisopropyl-p-Nitrophenyl Carbonate (88)

A mixture of 2-chloroisopropyl-p-nitrophenyl carbonate (87) (0.5 g, 1.93 mmol) and mercuric acetate (1.0 g, 3.13 mmol) in dichloromethane (20 mL) was stirred at room temperature for 24 hours. The reaction mixture was filtered to remove solid and the filtrate concentrated under reduced pressure. Chromatography of the resulting residue on silica gel, (20% CH$_2$Cl$_2$/hexanes and then 40% CH$_2$Cl$_2$/hexanes), afforded 227 mg (50%) of the title compound (88). $^1$H NMR (CDCl$_3$, 400 MHz): 1.90 (s, 6H), 2.07 (s, 3H), 7.28 (d, 2H, J=9.2 Hz), 8.28 (d, J=9.2 Hz, 2H).

Step D: 1-{[(α-Acetoxyisopropoxy)carbonyl]aminomethyl}-1-Cyclohexane Acetic Acid (85)

To a mixture containing gabapentin (257 mg, 1.5 mmol) and triethylamine (0.46 mL, 3.3 mmol) in dichloromethane (30 mL) was added trimethylchlorosilane (0.38 mL, 3 mmol) and the mixture stirred until clear. A solution containing α-acetoxyisopropyl-p-nitrophenyl carbonate (88) (0.23 g, 0.8 mmol) in dichloromethane (10 mL) was added and stirred for 30 minutes. The reaction mixture was washed with brine (10 mL) and the organic layer was separated. The aqueous layer was further extracted with ether (3×10 mL) and the combined organic extracts were dried over MgSO$_4$ and then concentrated in vacuo. Chromatography of the resulting residue on silica gel, (hexane:ethyl acetate (4:1)), gave 40 mg (16%) of the title compound (85). ¹H NMR (CD₃OD, 400 MHz): 1.32–1.58 (m, 10H), 1.80 (s, 6H), 2.02 (s, 3H), 2.27 (s, 2H), 3.30 (s, 2H). MS (ESI) m/z 316.21 (M+H)⁺.

Example 22

1-{[(α-Butanoyloxyisopropoxy)carbonyl]aminomethyl}-1-Cyclohexane Acetic Acid (89)

Following the procedure of Example 21, and substituting mercuric butyrate for mercuric acetate, provided 5 mg (5%) of the title compound (89). ¹H NMR (CD₃OD, 400 MHz): 0.99 (t, J=7.6 Hz, 3H), 1.32–1.58 (m, 10H), 1.60 (m, 2H), 1.85 (s, 6H), 2.22 (t, J=7.6, 2H), 2.27 (s, 2H), 3.20 (s, 2H). MS (ESI) m/z 344.24 (M+H)⁺, 366.30 (M+Na)⁺.

Example 23

1-{[(α-Isobutanoyloxyisopropoxy)carbonyl]aminomethyl}-1-Cyclohexane Acetic Acid (90)

Following the procedure of Example 21, and substituting mercuric isobutyrate for mercuric acetate, provided 109 mg (43%) of the title compound (90). ¹H NMR (CD₃OD, 400 MHz): 1.19 (d. J=7.2 Hz, 6H), 1.32–1.58 (m, 10H), 1.82 (s, 6H), 2.38 (s, 2H), 3.25 (s, 2H). MS (ESI) 344.22 (M+H)⁺, 366.24 (M+Na)⁺.

Example 24

1-{[(α-Benzoyloxyisopropoxy)carbonyl]aminomethyl}-1-Cyclohexane Acetic Acid (91)

Following the procedure of Example 21, and substituting mercuric benzoate for mercuric acetate, provided 170 mg (58%) of the title compound (91). ¹H NMR (CDCl₃, 400 MHz): 1.32–1.58 (m, 10H), 1.95 (s, 6H), 2.30 (s, 2H), 3.20 (d, J=6.8, 2H), 5.41 (t, J=6.8 Hz, 1H), 7.40 (m, 2H), 7.52 (m, 1H), 7.98 (m, 2H). MS (ESI) m/z 400.29 (M+Na)⁺.

Example 25

1-{[(α-Nicotinoyloxyisobutoxy)carbonyl]aminomethyl}-1-Cyclohexane Acetic Acid (92)

Step A: 1-{[(α-Chloroisobutoxy)carbonyl]aminomethyl-1-Cyclohexane Acetic Acid (93)

To a mixture containing gabapentin (1.71 g, 10 mmol) and triethylamine (3.06 mL, 22 mmol) in dichloromethane (150 mL) was added trimethylchlorosilane (1.4 mL, 11 mmol) and the resulting mixture was stirred until clear (about 20 min). A solution containing 1-chloro-2-methylpropylchloroformate (1.27 mL, 11 mmol) in dichloromethane (10 mL) was then added at 0° C. and stirred at room temperature for 60 min. The reaction mixture was washed with 10% citric acid (30 mL) and the organic layer separated. The aqueous layer was further extracted with ether (3×20 mL) and the combined organic phases were dried over MgSO₄ and then concentrated in vacuo. Chromatography of the residue on silica gel, eluting with hexane:ethyl acetate (1:4) gave 2.37 g (77%) of the title compound. ¹H NMR (CDCl₃, 400 MHz): δ 1.04 (d, J=6.4 Hz, 3H), 1.06 (d, J=6.4 Hz, 3H), 1.36–1.53 (m, 10H), 2.15 (m, 1H), 2.34 (s, 2H), 3.24 (m, 2H), 5.39 (t, 1H), 6.32 (d, J=5.6 Hz), 1H). MS (ESI) m/z 306.34 (M+H⁺).

Step B: 1-{[(α-Nicotinoyloxyisobutoxy)carbonyl] aminomethyl}-1-Cyclohexane Acetic Acid (92)

A mixture of (93) (268 mg, 0.88 mmol), 1,8-diazabicyclo [5.4.0]undec-7-ene (DBU) (158 μL, 1.01 mmol), and nicotinic acid (637 mg, 5.2 mmol) in acetone was stirred at room temperature for 48 h. After filtration, the filtrate was concentrated in vacuo and the resulting residue was purified by reverse phase preparative HPLC to afford 50 mg (14%) of the title compound. ¹H NMR (CD₃OD, 400 MHz): δ 1.07 (d, J=6.8 Hz, 3H), 1.09 (d, J=6.8 Hz, 3H), 1.32–1.58 (m, 10H), 2.19 (m, 1H), 2.26 (s, 2H), 3.23 (m, 2H), 6.78 (d, J=4.8 Hz, 1H), 7.58 (m, 1H), 8.39 (d, J=6.4 Hz, 1H), 8.76 (d, J=4.4 Hz, 1H), 9.10 (s, 1H). MS (ESI) m/z 393.42 (M+H⁺).

Example 26

1-{[(α-2,2-Diethoxypropanoyloxyisobutoxy)carbonyl]aminomethyl}-1-Cyclohexane Acetic Acid (94)

Step A: Benzyl 1-{[(α-Chloroisobutoxy)carbonyl] aminomethyl}-1-Cyclohexane Acetate (95)

To a solution of (93) (1.02 g, 3.34 mmol) in dichloromethane was added 1,3-dicyclohexylcarbodiimide (758 mg, 3.67 mmol). After stirring at room temperature for 30 min, benzyl alcohol (380 μL, 3.67 mmol) and 4-(dimethylamino)pyridine (catalytic amount) were added. The resulting mixture was stirred at room temperature of 16 h. After filtration, the filtrate was washed with 10% citric acid, dried over Na₂SO₄, and concentrated. Chromatography of the residue on silica gel, eluting with 10% ethyl acetate/hexane, gave 820 mg (62%) of the title compound. ¹H NMR (CDCl₃, 400 MHz): δ 1.03 (d, J=6.4 Hz, 3H), 1.05(d, J=6.4 Hz, 3H), 1.36–1.53 (m, 10H), 2.13 (m, 1H), 2.35 (s, 2H), 3.22 (m, 2H), 5.11 (s, 2H), 5.49 (t, 1H), 6.32 (d, J=4.8 Hz), 1H), 7.34 (m, 5H). MS (ESI) m/z 396.24 (M+H⁺).

Step B: Cesium 2,2-Diethoxypropionate (96)

To a stirred solution of 14 mL (0.2 mol) of pyruvic acid and 80 mL of triethylorthoformate at 10° C. was added 1 mL of concentrated sulfuric acid. The resulting mixture was stirred at 5–10° C. for 1 h and then diluted with 200 mL of dichloromethane. The organic solution was washed successively with water (3×80 mL) and saturated sodium chloride solution (80 mL) and then dried over anhydrous sodium sulfate. The mixture was filtered and then concentrated to give a quantitative yield of 2,2-diethoxypropionic acid as an oil. ¹H NMR (CDCl₃, 400 MHz): δ 1.30 (t, 6H), 1.61 (s, 3H), 3.57 (q, 4H), 8.62 (s, 1H). The acid form was quantitatively converted to its cesium salt by dissolving the acid in water (25 mL) followed by treatment with an equimolar quantity of cesium carbonate, and then lyophilization. ¹H NMR (D₂O, 400 MHz): δ 0.98 (t, 6H), 1.28 (s, 3H), 3.22 (q, 2H), 3.47 (q, 2H).

Step C: Benzyl 1-{[(α-2,2-Diethoxypropanoyloxyisobutoxy)carbonyl]aminomethyl}-1-Cyclohexane Acetate (97)

A mixture of (95) (200 mg, 0.51 mmol) and sodium iodide (114 mg, 0.76 mmol) in acetone was stirred at room temperature for 1 h. Cesium 2,2-diethoxypropionate (96) (300 mg, 1.02 mmol) and DMF (20 mL) were added and the resulting mixture was stirred at 40° C. for 18 h. After filtration, the filtrate was concentrated and the resulting residue was purified by silica gel flash column chromatography, eluting with 10% ethyl acetate/hexane to afford 100 mg (37%) of the title compound. MS (ESI) m/z 522.34 (M+H$^+$).

Step D: 1-{[(α-2,2-Diethoxypropanoyloxyisobutoxy)carbonyl]aminomethyl}-1-Cyclohexane Acetic Acid (94)

A mixture of (97) (200 mg, 0.38 mmol) and 5% Pd-C (catalytically amount) was stirred under hydrogen at room temperature for 16 h. After filtration, the filtrate was concentrated and the resulting residue was purified by reverse phase preparative HPLC to afford 98 mg (60%) of the title compound. $^1$H NMR (CDCl$_3$, 400 MHz): δ 0.97 (d, J=6.8 Hz, 6H), 1.19 (t, J=6.4 Hz, 3H), 1.21 (t, J=6.4 Hz, 3H), 1.32–1.58 (m, 10H,), 1.51 (s, 3H), 2.06 (m, 1H), 2.30 (s, 2H), 3.23 (m, 2H), 3.46 (m, 2H), 3.56 (m, 2H), 5.30 (t, 1H, NH), 6.59 (d, J=4.8 Hz, 1H). MS (ESI) m/z 432.24 (M+H$^+$).

Example 27

1-{[(α-(2-Amino-2-methylpropanoyl)oxyisobutoxy)carbonyl]aminomethyl}-1-Cyclohexane Acetic Acid (98)

Following the procedure of Example 26, and substituting 2-amino-2-methylpropionic acid for 2,2-diethoxypropionic acid, provided the title compound. $^1$H NMR (CDCl$_3$, 400 MHz): δ 0.97 (d, J=6.8 Hz, 6H), 1.44 (s, 3H), 1.45 (s 3H), 1.32–1.58 (m, 10H,), 2.05 (m, 1H), 2.30 (s, 2H), 3.23 (m, 2H), 5.50 (t, 1H, NH), 6.58 (d, J=4.8 Hz, 1H). MS (ESI) m/z 373.48 (M+H$^+$).

Example 28

1-{[(α-Isobutanoyloxybutoxy)carbonyl]aminomethyl}-1-Cyclohexane Acetic Acid (99)

Step A: 2-Isopropyl-1,3-Dithiane (100)

To a mixture of isobutyraldehyde (9.1 mL, 100 mmol) and 1,3-propanedithiol (10 mL, 100 mmol) in dichloromethane at 0° C. was added boron trifluoride diethyl etherate (6.4 mL, 50 mmol). The resulting mixture was stirred at 0° C. for 30 min and at room temperature for 30 min. The reaction mixture was washed with brine, 5% NaHCO$_3$, and brine again. The organic phase was separated and dried over Na$_2$SO$_4$, then concentrated to give 16 g (100%) of the title compound as a yellow liquid. This was carried to the next step without further purification. $^1$H NMR (CDCl$_3$, 400 MHz): δ 1.057 (d, J=7.2 Hz, 3H), 1.059 (d, J=7.2 Hz, 3H), 1.80 (m, 1H), 1.97–2.08 (m, 2H), 2.82 (m, 4H), 4.00 (d, J=5.2 Hz, 1H).

Step B: 2-Isopropyl-2-(α-Hydroxybutyl)-1,3-Dithiane (101)

To a solution of (100) (4 g, 24.7 mmol) in anhydrous tetrahydrofuran (50 mL) at −20° C. was dropwise added n-butyl lithium (1.6M in hexane, 18.5 mL, 29.6 mmol). The stirred mixture was allowed to warm room temperature over 4 h and then cooled to −20° C. again. To this solution was added slowly a solution of n-butyraldehyde (2.7 mL, 29.6 mmol) in anhydrous tetrahydrofuran (10 mL). The resulting mixture was stirred for 16 h between −20° C. and room temperature. The reaction was quenched with saturated ammonium chloride solution and the mixture extracted with ethyl acetate. The organic layer was separated and dried over Na$_2$SO$_4$. After removing the solvent under reduced pressure, flash column chromatography of the residue on silica gel, eluting with 5% ethyl acetate/hexane provided 5 g (85%) of the title compound as a yellow oil. $^1$H NMR (CDCl$_3$, 400 MHz): δ 0.96 (t, J=7.2 Hz, 3H), 1.11 (d, J=6.8, Hz, 3H), 1.17 (d, J=6.8 Hz, 3H), 1.42–1.52 (m, 2H), 1.76 (m, 1H), 1.87–1.95 (m, 2H), 2.04 (m, 2H), 2.62 (m, 4H), 2.94 (m, 2H), 4.03 (d, J=5.2 Hz, 1H).

Step C: 4-Hydroxy-2-Methylheptan-3-one (102)

To a solution of (101) (5.0 g, 21.4 mmol) in acetonitrile (270 mL) was added under vigorous stirring a solution of Hg(ClO$_4$)$_2$ in methanol (30 mL). The resulting mixture was stirred at room temperature for 2 h. After filtration, the filtrate was carefully concentrated under reduced pressure without heating. Purification of the residue using silica gel flash column chromatography (10% ethyl acetate/hexane) provided 2.8 g (91%) of the title compound as colorless liquid. $^1$H NMR (CDCl$_3$, 400 MHz): δ 0.91 (t, J=7.2 Hz, 3H), 1.09 (d, J=7.2 Hz, 3H), 1.10 (d, J=7.2 Hz, 3H), 1.35–1.46 (m, 4H), 1.75 (m, 1H), 2.80 (m, 1H), 3.45 (d, J=5.2 Hz, 1H), 4.29 (m, 1H).

Step D: 2-Methylheptan-3-one-4-p-Nitrophenyl Carbonate (103)

To a mixture of (102) (1.1 g, 7.6 mmol), p-nitrophenyl chloroformate (1.84 g, 9.2 mmol) in anhydrous dichloromethane at 0° C. was added slowly a solution of 4-dimethylaminopyridine (1.12 g, 9.2 mmol) in dichloromethane. After stirring for 1 h at 0° C. and for 4 h at room temperature, the reaction was quenched with 10% citric acid. The organic phase was separated, dried over Na$_2$SO$_4$, and concentrated in vacuo. Flash column chromatography of the residue, eluting with 30% dichloromethane/hexane, provided 2 g (85%) of the title compound as an off-white solid. $^1$H NMR (CDCl$_3$, 400 MHz): δ 0.99 (t, J=7.6 Hz, 3H), 1.12 (d, J=6.8 Hz, 3H), 1.18 (d, J=6.8 Hz, 3H), 1.51 (m, 2H), 1.84 (m, 2H), 2.82 (m, 1H), 5.17 (m, 1H), 7.42 (d, J=6.8 Hz, 2H), 8.25 (d, J=6.8 Hz, 2H).

Step E: 1-{[(α-Isobutanoylbutoxy)carbonyl]aminomethyl}-1-Cyclohexane Acetic Acid (104)

To a mixture containing gabapentin (820 mg, 4.8 mmol) and triethylamine (1.35 mL, 9.6 mmol) in dichloromethane (20 mL) was added trimethylchlorosilane (1.22 mL, 9.6 mmol) and the resulting mixture was stirred for 20 min. To this solution was added (103) (1 g, 3.2 mmol) in dichloromethane (10 mL) and the resulting mixture was stirred for 60 min. The reaction mixture was washed with 10% citric acid (20 mL) and the organic layer separated. The aqueous layer was further extracted with ether (3×10 mL) and the combined organic extracts were dried over MgSO$_4$ then concentrated in vacuo. Chromatography of the residue on silica gel, eluting with hexane:ethyl acetate (4:1) to remove p-nitrophenol, then further eluting with hexane:ethyl acetate (1:4) gave 780 mg (72%) of the title compound. $^1$H NMR (CDCl$_3$, 400 MHz): δ 0.91 (t, J=7.2 Hz, 3H), 1.04 (d, J=6.8 Hz, 3H), 1.12 (d, J=6.8 Hz, 3H), 1.36–1.53 (m, 12H), 1.74 (m, 2H), 2.33 (s, 2H), 2.78 (m, 1H), 3.22 (m, 2H), 5.11 (m, 1H), 5.48 (t, 1H, NH). MS (ESI) m/z 342.24 (M+H$^+$).

Step F: 1-{[(α-Isobutanoyloxybutoxy)carbonyl]aminomethyl}-1-Cyclohexane Acetic Acid (99)

To a solution of (104) (780 mg, 2.3 mmol) in dichloromethane (20 mL) was added m-chloroperoxybenzoic acid (1.03 g, 4.6 mmol) and $NaHCO_3$ (386 mg, 4.6 mmol). After stirring for 16 h at room temperature, another batch of m-chloroperoxybenzoic acid (791 mg, 4.6 mmol) and $NaHCO_3$ (386 mg, 4.6 mmol) was added. The resulting mixture was stirred for another 8 h and then treated with 10% citric acid. After filtration, the organic layer was separated, dried over $Na_2SO_4$, and concentrated. The residue was purified by reverse phase preparative HPLC to afford 79 mg (11%) of the title compound. $^1$H NMR ($CDCl_3$, 400 MHz): δ 0.94 (t, J=7.2 Hz, 3H), 1.153 (d, J=7.2 Hz, 3H), 1.150 (d, J=7.2 Hz, 3H), 1.32–1.58 (m, 12H), 1.74 (m, 2H), 2.28 (s, 2H), 2.56 (m, 1H), 3.23 (m, 2H), 5.27 (t, J=6.8 Hz, 1H, NH), 6.71 (t, J=5.6 Hz, 1H). MS (ESI) m/z 358.30 (M+H$^+$).

The above acid was quantitatively converted to the corresponding sodium salt by dissolving the acid in water (5 mL) followed by addition of an equimolar quantity of 0.5 N $NaHCO_3$ and lyophilization.

Example 29

Methyl 1-{[(α-Isobutanoyloxyisobutoxy)carbonyl]aminomethyl}-1-Cyclohexane Acetate (105)

Step A: Methyl 1-{[(α-Chloroisobutoxy)carbonyl]aminomethyl}-1-Cyclohexane Acetate (106)

A mixture of (93) (1.0 g, 3.3 mmol), benzene (90 mL), and methanol (10 mL) was cooled to 0° C. Trimethylsilyldiazomethane was added slowly at 0° C. until the yellow color persisted. The mixture was stirred at 0° C. for 30 min until the reaction was complete (monitored by TLC). After removing the solvent under reduced pressure, chromatography of the resulting residue on silica gel, eluting with 10% ethyl acetate/hexane gave 760 mg (72%) of the title compound. MS (ESI) m/z 320.24 (M+H$^+$).

Step B: Methyl 1-{[(α-Isobutanoyloxyisobutoxy)carbonyl]aminomethyl}-1-Cyclohexane Acetate (105)

A mixture of (106) (760 mg, 2.38 mmol), silver carbonate (394 mg, 1.4 mmol), and isobutyric acid (442 μL, 4.76 mmol) in chloroform was stirred at room temperature for 24 h. Another batch of silver carbonate (394 mg, 1.4 mmol) and isobutyric acid (442 μL, 4.76 mmol) was added, and the resulting mixture was stirred for another 24 h. After filtration, the filtrate was concentrated and the resulting residue purified by silica gel flash column chromatography, eluting with 10% ethyl acetate/hexane, to afford 560 mg (63%) of the title compound. $^1$H NMR ($CDCl_3$, 400 MHz): δ 0.94 (d, J=6.8 Hz, 3H), 0.96 (d, J=6.8 Hz, 3H), 1.15 (d, J=7.2 Hz, 3H), 1.17 (d, J=7.2 Hz, 3H), 1.32–1.58 (m, 10H), 2.01 (m, 1H), 2.19 (s, 2H), 2.55 (m, 1H), 3.18 (m, 2H), 3.67 (s, 3H), 5.33 (t, 1H), 6.56 (d, J=4.8 Hz, 1H). MS (ESI) m/z 372.38 (M+H$^+$).

Example 30

Methyl 1-{[(α-Benzoyloxyisobutoxy)carbonyl]aminomethyl}-1-Cyclohexane Acetate (107)

A mixture of 1-{[(α-benzoyloxyisobutoxy)carbonyl]aminomethyl}-1-cyclohexane acetic acid (84) (150 mg, 0.38 mmol), benzene (18 mL), and methanol (2 mL) was cooled to 0° C. Trimethylsilyldiazomethane was added slowly at 0° C. until the yellow color persisted. The mixture was stirred at 0° C. for 30 min until the reaction was complete (monitored by TLC). After removing the solvent under reduced pressure, chromatography of the residue on silica gel, eluting with 5% ethyl acetate/hexane gave 98 mg (64%) of the title compound. $^1$H NMR ($CDCl_3$, 400 MHz): δ 1.02 (d, J=6.4 Hz, 3H), 1.03 (d, J=6.4 Hz, 3H), 1.32–1.52 (m, 10H), 2.14 (m, 1H), 2.27 (s, 2H), 3.17 (m, 2H), 3.62 (s, 3H), 5.40 (t, 1H), 6.81 (d, J=4.8 Hz, 1H), 7.40 (m, 2H), 7.54 (m, 1H), 8.12 (m, 2H). MS (ESI) m/z 406.29 (M+H$^+$).

Example 31

1-{[N-[(α-Isobutanoyloxyethoxy)carbonyl]-4-Bromophenylalaninyl]aminomethyl}-1-Cyclohexane Acetic Acid (108)

Step A: 1-{[(4-Bromophenylalaninyl)aminomethyl}-1-Cyclohexane Acetate (109)

To a 40 mL vial was added an N-Boc-4-bromophenylalanine (1.72 g, 5 mmol), dicyclohexylcarbodiimide (1.24 g, 6 mmol), N-hydroxysuccinimide (0.7 g, 6 mmol), and acetonitrile (20 mL). The reaction mixture was shaken at 25° C. for 4 h. The precipitated dicyclohexylurea was removed by filtration. To the filtrate was added an aqueous solution (30 mL) of gabapentin hydrochloride (1.04 g, 6 mmol), and sodium hydroxide (0.4 g, 10 mmol). The reaction was stirred at 22–25 C for 16 h. The reaction mixture was diluted with ethyl acetate (100 mL) and washed with 0.5 M aqueous citric acid (2×100 mL) and water (2×100 mL). The organic phase was separated, dried ($MgSO_4$), filtered and concentrated under reduced pressure. The residue was dissolved in trifluoroacetic acid (40 mL) and allowed to stand at 22–25° C. for 2 h. The solvent was removed under reduced pressure. The residue was dissolved in water (4 mL) and filtered through a 0.25 μm nylon membrane filter prior to purification by preparative HPLC (Phenomenex 250×21.2 mm, 5 μm LUNA C18 column, 100% water for 5 minutes, then 0–60% acetonitrile in water with 0.05% TFA over 20 minutes at 20 mL/min). The pure fractions were combined and the solvent was removed under reduced pressure to afford 1.7 g (70%) of the title compound (109) as a white solid. MS (ESI) m/z 397.02, 399.01 (M+H$^+$).

Step B: 1-{[N-[(α-Isobutanoyloxyethoxy)carbonyl]-4-Bromophenylalaninyl]aminomethyl}-1-Cyclohexane Acetic Acid (108)

To a stirred suspension of (109) (200 mg, 0.51 mmol) in dichloromethane at 0° C. was added triethylamine (141 μL, 1.01 mmol) and trimethylchlorosilane (129 mL, 1.01 mmol). The resulting mixture was stirred for 15 min at 0° C., then a solution of α-isobutanoyloxyethyl-p-nitrophenyl carbonate (111) (144 mg, 0.51 mmol) in dichloromethane was added. The mixture was stirred at room temperature for 7 h (monitored by LC/MS) and then the reaction mixture was diluted with dichloromethane and acidified with citric acid. The organic layer was separated, washed with brine, and dried over $Na_2SO_4$. After filtration and concentration, the crude product was purified by preparative LC/MS to afford 92 mg of the title compound. $^1$H-NMR ($CD_3OD$, 400 MHz): δ 1.10 (m, 6H), 1.46–1.25 (m, 13H), 2.20 (m, 2H), 2.48 (m, 1H), 2.84 (m, 1H), 3.06 (m, 1H), 3.17 (m, 1H), 4.36 (m, 1H), 6.67 (q, J=5.6 Hz, 1H), 7.17 (d, J=2.0, 8.0 Hz, 2H), 7.42 (dd, J=2.0, 8.0 Hz, 2H).

Example 32

3-{[(α-Isobutanoyloxyethoxy)carbonyl]aminomethyl}-5-Methylhexanoic Acid (110)

Step A: α-Isobutanoyloxyethyl-p-Nitrophenyl Carbonate (111)

A solution of 1-chloroethyl-p-nitrophenyl carbonate (57) (2.0 g, 8.14 mmol), and mercury isobutyrate (6.13 g, 16.29 mmol) in dichloromethane (10 mL) was stirred at 45° C. for 24 h. The reaction was then cooled to room temperature and diluted with hexane to precipitate mercury salts. The precipitate was filtered through a pad of Celite, and the filtrate was concentrated in vacuo to afford 2.5 g of crude product. Chromatography of the residue on silica gel, eluting with a gradient of 10% dichloromethane/hexane to 20% dichloromethane/hexane afforded 1.2 g (52%) of the title compound. $^1$H-NMR (CDCl$_3$, 400 MHz): δ 1.21–1.99 (m, 6H), 1.62 (d, J=5.6 Hz, 3H), 2.61 (m, 1H), 6.84 (q, J=5.6 Hz, 1H), 7.41 (dt, J=6.8, 2.4 Hz, 2H), 8.29 (dt, J=6.8, 2.4 Hz, 2H).

Step B: 3-{[(α-Isobutanoyloxyethoxy)carbonyl]aminomethyl}-5-Methylhexanoic Acid (110)

To a stirred suspension of pregabalin (2) (150 mg, 0.94 mmol) in anhydrous dichloromethane (10 mL) at 0° C. was added triethylamine (0.26 mL, 1.88 mmol) and trimethylchlorosilane (0.24 mL, 1.88 mmol). After stirring for 15 min at 0° C., a solution of α-isobutanoyloxyethyl-p-nitrophenyl carbonate (111) (267 mg, 0.94 mmol) in dichloromethane (3 mL) was added. The resulting mixture was stirred at room temperature for 1.5 h. The reaction mixture was acidified with citric acid and extracted with dichloromethane. The combined organic extracts were washed with brine and dried over Na$_2$SO$_4$. After filtration and evaporation, the crude product was purified by silica gel chromatography, eluting first with dichloromethane to remove nitrophenol, then with 30% ethyl acetate in dichloromethane to afford 130 mg (48%) of the title compound as a mixture of two diastereomers. $^1$H-NMR (CDCl$_3$, 400 MHz): δ 0.90 (m, 6H), 1.70 (m, 8H), 1.46 (d, J=5.6 Hz, 3H), 1.66 (1H, m), 2.15 (m, 1H), 2.33 (m, 2H), 2.53 (m, 1H), 3.12 (m, 1H), 3.29 (m, 1H), 5.08 (t, J=6.0 Hz, 1H), 6.79 (m, 1H).

Example 33

3-{[(α-Isobutanoyloxyisobutoxy)carbonyl]aminomethyl]-5-Methyl-Hexanoic Acid (112)

Step A: 1-Chloro-2-Methylpropyl-p-Nitrophenyl Carbonate (113)

To an ice cold reaction mixture containing p-nitrophenol (4.06 g, 29 mmol) and 1-chloro-2-methylpropyl chloroformate (5.0 g, 29 mmol) in dichloromethane (200 mL) was added a solution of pyridine (2.78 mL, 32 mmol) in dichloromethane (50 mL). The mixture was stirred at 0° C. for 30 min and then at room temperature for 1 h. After evaporation of the solvent under reduced pressure, the residue was dissolved in ether and washed with water, 10% citric acid and water again. The ether layer was separated, dried over Na$_2$SO$_4$ and evaporated under reduced pressure to give 7.9 g (100%) of the title compound as an off-white solid. $^1$H NMR (CDCl$_3$, 400 MHz): δ 1.12 (d, J=6.6 Hz, 3H), 1.13 (d, J=6.6 Hz, 3H), 2.29 (m, 1H), 6.24 (d, J=4.8 Hz,1H), 7.42 (d, J=9.2 Hz, 2H), 8.28 (d, J=9.2 Hz, 2H).

Step B: α-Isobutanoyloxyisobutyl-p-Nitrophenyl Carbonate (114)

Following the procedure for preparation of (111), and substituting (113) for (57), provided the title compound in 15% yield with a 70% recovery of starting material. $^1$H-NMR (CDCl$_3$, 400 MHz): δ 1.07 (d, J=6.8 Hz), 1.21 (m, 6H), 2.18 (m, 1H), 2.26 (m, 1H), 6.60 (d, J=5.2 Hz, 1H), 7.42 (m, 2H), 8.28 (m, 2H).

Step C: 3-{[(α-Isobutanoyloxyisobutoxy)carbonyl]aminomethyl]-5-Methyl-Hexanoic Acid (112)

Following the procedure of preparation for (110), and substituting (114) for (111), provided the title compound as a mixture of two diastereomers in 51% yield. $^1$H-NMR (CDCl$_3$, 400 MHz): δ 0.89 (m, 12H), 1.17 (m, 8H), 1.65 (m, 1H), 2.02 (m, 1H), 2.16 (m, 1H), 2.33 (m, 2H), 2.56 (m, 1H), 3.13 (m, 1H), 3.30 (m, 1H), 5.00 (m, 1H), 6.57–6.56 (m, 1H).

Example 34

3-{[(α-Benzoyloxyisobutoxy)carbonyl]aminomethyl]-5-Methyl-Hexanoic Acid (115)

Step A: α-Benzoyloxyisobutyl-p-Nitrophenyl Carbonate (116)

Following the procedure of preparation for (111), substituting (113) for (57) and mercury benzoate for mercury isobutyrate, provided the title compound in 11% yield with a 50% recovery of starting material. $^1$H-NMR (CDCl$_3$, 400 MHz): δ 1.15 (d, J=3.2 Hz, 3H), 1.16 (d, J=3.2 Hz, 3H), 2.30 (m, 1H), 6.87 (d, J=4.4 Hz, 1H), 7.42 (dd, J=7.2, 2.0 Hz, 2H), 7.48 (t, J=7.6 Hz, 2H), 7.62 (t, J=7.6 Hz, 1H), 8.09 (dd, J=8.0, 1.0 Hz, 2H), 8.27 (dd, J=7.2, 2.0 Hz, 2H).

Step B: 3-{[(α-Benzoyloxyisobutoxy)carbonyl]aminomethyl]-5-Methyl-Hexanoic Acid (115)

Following the procedure of preparation for (110), and substituting (116) for (111), provided the title compound as a mixture of two diastereomers in 58% yield. $^1$H-NMR (CDCl$_3$, 400 MHz): δ 0.87(m, 6H), 1.05 (m, 6H), 1.16 (m, 2H), 1.64 (m, 1H), 2.17 (m, 2H), 2.32 (m, 2H), 3.12 (m, 1H), 3.29 (m, 1H), 5.01 (br s, 1H), 6.82 (m, 1H), 7.44 (m, 2H), 7.57 (m, 1H), 8.05 (m, 2H).

Example 35

1-{[((5-Methyl-2-Oxo-1,3-Dioxol-4-en-4-yl)methoxy)carbonyl]aminomethyl}-1-Cyclohexane Acetic Acid (117)

Step A: Benzyl 2-Diazo-3-Oxo-Butyric Acid (118)

To a solution of benzyl acetoacetate (5.0 g, 26.01 mmol) and 4-acetamido-benzenesulfonyl azide (6.25 g, 26.01 mmol) in acetonitrile (200 mL) at 0° C. was dropwise added triethylamine (10.9 mL, 78.03 mmol). The resulting mixture was stirred for 30 min at 0° C. and 4 h at room temperature.

After concentrating under reduced pressure, the residue was triturated with 2:1 ethyl ether/petroleum ether (3×100 mL). The combined organic extract was filtered through a pad of Celite topped with silica gel. Removal of the solvent under reduced pressure afforded 4.74 g of the title compound as off-white crystals. $^1$H-NMR (CDCl$_3$, 400 MHz): δ 2.49 (s, 3H), 5.27 (s, 2H), 7.38 (m, 5H).

Step B: Benzyl 2-Hydroxy-3-Oxo-Butyric Acid (119)

A solution of the diazo compound (118) (4.74 g, 21.74 mmol) in THF (110 mL) and H$_2$O (50 mL) was heated under reflux with Rh$_2$(OAc)$_2$ (77 mg, 0.17 mmol) for 4 h and allowed to cool to room temperature. The mixture was concentrated in vacuo and the aqueous residue was extracted with ethyl acetate. The combined organic extracts were washed with brine, dried over Na$_2$SO$_4$, filtered and concentrated in vacuo to provide 4.5 g of crude product. $^1$H-NMR (CDCl$_3$, 400 MHz): δ 2.28 (s, 3H), 3.90 (s, 1H), 4.82 (s, 1H), 5.26 (m, 2H), 7.37 (m, 5H).

Step C: 4-Benzyloxycarbonyl 5-Methyl-2-Oxo-1,3-Dioxol-4-ene (120)

To a suspension of carbonyldiimidazole (6.88 g, 42.45 mmol) in THF (50 mL) at 0° C. was added a solution of alcohol (119) (4.50 g, 21.22 mmol) in dry THF (50 mL). The resulting mixture was stirred for 5 h at 0° C., then overnight at room temperature. The mixture was concentrated in vacuo and the residue was partitioned with water and ethyl acetate/hexane. The organic layer was separated and washed with saturated NH$_4$Cl, brine, and dried over Na$_2$SO$_4$. After filtration and concentration, the crude product was purified by flash chromatography on silica gel, eluting with 20% ethyl acetate in hexane to afford 2.6 g of the title compound. $^1$H-NMR (CDCl$_3$, 400 MHz): δ 2.48 (s, 3H), 5.27 (s, 2H), 7.37 (br. s, 5H).

Step D: 5-Methyl-2-Oxo-1,3-Dioxol-4-enyl-4-Carboxylic Acid (121)

To a solution of compound (120) (2.6 g, 10.92 mmol) in 50 mL of ethanol was added 260 mg of Pd/C (5%) and the resulting mixture was stirred under a hydrogen atmosphere for 1 h. Filtration and removal of solvent under reduced pressure provided 1.62 g of the title compound. $^1$H-NMR (CD$_3$OD, 400 MHz): δ 2.41 (s, 3H).

Step E: 4-Hydroxymethyl-5-Methyl-2-Oxo-1,3-Dioxol-4-ene (122)

To a solution of the acid (121) (1.62 g, 11.10 mmol) and anhydrous DMF (112 μL) in dry dichloromethane (50 mL) at 0° C. was dropwise added oxalyl chloride (6.1 mL of 2M solution, 12.2 mmol). After stirring for 30 min at 0° C. and 1 h at room temperature, the solvent was removed under reduced pressure. The residue was dissolved in anhydrous dichloromethane (65 mL) and cooled to −78° C. To this solution was dropwise added a solution of Bu$_4$NBH$_4$ (3.14 g, 12.2 mmol, in 20 mL dichloromethane) over 10 min. After stirring for 1 h at −78° C., the mixture was cautiously quenched with 0.1N HCl (30 mL) and allowed to warm to room temperature. The aqueous layer was separated and was extracted with EtOAc (3×50 mL) and the combined organic extract was washed with brine and dried over Na$_2$SO$_4$. After removing the solvent under reduced pressure, column chromatography on silica gel, eluting with 50% EtOAc in dichloromethane provided 767 mg of the title compound. $^1$H-NMR (CD$_3$OD, 400 MHz): δ 2.09 (s, 3H), 4.34 (s, 2H).

Step F: Benzyl 1-{[((5-Methyl-2-Oxo-1,3-Dioxol-4-en-4-yl)methoxy)carbonyl]-aminomethyl}-1-Cyclohexane Acetate (123)

A suspension of the alcohol (122) (767 mg, 5.9 mmol) and benzyl 1-isocyanatomethyl-1-cyclohexane acetate (5.9 mmol) in toluene was refluxed overnight. After removing the solvent under reduced pressure, the residue was purified by flash column chromatography, eluting with 30% EtOAc in hexane to provide 510 mg of the title compound. $^1$H-NMR (CD$_3$OD, 400 MHz): δ 1.58–1.30 (m, 10H), 2.18 (s, 3H), 2.35 (s, 2H), 3.17 (d, J=6.8 Hz, 2H), 4.80 (s, 2H), 5.11 (s, 2H), 5.44 (t, J=6.8 Hz, 1H), 7.36 (m, 5H).

Step G: 1-{[((5-Methyl-2-Oxo-1,3-Dioxol-4-en-4-yl)methoxy)carbonyl]-aminomethyl}-1-Cyclohexane Acetic Acid (117)

To a solution of compound (123) (510 mg, 1.41 mmol) in ethanol (20 mL) was added 59 mg of Pd/C (5%) and the resulting mixture was stirred under a hydrogen atmosphere for 1 h. Filtration and removal of volatiles under reduced pressure provided the crude product, which was purified by preparative LC/MS to provide 105 mg of the title compound. $^1$H-NMR (CD$_3$OD, 400 MHz): δ 1.52–1.36 (m, 10H), 2.16 (s, 3H), 2.27 (s, 2H), 3.22 (s, 2H), 4.86 (s, 2H).

Example 36

Piperidinium 1-{(1-Methyl-3-Oxo-But-1-enyl)aminomethyl}-1-Cyclohexane Acetate (124)

2,4-pentanedione (103 μL, 1 mmol), gabapentin (171 mg, 1 mmol), and piperidine (99 μL, 1 mmol) were mixed in anhydrous methanol (10 mL). The resulting mixture was heated under reflux for 4 h. Removal of the solvent under reduced pressure gave the title compound with purity greater than 90%. $^1$H NMR (CDCl$_3$, 400 MHz): δ 1.34–1.62 (m, 12H), 1.71 (m, 4H), 1.94 (s, 3H), 1.96 (s, 3H), 2.26 (s, 2H), 2.98 (m, 4H), 3.38 (d, J=6 Hz, 2H), 4.90 (s, 1H), 5.20 (s, br, 2H), 8.64 (t, J=6 Hz, 1H). MS (ESI) m/z 252.35 (M−H$^−$).

Example 37

Piperidinium 1-{1-[(2-Oxo-Tetrahydrofuran-3-ylidene)ethyl]aminomethyl}-1-Cyclohexane Acetate (125)

2-Acetylbutyrolactone (108 μL, 1 mmol), gabapentin (171 mg, 1 mmol), and piperidine (99 μL, 1 mmol) were mixed in anhydrous methanol (10 mL). After heating under reflux for 6 h, the solvent was removed under reduced pressure to afford the title compound with purity greater than 90%. $^1$H NMR (CDCl$_3$, 400 MHz): δ 1.34–1.62 (m, 12H), 1.71 (m, 4H), 1.94 (s, 3H), 2.24 (s, 2H), 2.81 (t, J=7.6 Hz, 2H), 2.99 (m, 4H), 3.31 (d, J=6.4 Hz, 2H), 4.23 (t, J=7.6 Hz, 2H), 5.17 (s, br, 2H), 8.64 (t, J=6.4 Hz, 1H). MS (ESI) m/z 280.34 (M−H$^−$).

Example 38

Piperidinium 1-{(2-Carbomethoxy-Cyclopent-1-enyl)aminomethyl}-1-Cyclohexane Acetate (126)

Methyl 2-oxocyclopentanecarboxylate (124 µL, 1 mmol), gabapentin (171 mg, 1 mmol), and piperidine (99 µL, 1 mmol) were mixed in anhydrous methanol (10 mL). After heating under reflux for 16 h, the solvent was removed under reduced pressure to afford the title compound with purity greater than 90%. $^1$H NMR (CDCl$_3$, 400 MHz): δ 1.29–1.60 (m, 12H), 1.72 (m, 4H), 1.79 (m, J=7.6 Hz, 2H), 2.24 (s, 2H), 2.49 (t, J=7.6 Hz, 2H), 2.55 (t, J=7.6 Hz, 2H), 2.99 (m, 4H), 3.24 (d, J=6.8 Hz, 2H), 3.63 (s, 3H), 5.06 (s, br, 2H), 7.93 (s, br, 1H). MS (ESI) m/z 294.36 (M−H$^-$).

Example 39

Piperidinium 1-{(1-Methyl-2-(Ethoxycarbonyl)-3-Ethoxy-3-Oxoprop-1-enyl)aminomethyl}-1-Cyclohexane Acetate (127)

Diethyl acetylmalonate (202 mg, 1 mmol), gabapentin (171 mg, 1 mmol), and piperidine (99 µL, 1 mmol) were mixed in anhydrous ethanol (10 mL). After heating under reflux for 16 h, the solvent was removed under reduced pressure to give the title compound with purity greater than 90%. $^1$H NMR (CDCl$_3$, 400 MHz): δ 1.28 (t, J=7.2 Hz, 6H), 1.38–1.64 (m, 12H), 1.75 (m, 4H), 1.96 (s, 3H), 2.23 (s, 2H), 2.99 (m, 4H), 3.24 (d, J=5.2 Hz, 2H), 4.20 (q, J=7.2 Hz, 4H), 4.35 (s, br, 2H), 7.79 (t, J=5.2 Hz, 1H). MS (ESI) m/z 354.38 (M−H$^-$).

Example 40

1-{[(α-(2-(2-Methyl-1,3-Dioxolan-2-yl)carboxyisobutoxy)carbonyl]-aminomethyl}-1-Cyclohexane Acetic Acid (128)

Step A: 2-Methyl-1,3-Dioxolane-2-Carboxylic Acid (129)

To a stirred mixture containing ethyl pyruvate (11.1 mL, 0.1 mol) and ethylene glycol (5.6 mL, 0.1 mol) in anhydrous dichloromethane (100 mL) at 0° C. was added boron trifluoride dietherate (6.4 mL, 0.05 mol) and catalytic amount of acetic acid. The resulting mixture was stirred at 40° C. for 16 h and then diluted with 100 mL of dichloromethane. The organic solution was washed successively with saturated sodium chloride solution (2×80 mL). The organic layer was separated and the combined organic extracts were concentrated. The residue was treated with 1N sodium hydroxide at room temperature. After stirring at room temperature for 3 h (monitored by TLC), citric acid was added to adjust the pH to 4. The product was extracted with dichloromethane, dried over Na$_2$SO$_4$ and concentrated to afford 5.1 g (38%) of the title compound (129) as a clear liquid. This material was used in the next reaction without further purification. $^1$H NMR (CDCl$_3$, 400 MHz): δ 1.55 (s, 3H), 4.03 (m, 4H).

Step B: Benzyl 1-{[(α-(2-(2-Methyl-1,3-Dioxolan-2-yl)carboxyisobutoxy)carbonyl]aminomethyl}-1-Cyclohexane Acetate (130)

A mixture containing benzyl 1-{[(α-chloroisobutoxy)carbonyl]aminomethyl}-1-cyclohexane acetate (95) (1 g, 2.53 mmol), (129) (673 mg, 5.1 mmol), silver carbonate (557 mg, 2.53 mmol), and triethylamine (709 µL, 5.1 mmol) in chloroform was stirred at room temperature for 16 h. After filtration, the filtrate was concentrated. The resulting residue was purified by silica gel chromatography, eluting with 15% ethyl acetate/hexane to afford 510 mg (41%) of the title compound (130). MS (ESI) m/z 492.40 (M+H$^+$).

Step C: 1-{[(α-(2-(2-Methyl-1,3-Dioxolan-2-yl)carboxyisobutoxy)carbonyl]-aminomethyl}-1-Cyclohexane Acetic Acid (128)

A mixture of (130) (470 mg, 0.96 mmol) and 5% Pd-C (catalytic amount) in ethanol was stirred under hydrogen at room temperature for 16 h. Filtration and concentration gave 382 mg (100%) of the title compound (128). $^1$H NMR (CDCl$_3$, 400 MHz): δ 0.96 (d, J=6.8 Hz, 3H), 0.97 (d, J=6.8 Hz, 3H), 1.32–1.58 (m, 10H), 1.59 (s, 3H), 2.06 (m, 1H), 2.32 (s, 2H), 3.26 (m, 2H), 4.08 (m, 4H), 5.29 (t, 1H, NH), 6.55 (d, J=4.8 Hz, 1H). MS (ESI) m/z 402.32 (M+H$^+$).

The acid form was quantitatively converted to its corresponding sodium salt by dissolution in water (5 mL), addition of an equimolar quantity of 0.5 N NaHCO$_3$, followed by lyophilization.

Example 41

1-{[(α-Propanoyloxybutoxy)carbonyl]aminomethyl}-1-Cyclohexane Acetic Acid (131)

Step A: 1-Chlorobutyl-1-chloroformate (132)

To a solution of triphosgene (33.3 g, 112 mmol) in ether (150 mL) at −40° C. was added n-butyraldehyde (9.0 mL, 100 mmol). The resulting mixture was treated with pyridine (4.04 mL, 50 mmol) and stirred at −10° C. to −20° C. for 2 h. The reaction was then warmed to room temperature, filtered through a pad of Celite, and the filtrate concentrated under vacuum to afford the chloroformate (132) (15 g, 87.7%). $^1$H NMR (CDCl$_3$, 400 MHz): δ 0.98 (m, 3H), 1.53 (m, 2H), 2.06 (m, 2H), 6.31 (m, 1H).

Step B: 1-{[(α-Chlorobutoxy)carbonyl]aminomethyl-1-Cyclohexane Acetic Acid (133)

To a suspension of gabapentin (8.55 g, 50 mmol) in dichloromethane at 0° C. was added triethylamine (21 mL, 150 mmol) and TMSCl (6.4 mL, 50 mmol). The resulting suspension was stirred at 0° C. for 20 minutes and then a solution of chloroformate (132) (8.55 g, 50 mmol) in dichloromethane was added. The reaction was stirred for another hour at room temperature, then quenched with citric acid and extracted with dichloromethane. The combined organic phase was washed with water and brine and dried over Na$_2$SO$_4$. Filtration and evaporation gave 9.5 g of crude product (133), which was used directly in the subsequent step.

Step C: Benzyl 1-{[(α-Chlorobutoxy)carbonyl]aminomethyl-1-Cyclohexane Acetate (134)

To a solution of crude (133) (6.0 g) and benzyl alcohol (4.1 mL, 39.2 mmol) in dichloromethane at 0° C. was added dicyclohexylcarbodiimide (6.07 g, 29.4 mmol) and DMAP (120 mg, 0.98 mmol), and the resulting reaction mixture was stirred at room temperature for 2 h, then filtered through a pad of Celite. The filtrate was washed with brine and dried over Na$_2$SO$_4$. After filtration and evaporation, the crude product was purified by flash chromatography on silica gel, eluting with 10% ethyl acetate in hexane, to afford 5.8 g of the desired ester (134). (CDCl$_3$, 400 MHz): δ 0.95 (t, J=7.4 Hz, 3H), 1.72–1.20 (m, 14H), 2.34 (s, 2H), 3.19 (m, 2H), 5.10 (s, 2H), 5.47 (t, J=6.2 Hz, 1H), 6.42 (t, J=5.8 Hz, 1H), 7.33 (m, 5H).

Step D: Benzyl 1-{[(α-Propanoyloxybutoxy)carbonyl]aminomethyl}-1-Cyclohexane Acetate (135)

A suspension of (134) (5.8 g, 14.7 mmol), propionic acid (1.64 mL, 22.0 mmol) and Ag$_2$CO$_3$ (6.07 g, 22.0 mmol) in chloroform (80 mL) was stirred at room temperature. The reaction was judged complete by TLC after 5 hours. The reaction mixture was then filtered through a pad of Celite, the filtrate washed with brine and dried over Na$_2$SO$_4$. Filtration and evaporation gave a crude product, which was purified by flash chromatography on silica gel, eluting with 15% ethyl acetate in hexane, to afford 2.5 g of title compound (135). (CDCl$_3$, 400 MHz): δ 0.95 (t, J=7.4 Hz, 3H), 1.12 (t, J=7.4 Hz. 3H), 1.54–1.37 (m, 12H), 1.72 (m, 2H), 2.33 (m. 4H), 3.16 (dd, J=6.8, 4.4 Hz), 5.10 (s, 2H), 5.33 (t, J=6.8, 1H), 6.72 (t, J=5.8 Hz), 7.33 (m, 5H).

Step E: 1-{[(α-Propanoyloxybutoxy)carbonyl]aminomethyl}-1-Cyclohexane Acetic Acid (131)

A suspension of (135) (2.5 g, 5.77 mmol) and 10% Pd/C (250 mg) in ethanol (100 mL) was stirred under an atmosphere of hydrogen (balloon) for 30 minutes then was filtered through a pad of Celite. The filtrate was concentrated under reduced pressure to afford the crude product, which was purified by preparative LC-MS to give 1.21 g of the desired acid (131). (CDCl$_3$, 400 MHz): 0.97 (t, J=7.2 Hz, 3H), 1.15 (t, J=7.2 Hz, 3H), 1.50–1.38 (m, 12H), 1.72 (m, 2H), 2.32 (m, 4H), 3.18 (dd, J=6.4, 4.4 Hz, 2H), 5.27 (t, J=6.4 Hz, 1H), 6.72 (t, J=5.6 Hz, 1H). MS (ESI) m/z 344.39 (M+H)$^+$.

Example 42

In Vitro Determination of Caco-2 Cellular Permeability of Prodrugs

The passive permeability of the prodrugs of the current invention may be assessed in vitro using standard methods well known in the art (See, e.g., Stewart, et al., *Pharm. Res.*, 1995, 12, 693). For example, passive permeability may be evaluated by examining the flux of a prodrug across a cultured polarized cell monolayer (e.g., Caco-2 cells). Caco-2 cells obtained from continuous culture (passage less than 28) were seeded at high density onto Transwell polycarbonate filters. Cells were maintained with DMEM/10% fetal calf serum+0.1 mM nonessential amino acids+2 mM L-Gln, 5% CO$_2$/95% 0$_2$, 37° C. until the day of the experiment. Permeability studies were conducted at pH 6.5 apically (in 50 mM MES buffer containing 1 mM CaCl$_2$, 1 mM MgCl$_2$, 150 mM NaCl, 3 mM KCl, 1 mM NaH$_2$PO4, 5 mM glucose) and pH 7.4 basolaterally (in Hanks' balanced salt solution containing 10 mM HEPES) in the presence of efflux pump inhibitors (250 µM MK-571, 250 µM Verapamil, 1 mM Ofloxacin). Inserts were placed in 12 or 24 well plates containing buffer and incubated for 30 min at 37° C. Prodrug (200 µM) was added to the apical or basolateral compartment (donor) and concentrations of prodrug and/or released parent drug in the opposite compartment (receiver) were determined at intervals over 1 hour using LC/MS/MS. Values of apparent permeability (P$_{app}$) were calculated using the equation:

$$P_{app} = V_r(dC/dt)/(AC_o)$$

Here V$_r$ is the volume of the receiver compartment in mL; dC/dt is the total flux of prodrug and parent drug (µM/s), determined from the slope of the plot of concentration in the receiver compartment versus time; C$_o$ is the initial concentration of prodrug in µM; A is the surface area of the membrane in cm$^2$. Preferably, prodrugs with significant transcellular permeability demonstrate a value of P$_{app}$ of ≧1×10$^{-6}$ cm/s and more preferably, a value of P$_{app}$ of ≧1×10$^{-5}$ cm/s, and still more preferably a value of P$_{app}$ of ≧5×10$^{-5}$ cm/s. Typical values of P$_{app}$ obtained for prodrugs of GABA analogs are shown in the following table:

| Compound | P$_{app}$ (apical to basolateral) (cm/s) | P$_{app}$ (basolateral to apical) (cm/s) | Ratio A-B/B-A |
|---|---|---|---|
| (51) | 1.06 × 10$^{-4}$ | 1.25 × 10$^{-5}$ | 8.5 |
| (56) | 3.1 × 10$^{-5}$ | 2.0 × 10$^{-6}$ | 15.5 |
| (62) | 2.10 × 10$^{-5}$ | 6.40 × 10$^{-6}$ | 3.3 |
| (68) | 8.43 × 10$^{-5}$ | 2.26 × 10$^{-5}$ | 3.7 |
| (69) | 1.84 × 10$^{-4}$ | 5.22 × 10$^{-6}$ | 35.2 |
| (70) | 1.78 × 10$^{-5}$ | 1.68 × 10$^{-6}$ | 10.6 |
| (71) | 8.10 × 10$^{-5}$ | 1.99 × 10$^{-5}$ | 4.1 |
| (72) | 2.51 × 10$^{-5}$ | 1.26 × 10$^{-6}$ | 2.0 |
| (77) | 7.41 × 10$^{-5}$ | 1.43 × 10$^{-5}$ | 5.2 |
| (78) | 1.37 × 10$^{-4}$ | 2.46 × 10$^{-5}$ | 5.6 |
| (80) | 6.62 × 10$^{-5}$ | 8.75 × 10$^{-6}$ | 7.6 |
| (81) | 8.65 × 10$^{-5}$ | 1.27 × 10$^{-5}$ | 6.8 |
| (82) | 1.25 × 10$^{-4}$ | 1.82 × 10$^{-5}$ | 6.9 |
| (83) | 1.29 × 10$^{-5}$ | 4.48 × 10$^{-5}$ | 0.3 |
| (84) | 1.26 × 10$^{-4}$ | 1.57 × 10$^{-5}$ | 8.1 |
| (89) | 5.85 × 10$^{-5}$ | 2.34 × 10$^{-6}$ | 25.0 |
| (90) | 9.22 × 10$^{-5}$ | 5.75 × 10$^{-6}$ | 16.0 |

The data in this table shows that the prodrugs disclosed herein have high cellular permeability and should be well absorbed from the intestine. With the exception of compound (83), the apical-to-basolateral permeabilities of these prodrugs exceed their basolateral-to-apical permeabilities. This suggests that these compounds may be substrates for active transport mechanisms present in the apical membrane of Caco cells (though some component of this transcellular permeability may also be mediated by passive diffusion). The greater basolateral-to-apical permeability of (83) suggests that this compound may be subject to efflux across the basolateral membrane, despite the presence of the efflux pump inhibitors MK-571, verapamil and ofloxacin.

Example 43

Uptake of Gabapentin Following Administration of Gabapentin or Gabapentin Prodrugs Intracolonically in Rats Sustained release oral dosage forms, which release drug slowly over periods of 6–24 hours, generally release a significant proportion of the dose within the colon. Thus drugs suitable for use in such dosage forms preferably exhibit good colonic absorption. This experiment was conducted to assess the suitability of gabapentin prodrugs for use in an oral sustained release dosage form.

Step A: Administration Protocol

Rats were obtained commercially and were pre-cannulated in the both the ascending colon and the jugular vein. Animals were conscious at the time of the experiment. All animals were fasted overnight and until 4 hours post-dosing. Gabapentin or gabapentin prodrugs (59), (63), (69), (72), (77), (79), (85), (117) and (126) were administered as a solution (in water or PEG 400) directly into the colon via the cannula at a dose equivalent to 25 mg of gabapentin per kg. Blood samples (0.5 mL) were obtained from the jugular cannula at intervals over 8 hours and were quenched immediately by addition of acetonitrile/methanol to prevent further conversion of the prodrug. Blood samples were analyzed as described below.

Step B: Sample Preparation for Colonic Absorbed Drug

1. In blank 1.5 mL eppendorf tubes, 300 μL of 50/50 acetonitrile/methanol and 20 μL of p-chlorophenylalanine was added as an internal standard.
2. Rat blood was collected at different time points and immediately 100 μL of blood was added into the eppendorf tube and vortexed to mix.
3. 10 μL of a gabapentin standard solution (0.04, 0.2, 1, 5, 25, 100 μg/mL) was added to 90 μL of blank rat blood to make up a final calibration standard (0.004, 0.02, 0.1, 0.5, 2.5, 10 μg/mL). Then 300 μL of 50/50 acetonitrile/methanol was added into each tube followed by 20 μL of p-chlorophenylalanine.
4. Samples were vortexed and centrifuged at 14,000 rpm for 10 min.
5. Supernatant was taken for LC/MS/MS analysis.

Step C: LC/MS/MS Analysis

An API 2000 LC/MS/MS spectrometer equipped with Shidmadzu 10DVp binary pumps and a CTC HTS-PAL autosampler were used in the analysis. A Zorbax XDB C8 4.6×150 mm column was heated to 45° C. during the analysis. The mobile phase was 0.1% formic acid (A) and acetonitrile with 0.1% formic acid (B). The gradient condition was: 5% B for 1 min, then to 98% B in 3 min, then maintained at 98% B for 2.5 min. The mobile phase was returned to 5% B for 2 min. A TurbolonSpray source was used on the API 2000. The analysis was done in positive ion mode and an MRM transition of 172/137 was used in the analysis of gabapentin (MRM transitions 426/198 for (59), 364/198 for (63), 392/198 for (69), 316/198 for (72), 330/198 for (77), 330/198 for (79), 316/198 for (85) and 327.7/153.8 for (117) were used). 20 μL of the samples were injected. The peaks were integrated using Analyst 1.1 quantitation software. Following colonic administration of each of these prodrugs, the maximum plasma concentrations of gabapentin ($C_{max}$), as well as the area under the gabapentin plasma concentration vs. time curves (AUC) were significantly greater (>2-fold) than that produced from colonic administration of gabapentin itself. For example, prodrug (77) provided both gabapentin $C_{max}$ and AUC values greater than 10-fold higher than gabapentin itself. This data demonstrates that compounds of the invention may be formulated as compositions suitable for enhanced absorption and/or effective sustained release of GABA analogs to minimize dosing frequency due to rapid systemic clearance of these GABA analogs.

Example 44

Sustained Release of Gabapentin Following Prodrug Administration Using Osmotic Mini-Pump Devices in Beagle Dogs Gabapentin or the gabapentin prodrugs (77) and (82) (at a dose equivalent to 10 mg of gabapentin per kg) were dissolved in a suitable solvent (e.g., water, PEG 400, etc.) and filled into preweighed Alzet® mini-osmotic pump devices (Model 2001D) (Durect Corp., Cupertino, Calif.). The filled Alzets were pre-equilibrated by soaking in isotonic saline at 37° C. for 3 hours and stored in sealed containers at 4° C. overnight. Alzets were then administered orally to four fasted male beagle dogs (approx. 6.5 kg). Animals were fed at 4 hr after each dose. Blood samples (1.0 mL) were withdrawn at intervals over 48 hours and processed immediately for plasma. Plasma samples were frozen and stored at −80° C. until analyzed using the method described above. Both prodrugs afforded gabapentin concentrations in plasma at 12 hours post-dosing that were greater than 2-fold the concentration of gabapentin seen following administration of gabapentin itself in the Alzet device. This data further confirms that compounds of the invention may be formulated as compositions suitable for effective sustained release of GABA analogs.

Example 45

Uptake of Pregabalin Following Administration of Pregabalin or Pregabalin Prodrugs Intracolonically in Rats The protocol of Example 43 was repeated with pregabalin and the pregabalin prodrugs (110) and (112). Following colonic administration of each of these prodrugs, the maximum plasma concentrations of pregabalin ($C_{max}$), as well as the area under the pregabalin plasma concentration vs. time curves (AUC) were significantly greater (>2-fold) than that produced from colonic administration of pregabalin itself.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

What is claimed is:

1. A compound of Formula (I), Formula (II) or Formula (III):

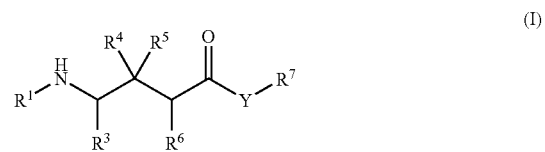

(I)

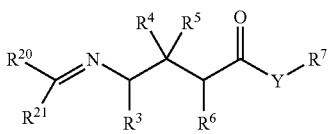

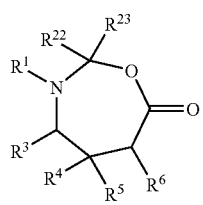

or a pharmaceutically acceptable salt, hydrate or solvate thereof, wherein:

m, n, t and u are 0;

X is O or $NR^{16}$;

W is O or $NR^{17}$;

Y is O or S;

$R^1$ is selected from the group consisting of hydrogen, $R^{24}C(O)$—, $R^{25}OC(O)$—, $R^{24}C(S)$—, $R^{25}OC(S)$—, $R^{25}SC(O)$—, $R^{25}SC(S)$—, $(R^9O)(R^{10}O)P(O)$—, $R^{25}S$—,

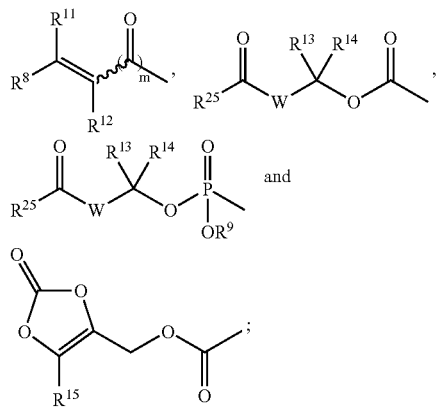

m is 0, each $R^2$ is independently selected from the group consisting of hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy or optionally, $R^2$ and $R^{16}$ together with the atoms to which they are bonded form a cycloheteroalkyl or substituted cycloheteroalkyl ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, arylalkyl, substituted arylalkyl, cycloalkyl, substituted cycloalkyl, cycloheteroalkyl, substituted cycloheteroalkyl, heteroarylalkyl and substituted heteroarylalkyl or optionally, $R^4$ and $R^5$ together with the carbon atom to which they are bonded form a cycloalkyl, substituted cycloalkyl, cycloheteroalkyl, substituted cycloheteroalkyl or bridged cycloalkyl ring;

$R^8$ and $R^{12}$ are independently selected from the group consisting of hydrogen, acyl, substituted acyl, alkoxycarbonyl, substituted alkoxycarbonyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally $R^8$ and $R^{12}$ together with the carbon atoms to which they are bonded form a cycloalkyl, substituted cycloalkyl, cycloheteroalkyl or substituted cycloheteroalkyl ring;

$R^{11}$ is selected from the group consisting of hydrogen, alkyl, substituted alkyl, acyl, substituted acyl, aryl, substituted aryl, arylalkyl, substituted arylalkyl, carbamoyl, substituted carbamoyl, cyano, cycloalkyl, substituted cycloalkyl, heterocycloalkyl, substituted heterocycloalkyl, heteroaryl, substituted heteroaryl, heteroarylalkyl, substituted heteroarylalkyl, alkoxycarbonyl, substituted alkoxycarbonyl, cycloheteroalkyloxycarbonyl, substituted cycloheteroalkyloxycarbonyl, aryloxycarbonyl, substituted aryloxycarbonyl, heteroaryloxycarbonyl, substituted heteroaryloxycarbonyl and nitro;

$R^7$, $R^9$, $R^{10}$, $R^{15}$, $R^{16}$ and $R^{17}$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{13}$ and $R^{14}$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl or optionally, $R^{13}$ and $R^{14}$ together with the carbon atom to which they are bonded form a cycloalkyl, substituted cycloalkyl, cycloheteroalkyl or substituted cycloheteroalkyl ring;

$R^{20}$ and $R^{21}$ are independently selected from the group consisting of hydrogen, acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl or optionally $R^{20}$ and $R^{21}$ together with the carbon atom to which they are bonded form a cycloalkyl, substituted cycloalkyl, cycloheteroalkyl or substituted cycloheteroalkyl ring;

$R^{22}$ and $R^{23}$ are independently selected from the group consisting of hydrogen, alkyl, substituted alkyl, aryl, substituted aryl, arylalkyl and substituted arylalkyl or optionally, $R^{22}$ and $R^{23}$ together with the carbon atom to which they are bonded form a cycloalkyl, substituted cycloalkyl, cycloheteroalkyl or substituted cycloheteroalkyl ring;

$R^{24}$ is selected from the group consisting of hydrogen, acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{25}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and with the provisos that:

when $R^3$ and $R^6$ are both hydrogen, then $R^4$ and $R^5$ are neither both hydrogen nor both methyl;

in a compound of Formula (I) when X is $NR^{16}$, then $R^1$ is not hydrogen;

in a compound of Formula (I) neither $R^1$, $R^7O$—, $R^{24}C(O)$—, $R^{25}C(O)$— nor $R^{25}O$— is a moiety derived from a bile acid;

in a compound of Formula (I) when $R^1$ is $R^{24}C(O)$—, then $R^{24}$ is not methyl, tert-butyl, 2-aminoethyl, 3-aminopropyl, benzyl, phenyl or 2-(benzoyloxymethyl)phenyl;

in a compound of Formula (I) when $R^1$ is $R^{25}OC(O)$—, then $R^{25}$ is not $R^{26}C(O)CR^{13}R^{14}$—, wherein $R^{26}$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

in a compound of Formula (I) when $R^1$ is $R^{25}OC(O)$—, then $R^{25}$ is not methyl, tert-butyl or benzyl;

in a compound of Formula (I) when and $R^2$ is $R^{25}C(O)OCR^{13}R^{14}OC(O)$— then if either $R^{13}$ or $R^{14}$ is hydrogen, alkoxycarbonyl, substituted alkoxycarbonyl, carbamoyl, cycloalkoxycarbonyl or substituted cycloalkoxycarbonyl, the other of $R^{13}$ or $R^{14}$ is not hydrogen.

2. The compound of claim 1 which is 1-{[(α-propanoyloxybutoxy)carbonyl]aminomethyl}-1-cyclohexane acetic acid, or a pharmaceutically acceptable salt, hydrate or solvate thereof.

3. A pharmaceutical composition, comprising a therapeutically effective amount of a compound according to claim 2, or a pharmaceutically acceptable salt, hydrate or solvate thereof.

4. A pharmaceutical composition comprising a therapeutically effective amount of a compound according to claim 1, or a pharmaceutically acceptable salt, hydrate or solvate thereof.

* * * * *

UNITED STATES PATENT AND TRADEMARK OFFICE
CERTIFICATE OF CORRECTION

PATENT NO.        : 7,186,855 B2
APPLICATION NO.   : 10/313825
DATED             : March 6, 2007
INVENTOR(S)       : Gallop et al.

It is certified that error appears in the above-identified patent and that said Letters Patent is hereby corrected as shown below:

On the cover page, in item (75) line 7, the inventor's name "Ian R. Ollman" should be changed to
-- Ian R. Ollmann --

Signed and Sealed this

Fourteenth Day of September, 2010

David J. Kappos
*Director of the United States Patent and Trademark Office*